(12) United States Patent
Kato et al.

(10) Patent No.: US 10,227,407 B2
(45) Date of Patent: Mar. 12, 2019

(54) ANTI-PODOPLANIN ANTIBODY

(71) Applicants: Yukinari Kato, Miyagi (JP); ZENOAQ RESOURCE CO., LTD., Fukushima (JP)

(72) Inventors: Yukinari Kato, Miyagi (JP); Mika Kato, Miyagi (JP)

(73) Assignees: Yukinari Kato, Miyagi (JP); ZENOAQ RESOURCE CO., LTD., Fukushima (JP)

( * ) Notice: Subject to any disclaimer, the term of this patent is extended or adjusted under 35 U.S.C. 154(b) by 112 days.

(21) Appl. No.: 14/914,704

(22) PCT Filed: Oct. 10, 2014

(86) PCT No.: PCT/JP2014/077137
§ 371 (c)(1),
(2) Date: Aug. 9, 2016

(87) PCT Pub. No.: WO2015/053381
PCT Pub. Date: Apr. 16, 2015

(65) Prior Publication Data
US 2016/0347834 A1     Dec. 1, 2016

(30) Foreign Application Priority Data

| Oct. 10, 2013 | (JP) | 2013-212530 |
| Feb. 27, 2014 | (JP) | 2014-037434 |
| Mar. 6, 2014 | (JP) | 2014-044395 |

(51) Int. Cl.
C07K 16/28    (2006.01)
C07K 16/30    (2006.01)
A61K 39/00    (2006.01)

(52) U.S. Cl.
CPC .............. *C07K 16/28* (2013.01); *C07K 16/30* (2013.01); *C07K 16/3069* (2013.01); *C07K 2317/34* (2013.01); *C07K 2317/51* (2013.01); *C07K 2317/515* (2013.01); *C07K 2317/565* (2013.01)

(58) Field of Classification Search
None
See application file for complete search history.

(56) References Cited

U.S. PATENT DOCUMENTS

| 4,802,174 | A | 1/1989 | Hiraiwa et al. |
| 5,506,135 | A | 4/1996 | Iwasa et al. |
| 2012/0308571 | A1 | 12/2012 | Kato et al. |
| 2014/0017266 | A1* | 1/2014 | Bigner ............ A61K 47/48484 424/183.1 |
| 2014/0235827 | A1 | 8/2014 | Fujita et al. |

FOREIGN PATENT DOCUMENTS

| JP | S63-012276 A | 1/1988 |
| JP | H03-103175 A | 4/1991 |
| JP | H03-292896 A | 12/1991 |
| JP | 2012-070648 A | 4/2012 |
| WO | 2011040565 A | 4/2011 |
| WO | 2012128082 A | 9/2012 |

OTHER PUBLICATIONS

Ogasawara et al. (Hybridoma, 2008, 27:259-267).*
Padlan, Advances in Protein Chemistry, 1996, 49:57-133.*
Berglund et al., Protein Science, 2008, 17:606-613.*
Corada, Blood, 2001; 97:1679-84.*
Tzartos et al., Methods in Molecular Biology, 1996, 66:55-66.*
Kulkarni-Kale et al., Nucleic Acid Research, 2005, 33:W168-W171.*
Almagro & Fransson, Frontiers in Bioscience 2008; 13:1619-33.*
De Genst et al., Developmental and Comparative Immunology, 2006, 30:187-98.*
Ward et al., Nature, 1989, 341:544-546.*
Barthelemy et al., Journal of Biological Chemistry, 2008, 283:3639-3654.*
Choi et al., 2011, Molecular BioSystems, 2011, 7:3327-334.*
Griffiths et al., The EMBO Journal, 1993, 12:725-734.*
Klimka et al., British Journal of Cancer, 2000, 83:252-260.*
Beiboer et al., Journal of Molecular Biology, 2000, 296:833-849.*
Kato, Y, "Kesshoban Gyoshu Inshi", Jul. 1, 2012, pp. 2-4, vol. 80, No. 3, Publisher: Wako Jun'yaku Jiho.
Kato, Y., "Characterization of platelet aggregation-inducing factor podoplanin and development of its antibodies", Apr. 1, 2013, pp. 261-265, vol. 85, No. 4, Publisher: Seikagaku.
Oki, et al., "Kokando Ko Podoplanin, Dai18 Kai Gakujutsu Shukai Program Shorokushu", May 29, 2014, pp. 2-4 vol. 105, Publisher: The Japanese Association for molecular Target Therapy of Cancer.
Kato, et al., "Kokando Ko Podoplanin, Dai18 Kai Gakujutsu Shukai Program Shorokushu", May 29, 2014, pp. 4-3, vol. 78, Publisher: The Japanese Association for molecular Target Therapy of Cancer.
Abe, et al., "A novel targeting therapy of malignant mesothelioma using anti-podoplanin antibody", Jun. 15, 2013, pp. 6239-6249, vol. 190, No. 12, Publisher: The Journal of Immunology.
Cortez, et al., "miR-29b and miR-125a regulate podoplanin and suppress invasion in glioblastoma", Nov. 1, 2010, pp. 981-990, vol. 49, No. 11, Publisher: Genes Chromosomes Cancer.
Hatakeyama, et al., "Podoplanin expression in advanced atherosclerotic lesions of human aortas", Apr. 1, 2012, pp. e70-6, vol. 129, No. 4, Publisher: Thromb Res.

(Continued)

*Primary Examiner* — Julie Wu
(74) *Attorney, Agent, or Firm* — Suzannah K. Sundby, Esq.; Canady + Lortz LLP

(57) ABSTRACT

Object of the present invention is to provide various anti-podoplanin antibodies useful as a drug or reagent. The present invention provides an anti-podoplanin antibody or antigen-binding fragment thereof, each having an epitope in any of the following regions in the amino acid sequence of podoplanin represented by SEQ ID NO: 1: (i) from position 56 to position 80, (ii) from position 81 to position 103, (iii) from position 81 to position 88, and (iv) from position 25 to position 57.

12 Claims, 13 Drawing Sheets

Specification includes a Sequence Listing.

(56) References Cited

OTHER PUBLICATIONS

Kaneko, et al., "Functional sialylated O-glycan to platelet aggregation on Aggrus (T1alpha/Podoplanin) molecules expressed in Chinese hamster ovary cells", Sep. 10, 2004, pp. 38838-38843, vol. 279, No. 37, Publisher: J Biol Chem.

Kaneko, et al., "Conservation of a platelet activating domain of Aggrus/podoplanin as a platelet aggregation-inducing factor", Aug. 15, 2006, pp. 52-57, vol. 378, Publisher: Gene.

Kaneko, et al., "Chimeric anti-podoplanin antibody suppresses tumor metastasis through neutralization and antibody-dependent cellular cytotoxicity", Nov. 1, 2012, pp. 1913-1919, vol. 103, No. 11, Publisher: Cancer Science.

Kato, et al., "Molecular identification of Aggrus/T1alpha as a platelet aggregation-inducing factor expressed in colorectal tumors", Dec. 19, 2003, pp. 51599-51605, vol. 278, No. 51, Publisher: J Biol Chem.

Kato, et al., "Aggrus: a diagnostic marker that distinguishes seminoma from embryonal carcinoma in testicular germ cell tumors", Nov. 4, 2004, pp. 8552-8556, vol. 23, No. 52, Publisher: Oncogene.

Kato, et al., "Enhanced expression of Aggrus (T1alpha/podoplanin), a platelet-aggregation-inducing factor in lung squamous cell carcinoma", Jul. 7, 2005, pp. 195-200, vol. 26, No. 4, Publisher: Tumour Biol.

Kato, et al., Nov. 3, 2006, pp. 1301-1307, vol. 349, No. 4.

Kato, et al., "Molecular analysis of the pathophysiological binding of the platelet aggregation-inducing factor podoplanin to the C-type lectin-like receptor CLEC-2", Jan. 1, 2008, pp. 54-61, vol. 99, No. 1, Publisher: Cancer Science.

Kato, et al., "Increased expression of highly sulfated keratan sulfate synthesized in malignant astrocytic tumors", May 16, 2008, pp. 1041-1046, vol. 369, No. 4, Publisher: Biochem Biophys Res Commun.

Mishima, et al., "Increased expression of podoplanin in malignant astrocytic tumors as a novel molecular marker of malignant progression", May 1, 2006, pp. 483-488, vol. 111, No. 5, Publisher: Acta Neuropathol.

Mishima, et al., "Podoplanin expression in primary central nervous system germ cell tumors: a useful histological marker for the diagnosis of germinoma", Jun. 1, 2006, pp. 563-568, vol. 111, No. 6, Publisher: Acta Neuropathol.

Nakazawa, et al., "Prevention of hematogenous metastasis by neutralizing mice and its chimeric anti-Aggrus/podoplanin antibodies", Nov. 1, 2011, pp. 2051-2057, vol. 102, No. 11, Publisher: Cancer Science.

Toyoshima, et al., "Purification and characterization of the platelet-aggregating sialoglycoprotein gp44 expressed by highly metastatic variant . . . adenocarcinoma 26", Feb. 15, 1995, pp. 767-773, vol. 55, No. 4, Publisher: Cancer Research.

Tsuruo, et al., "Characterization of metastatic clones derived from a metastatic variant of mouse colon adenocarcinoma 26", Nov. 1, 1983, pp. 5437-5442, vol. 43, No. 11, Publisher: Cancer Research.

International Search Report received in PCT/JP2014/077137, dated Jan. 20, 2015.

Written Opinion received in PCT/JP2014/077137, dated Jan. 20, 2015.

* cited by examiner

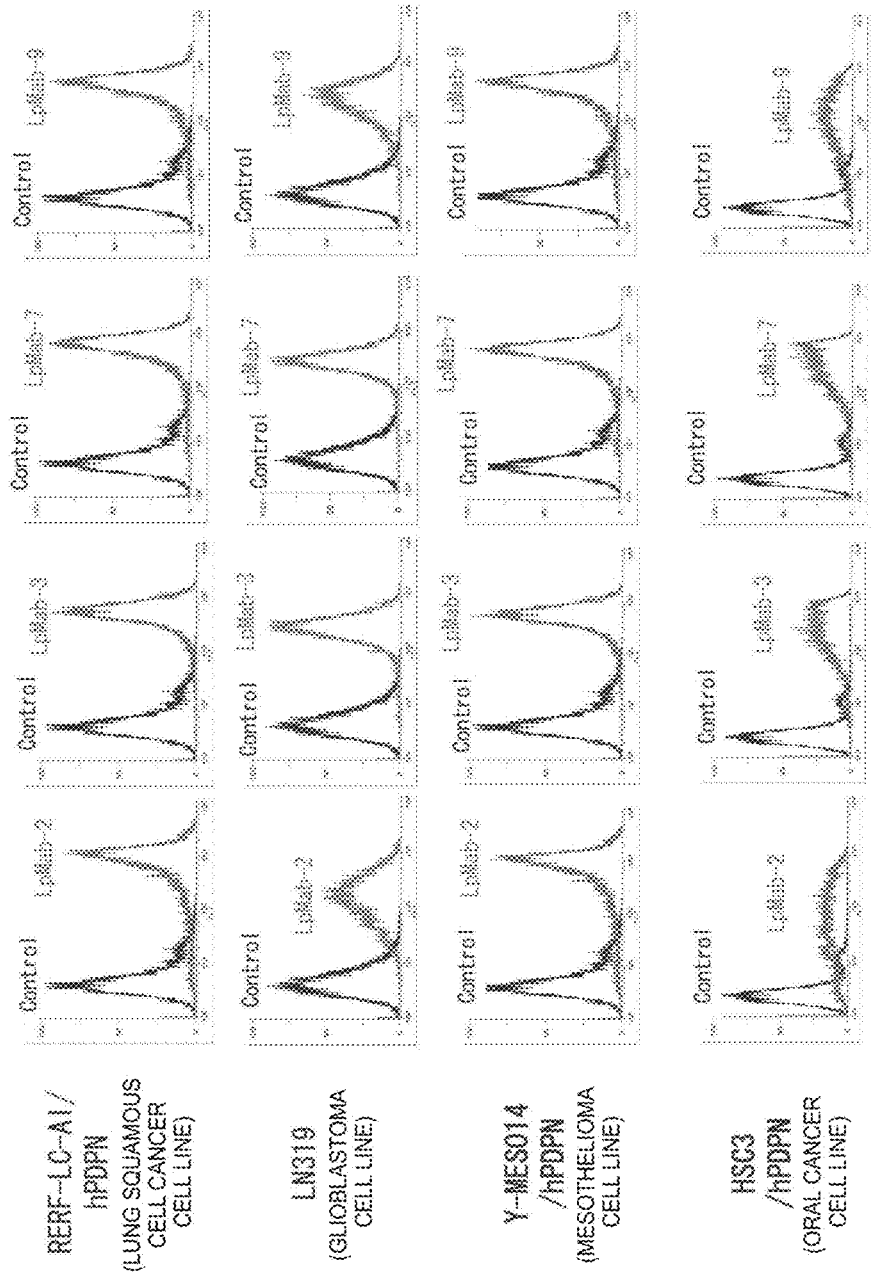

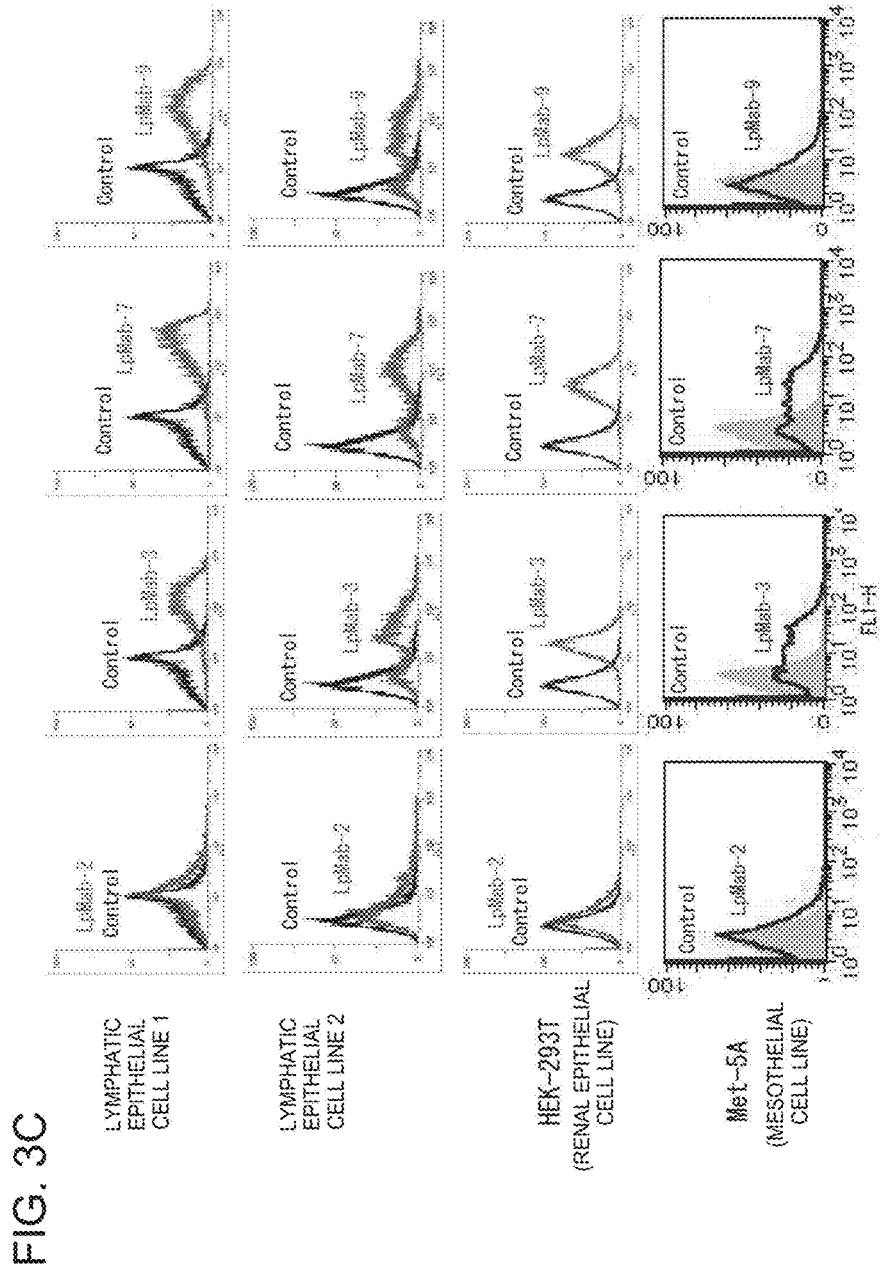

lane 1: PURIFIED ANTIBODY FROM CULTURE SUPERNATANT OF HYBRIDOMAS OF DH2 ANTIBODY
lane 2: PURIFIED ANTIBODY FROM CULTURE SUPERNATANT OF HYBRIDOMAS DH2R OF
       DH2 ANTIBODY ESTABLISHED BY RESET

ANTI-PODOPLANIN ANTIBODY

REFERENCE TO A SEQUENCE LISTING SUBMITTED VIA EFS-WEB

The content of the ASCII text file of the sequence listing named "20160226_101616_001US1_seq" which is 91.1 kb in size was created on Oct. 27, 2014, and electronically submitted via EFS-Web on Feb. 26, 2016, is incorporated herein by reference in its entirety.

TECHNICAL FIELD

The present invention relates to a novel anti-podoplanin antibody, an anticancer agent containing an anti-podoplanin antibody, and the like.

BACKGROUND ART

It has been reported that cancer cell-induced platelet aggregation is observed in hematogenous metastasis of cancer cells. Most of cancer cells that have entered into blood vessels are destroyed by the attack by the immune system of hosts or by physical impact. It has been considered that when platelet aggregation is caused, it protects them from such a procedure and enables metastasis. In addition, it has been considered that platelet aggregation promotes adhesion of cancer cells to vascular endothelial cells or releases growth factors to cause local growth of cancer cells. Further, obstruction of capillary vessels with aggregates of blood platelets attributable to cancer cells also contributes to the promotion of hematogenous metastasis.

Highly metastatic line NL-17 cells and lowly metastatic line NL-14 cells was established by experimentally repeating pulmonary metastasis of the mouse colon cancer cell line colon26 (Non-Patent Document 1). Further, an 8F11 antibody which is a monoclonal antibody exhibiting high reactivity to the NL-17 cells and low reactivity to the NL-14 cells was prepared. In vitro experiment, the NL-17 cells caused platelet aggregation in mice but their activity was inhibited by the 8F11 antibody. In addition, in vivo experiment, experimental pulmonary metastasis of the NL-17 cells was inhibited by the administration of the 8F11 antibody. This has suggested that the NL-17 cells express a platelet aggregation factor recognized by the 8F11 antibody and thereby aggregate mouse platelets, resulting in pulmonary metastasis. This platelet aggregation factor was named later as "podoplanin" (podoplanin) (another name: Aggrus (Aggrus) T1alpha, gp36).

After that, a mouse podoplanin protein was purified from the NL-17 cells by using the 8F11 antibody column and a WGA column (Non-Patent Document 2). The purified podoplanin caused mouse platelet aggregation in the absence of a plasma component in a concentration dependent manner and the aggregation reaction was inhibited completely by the 8F11 antibody.

The present inventors have succeeded in gene cloning of podoplanin (Non-Patent Document 3). Podoplanin is a type I transmembrane protein having, at the C terminal thereof, a transmembrane site. Epitope analysis of the 8F11 antibody which is a neutralizing antibody of mouse podoplanin and detailed mutagenesis experiment have revealed that threonine (Thr) in three repeats of the sequence EDxxVTPG (PLAG domain) is an active center of podoplanin-induced platelet aggregation and is conserved across species (Non-Patent Document 4). About half of the molecular weight of podoplanin is a sugar chain. It has been found using glycosylation-deficient CHO mutant cells (Lec1, Lec2, and Lec8) that sialic acid of an O-linked sugar chain added to Thr in the PLAG domain is an active center of platelet aggregation (Non-Patent Document 5).

The present inventors prepared a highly specific rat monoclonal antibody, an NZ-1 antibody, in order to purify human podoplanin (Non-Patent Document 6). It has been found that the NZ-1 antibody is not only useful for western blotting, flow cytometry, or immunohistostaining but also usable as a high-sensitivity and high-specificity antibody in immunoprecipitation.

The present inventors have reported that the NZ-1 antibody also exhibits ADCC activity and CDC activity in podoplanin-positive tumor cells (Patent Document 1 and Non-Patent Documents 7 to 9).

The NZ-1 antibody inhibited binding between podoplanin and a C-type lectin-like receptor-2 (CLEC-2) and also inhibited podoplanin-induced platelet aggregation in a concentration dependent manner. Tail vein injection of the NZ-1 antibody together with podoplanin expression cells significantly suppressed pulmonary metastasis (Non-Patent Document 10).

High expression of podoplanin in brain tumor, mesothelioma, testicular tumor, ovarian cancer, and various squamous cell cancers (oral cancer, pharyngeal cancer, laryngeal cancer, esophageal cancer, lung cancer, skin cancer, and uterine cervical cancer) has heretofore been reported (Non-Patent Documents 11 to 14). Particularly in astrocytoma, among brain tumors, podoplanin is expressed in proportion to malignancy. It is therefore expected that an anti-podoplanin antibody having not only binding activity but also effector activity such as ADCC activity or CDC activity, if any, can exhibit anticancer action in such cancers. There is accordingly a demand for antibodies having higher specificity or affinity for podoplanin or other antibodies capable of recognizing podoplanin.

In addition to the NZ-1 antibody, various anti-podoplanin antibodies have heretofore been prepared, but any of them have an epitope near the PLAG domain of podoplanin and there is no report on an anti-podoplanin antibody useful for epitopes other than those near the PLAG domain. Further, there are no report on anti-podoplanin antibodies containing both a sugar chain and a peptide sequence in an epitope.

CITATION LIST

Patent Document

Patent Document 1: WO2011/040565

Non-Patent Document

Non-Patent Document 1: Tsuruo T., Yamori T. et al., Cancer Res. 43, 5437-5442, 1983.
Non-Patent Document 2: Toyoshima M., Nakajima M. et al., Cancer Res. 55, 767-773, 1995.
Non-Patent Document 3: Kato Y., Fujita N. et al., J. Biol. Chem. 278, 51599-51605, 2003.
Non-Patent Document 4: Kaneko MK., Kato Y. et al., Gene 378C:52-57, 2006.
Non-Patent Document 5: Kaneko M., Kato Y. et al., J. Biol. Chem. 279, 38838-38843, 2004.
Non-Patent Document 6: Kato Y., Kaneko MK. et al., Biochem. Biophys. Res. Commun., 349:1301-1307, 2006
Non-Patent Document 7: Abe S. et al., J Immunol. 2013 Jun. 15; 190(12):6239-49

Non-Patent Document 8: Kaneko MK. et al., Cancer Sci. 2012 November; 103(11):1913-9

Non-Patent Document 9: Hatakeyama K. et al., Thromb Res. 2012 April; 129(4):e70-6.

Non-Patent Document 10: Kato Y., Kaneko MK. et al., Cancer Sci. 99, 54-61, 2008.

Non-Patent Document 11: Kato Y., Sasagawa I. et al., Oncogene 23, 8552-8556, 2004.

Non-Patent Document 12: Kato Y., Kaneko M. et al., Tumor Biol. 26, 195-200, 2005.

Non-Patent Document 13: Mishima K., Kato Y. et al., Acta Neuropathol. 111(5):483-488, 2006a Non-Patent Document 14: Mishima K., Kato Y. et al., Acta Neuropathol. 111(6):563-568. 2006b

SUMMARY

Technical Problem

An object of the present invention is to provide various anti-podoplanin antibodies useful as a drug, a diagnostic agent, or a reagent.

Solution to Problem

With a view to achieving the above object, the present inventors have proceeded with studies and as a result, have established an anti-podoplanin monoclonal antibody LpMab-2 capable of recognizing an epitope which is in a region other than a PLAG domain. They have verified that LpMab-2 is a tumor-specific antibody capable of recognizing only podoplanin on tumor cells, though podoplanin on tumor cells and podoplanin on non-tumor cells have exactly the same amino acid sequence. This strongly suggests that LpMab-2 recognizes a sugar-chain structure or steric structure added to podoplanin on tumor cells and it is not an antibody against only a sugar chain but it contains, in an epitope thereof, both a peptide sequence of podoplanin and a sugar chain bound thereto.

Further, the present inventors established monoclonal antibodies LpMab-3 and LpMab-9 containing, in an epitope thereof, both a sugar chain and a peptide, similar to LpMab-2. These LpMab-2, LpMab-3, and LpMab-9 contain sialic acid essential for platelet aggregation activity or cancer metastasis activity of podoplanin so that they are antibodies that recognize only activity type podoplanin having platelet aggregation activity or cancer metastasis activity.

In addition, they established a monoclonal antibody LpMab-7 that recognizes podoplanin having any of three molecular weights (about 40 kDa, 30 kDa, and 25 kDa) including podoplanin having the molecular weight (about 30 kDa) which has not been recognized at all, leading to completion of the present invention.

Described specifically, the present invention relates to:

[1] an anti-podoplanin antibody or antigen-binding fragment thereof having an epitope in any of the following regions in an amino acid sequence of podoplanin represented by SEQ ID NO: 1:

(i) from position 56 to position 80;
(ii) from position 81 to position 103;
(iii) from position 81 to position 88; and
(iv) from position 25 to position 57;

[2] an anti-podoplanin antibody or antigen-binding fragment thereof having at least one of the following six CDRs:

a heavy chain CDR1:
GYTFTSYTIH; (SEQ ID NO: 2)

a heavy chain CDR2:
YINPGSGYTNYNEKFQD; (SEQ ID NO: 3)

a heavy chain CDR3:
WDRGY; (SEQ ID NO: 4)

a light chain CDR1:
RSSQTIVHSNGNTYLE; (SEQ ID NO: 5)

a light chain CDR2:
KVSNRFS; (SEQ ID NO: 6)
and a light chain CDR3:
FQGSHVPYT; (SEQ ID NO: 7)

[3] an anti-podoplanin antibody or antigen-binding fragment thereof having at least one of the following six CDRs:

a heavy chain CDR1:
GFTFTRYAMS; (SEQ ID NO: 8)

a heavy chain CDR2:
TISNGGSYTYYLDSVKG; (SEQ ID NO: 9)

a heavy chain CDR3:
REGGQAGPAWFVY; (SEQ ID NO: 10)

a light chain CDR1:
KSSQSLLNSSNQKNYLA; (SEQ ID NO: 11)

a light chain CDR2:
FASTRES; (SEQ ID NO: 12)
and a light chain CDR3:
QQYYSTPPT; (SEQ ID NO: 13)

[4] an anti-podoplanin antibody or antigen-binding fragment thereof having at least one of the following six CDRs:

a heavy chain CDR1:
GFTFSGFGMH; (SEQ ID NO: 14)

a heavy chain CDR2:
YISSVSSRIYYADTVKG; (SEQ ID NO: 15)

a heavy chain CDR3:
EQTGPAWFAY; (SEQ ID NO: 16)

a light chain CDR1:
RSSRNIVQSTGNTYLE; (SEQ ID NO: 17)

a light chain CDR2:
(SEQ ID NO: 18)

-continued

```
KVSNRFS;
and a light chain CDR3:
                                         (SEQ ID NO: 19)
FQGSHVPPVVT;
```

[5] an anti-podoplanin antibody or antigen-binding fragment thereof having at least one of the following six CDRs:

```
                                         (SEQ ID NO: 20)
a heavy chain CDR1: GYTFTKSGMQ;

(SEQ ID NO: 21)
a heavy chain CDR2: WINTHSGVPKYAEDFKG;

(SEQ ID NO: 22)
a heavy chain CDR3: WGGDGAMDY;

(SEQ ID NO: 23)
a light chain CDR1: KSSQSLLKSSSQKNYLA;

(SEQ ID NO: 24)
a light chain CDR2: FASTRES;
and (SEQ ID NO: 25)
a light chain CDR3: QQHYSAPLS;
```

[6] the anti-podoplanin antibody or antigen-binding fragment thereof as described above in any one of [2] to [5] containing, in at least one of the heavy chains CDR 1 to 3 and the light chains CDR 1 to 3, addition, substitution, or deletion of one to several amino acids;

[7] the anti-podoplanin antibody or antigen-binding fragment thereof as described above in any one of [2] to [5], wherein at least one of the heavy chains CDR1 to 3 and the light chains CDR1 to 3 has an amino acid sequence having 80% or more identity with the amino acid sequences of the heavy chains CDR1 to 3 and the light chains CDR1 to 3;

[8] an anti-podoplanin antibody or antigen-binding fragment thereof including:
a heavy chain having an amino acid sequence represented by SEQ ID NO: 26 or 63;
a heavy chain having an amino acid sequence having, in the amino acid sequence represented by SEQ ID NO: 26 or 63, addition, substitution, or deletion of one to several amino acids; or
a heavy chain having an amino acid sequence having 80% or more identity with the amino acid sequence represented by SEQ ID NO: 26 or 63;

[9] an anti-podoplanin antibody or antigen-binding fragment thereof including:
a light chain having an amino acid sequence represented by SEQ ID NO: 27;
a light chain having an amino acid sequence having, in the amino acid sequence represented by SEQ ID NO: 27, addition, substitution, or deletion of one to several amino acids; or
a light chain having an amino acid sequence having 80% or more identity with the amino acid sequence represented by SEQ ID NO: 27;

[10] an anti-podoplanin antibody or antigen-binding fragment thereof including:
a heavy chain having an amino acid sequence represented by SEQ ID NO: 28 or 65;
a heavy chain having an amino acid sequence having, in the amino acid sequence represented by SEQ ID NO: 28 or 65, addition, substitution, or deletion of one to several amino acids; or
a heavy chain having an amino acid sequence having 80% or more identity with the amino acid sequence represented by SEQ ID NO: 28 or 65;

[11] an anti-podoplanin antibody or antigen-binding fragment thereof including:
a light chain having an amino acid sequence represented by SEQ ID NO: 29;
a light chain having an amino acid sequence having, the an amino acid sequence represented by SEQ ID NO: 29, addition, substitution, or deletion of one to several amino acids; or
a light chain having an amino acid sequence having 80% or more identity with the amino acid sequence represented by SEQ ID NO: 29;

[12] an anti-podoplanin antibody or antigen-binding fragment thereof including:
a heavy chain having an amino acid sequence represented by SEQ ID NO: 30 or 67;
a heavy chain having an amino acid sequence having, in the amino acid sequence represented by SEQ ID NO: 30 or 67, addition, substitution, or deletion of one to several amino acids; or
a heavy chain having an amino acid sequence having 80% or more identity with the amino acid sequence represented by SEQ ID NO: 30 or 67;

[13] an anti-podoplanin antibody or antigen-binding fragment thereof including:
a light chain having an amino acid sequence represented by SEQ ID NO: 31;
a light chain having an amino acid sequence having, in the amino acid sequence represented by SEQ ID NO: 31, addition, substitution, or deletion of one to several amino acids; or
a light chain having an amino acid sequence having 80% or more identity with the amino acid sequence represented by SEQ ID NO: 31;

[14] an anti-podoplanin antibody or antigen-binding fragment thereof including:
a heavy chain having an amino acid sequence represented by SEQ ID NO: 32 or 69;
a heavy chain having an amino acid sequence having, in the amino acid sequence represented by SEQ ID NO: 32 or 69, addition, substitution, or deletion of one to several amino acids; or
a heavy chain having an amino acid sequence having 80% or more identity with the amino acid sequence represented by SEQ ID NO: 32 or 69;

[15] an anti-podoplanin antibody or antigen-binding fragment thereof including:
a light chain having an amino acid sequence represented by SEQ ID NO: 33;
a light chain having an amino acid sequence having, in the amino acid sequence represented by SEQ ID NO: 33, addition, substitution, or deletion of one to several amino acids; or
a light chain having an amino acid sequence having 80% or more identity with the amino acid sequence represented by SEQ ID NO: 33;

[16] the antibody or antigen-binding fragment thereof as described above in any one of [1] to [15], wherein one or more N-linked sugar chains have been bound to an Fc region and fucose has not been bound to N-acetylglucosamine at a reducing end of the N-linked sugar chains;

[17] a nucleic acid encoding any one of the heavy chains CDR1 to 3 and the light chains CDR1 to 3 as described above in any one of [2] to [5];

[18] a nucleic acid encoding any one of the heavy chains described above in any one of [8], [10], [12], and [14] and the light chains described above in any one of claims 9, 11, 13, and 15;

[19] an expression vector containing the nucleic acid described above in either [17] or [18];

[20] a transformant containing the expression vector as described above in [19];

[21] a method of producing an anti-podoplanin antibody including:

a step of expressing an antibody in the transformant as described above in [20]; and a step of collecting the antibody;

[22] a pharmaceutical composition containing, as an effective ingredient, the anti-podoplanin antibody or antigen-binding fragment thereof as described above in any one of [1] to [16];

[23] a pharmaceutical composition containing, as an effective ingredient, the anti-podoplanin antibody or antigen-binding fragment thereof as described above in any one of [1] to [16] to which a substance having an anti-cancer activity has been bound; and

[24] the pharmaceutical composition as described above in either [22] or [23], which is a preventive or therapeutic agent of at least one disease selected from the group constituting of tumors, thrombosis, and arteriosclerosis.

Advantageous Effects of Invention

Since a tumor-specific antibody can exhibit anti-tumor activity specifically to tumor cells, drugs having minimized side-effects can be obtained. It is also useful for the delivery of a drug targeting tumor cells and is highly useful as a diagnostic agent or reagent.

In addition, there is a possibility that LpMab-7 recognizes podoplanin having the certain molecular weight which has been undetectable by conventional anti-podoplanin antibodies and recognizes a change in steric structure caused by post-translational modification such as sugar chain modification so that there is a possibility of podoplanin, which has not been detected by existing antibodies, being detected.

The monoclonal antibodies of the present invention are therefore useful as a reagent for research, a diagnostic agent, or a drug candidate.

BRIEF DESCRIPTION OF DRAWINGS

FIG. 3B shows the results of studying, by flow cytometry, the reactivity of anti-podoplanin antibodies (LpMab-2, LpMab-3, LpMab-7, and LpMab-9) of the present invention with various human cancer cell lines.

FIG. 3C shows the results of studying, by flow cytometry, the reactivity of anti-podoplanin antibodies (LpMab-2, LpMab-3, LpMab-7, and LpMab-9) of the present invention with lymphatic epithelial cell lines, renal epithelial cell lines, and mesothelial cell lines.

DESCRIPTION OF EMBODIMENTS (Anti-Podoplanin Antibody)

Figure 1:
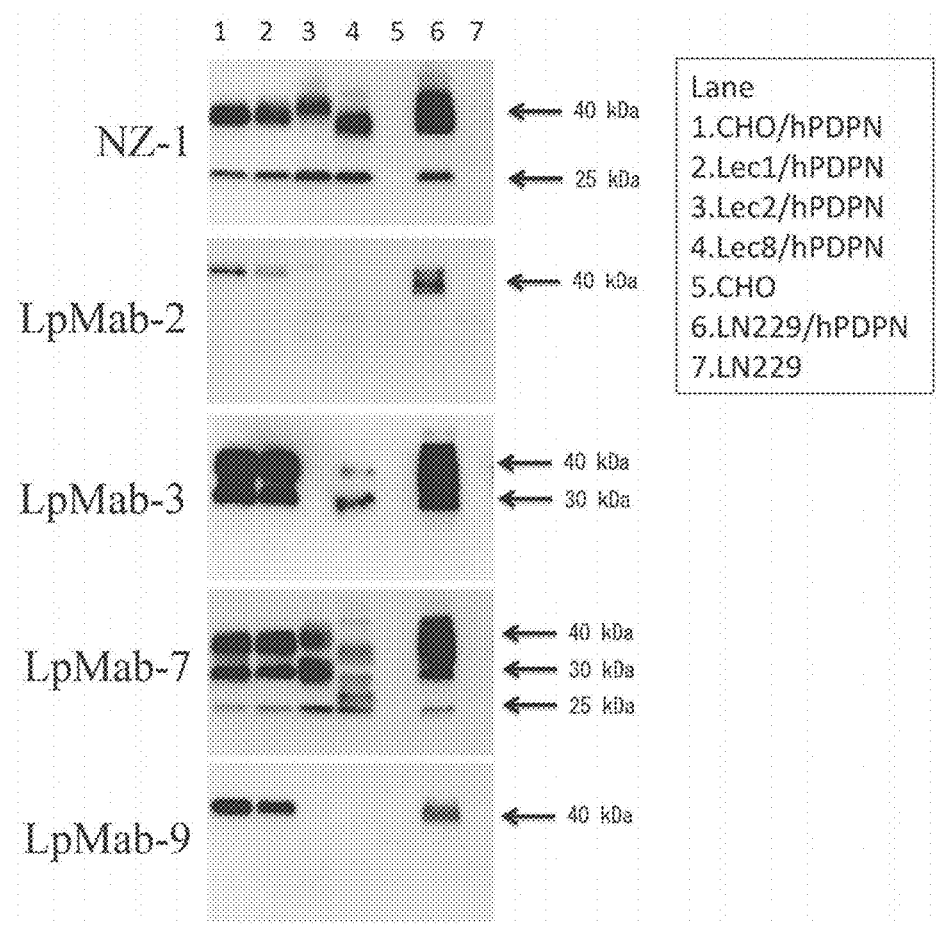
FIG. 1 shows results of electrophoresing respective cell lysates of seven cell lines (CHO/hPDPN, Lec1/hPDPN, Lec2/hPDPN, Lec8/hPDPN, CHO, LN229/hPDPN, and LN229) and performing western blot analysis using five anti-podoplanin antibodies (NZ-1 (rat IgG2a, kappa), LpMab-2 (mouse IgG1, kappa), LpMab-3 (mouse IgG1, kappa), LpMab-7 (mouse IgG1, kappa), and LpMab-9 (mouse IgG1, kappa)).

The term "anti-podoplanin antibody" used in the present invention means an antibody specifically binding to a podoplanin protein composed of an amino acid sequence represented by SEQ ID NO: 1.

The "antibody" used herein has a structure which has two heavy chains (H chains) and two light chains (L chains) associated with each other and has been stabilized by a pair of disulfide bonds. The heavy chains are each composed of a heavy chain variable region VH, heavy chain constant regions CH1, CH2, and CH3, and a hinge region located between CH1 and CH2, while the light chains are each composed of a light chain variable region VL and a light chain constant region CL. Of these regions, a variable region fragment (Fv) composed of VH and VL is a region directly involved in antigen binding and provides the antibody with diversity. The antigen binding region composed of VL, CL, VH and CH1 is called "Fab region" and a region composed of the hinge region, CH2, and CH3 is called "Fc region".

Of the variable regions, the region in direct contact with the antigen is particularly variable and is called "complementarity-determining region: CDR". A relatively mutationless region other than CDR is called "framework region: FR". The light chain variable region and the heavy chain variable region each have three CDRs (heavy chain CDR1 to 3 and light chain CDR1 to 3).

The anti-podoplanin antibody of the present invention may be either a monoclonal antibody or a polyclonal antibody. The anti-podoplanin antibody of the present invention may be any isotype of IgG, IgM, IgA, IgD, and IgE. It may be obtained by immunizing a non-human animal such as mouse, rat, hamster, guinea pig, rabbit, or chicken or it may be a recombinant antibody, or a chimeric antibody, a humanized antibody, a fully humanized antibody, or the like. The "chimeric antibody" means an antibody obtained by linking fragments of antibodies derived from different species.

The term "humanized antibody" as used herein means an antibody obtained by substituting, by an amino acid sequence characteristic to a non-human-derived antibody, a position of a human antibody corresponding thereto. Examples of it include antibodies having heavy chains CDR1 to 3 and light chains CDR1 to 3 of the antibody prepared by immunizing a mouse and, in all the other regions including four respective framework regions (FR) of the heavy chains and light chains, derived from the human antibody. Such an antibody may also be called "CDR grafted antibody". The term "humanized antibody" may include a human chimeric antibody.

The term "antigen binding fragment" of the anti-podoplanin antibody as used herein means a fragment of the anti-podoplanin antibody that binds to podoplanin. Specific examples include, but are not limited to, Fab composed of VL, VH, CL, and CH1 regions; F(ab')2 having two Fabs connected via a disulfide bond in a hinge region; Fv composed of VL and VH; a single-chain antibody, scFv, having VL and VH connected via an artificial polypeptide linker; and a bispecific antibody such as diabody, an scDb, a tandem scFv, and a leucine zipper type one.

An anti-podoplanin antibody according to one aspect of the present invention recognizes, as an epitope, any of the following regions in the amino acid sequence of podoplanin represented by SEQ ID NO: 1:
  (i) from positions 56 to 80;
  (ii) from positions 81 to 103;
  (iii) from positions 81 to 88; and
  (iv) from positions 25 to 57.

Figure 2A:
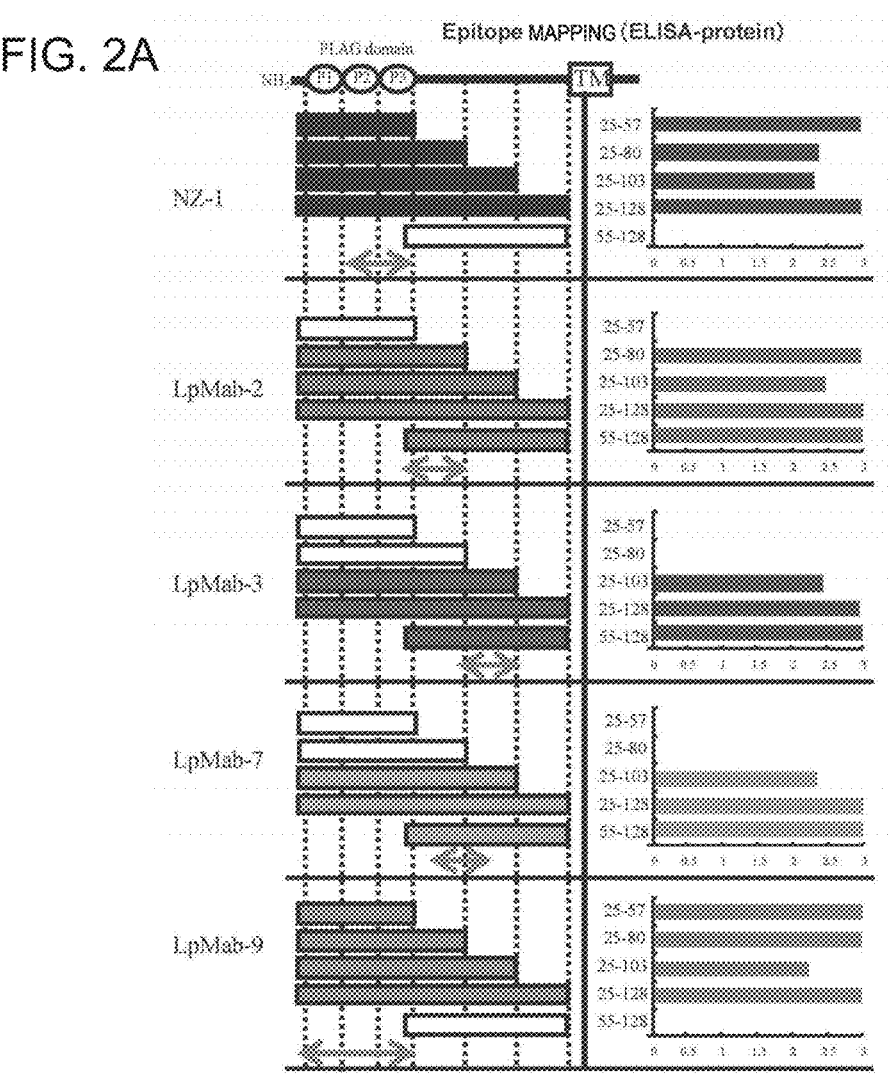
FIG. 2A shows the results of epitope analysis of five anti-podoplanin antibodies (NZ-1, LpMab-2, LpMab-3, LpMab-7, and LpMab-9) by using various recombinant proteins.
Figure 2B:
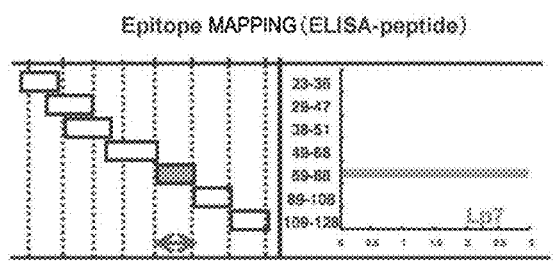
FIG. 2B shows the results of epitope analysis of LpMab-7 by using various synthetic peptides.
Figure 2C:
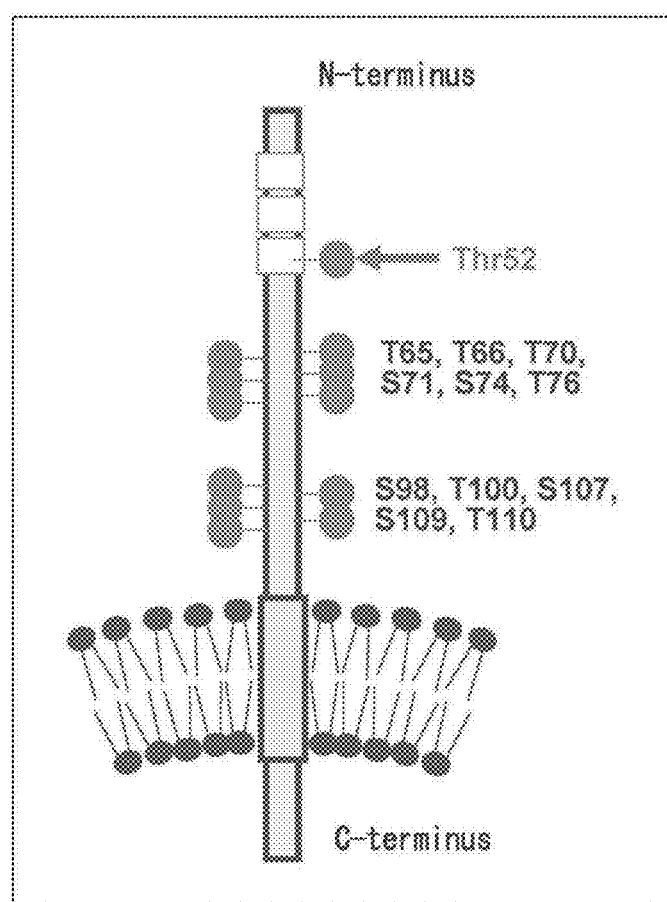
FIG. 2C is a schematic view showing an addition site of an O-linked sugar chain to human podoplanin.

As shown in FIG. 2C, an O-linked sugar chain has been added to the regions (i), (ii), and (iv) of podoplanin. This means that the anti-podoplanin antibody having an epitope in these regions may be an antibody that recognizes both a peptide and a sugar chain while containing them in the epitope.

Podoplanin has, in the region (iii) thereof, no sugar chain but, as described later in Example, an antibody having an epitope in this region detects podoplanin having the molecular weight which has not been recognized by conventionally existing antibodies. This has suggested that an anti-podoplanin antibody that recognizes podoplanin having a different molecular weight recognizes podoplanin having a molecular weight or steric structure changed by post-translational modification such as glycosylation.

An anti-podoplanin antibody according to one aspect of the present invention has at least one of the following six CDRs. These CDRs have a CDR sequence of LpMab-2.

```
                                         (SEQ ID NO: 2)
a heavy chain CDR1: GYTFTSYTIH;

(SEQ ID NO: 3)
a heavy chain CDR2: YINPGSGYTNYNEKFQD;

(SEQ ID NO: 4)
a heavy chain CDR3: WDRGY;

(SEQ ID NO: 5)
a light chain CDR1: RSSQTIVHSNGNTYLE;

(SEQ ID NO: 6)
a light chain CDR2: KVSNRFS;
and (SEQ ID NO: 7)
a light chain CDR3: FQGSHVPYT.
```

An anti-podoplanin antibody according to one aspect of the present invention has at least one of the following six CDRs. These CDRs have a CDR sequence of LpMab-3.

```
                                         (SEQ ID NO: 8)
a heavy chain CDR1: GFTFTRYAMS;

(SEQ ID NO: 9)
a heavy chain CDR2: TISNGGSYTYYLDSVKG;

(SEQ ID NO: 10)
a heavy chain CDR3: REGGQAGPAWFVY;

(SEQ ID NO: 11)
a light chain CDR1: KSSQSLLNSSNQKNYLA;

(SEQ ID NO: 12)
a light chain CDR2: FASTRES;
and (SEQ ID NO: 13)
a light chain CDR3: QQYYSTPPT.
```

An anti-podoplanin antibody according to one aspect of the present invention has at least one of the following six CDRs. These CDRs have a CDR sequence of LpMab-7.

```
                                         (SEQ ID NO: 14)
a heavy chain CDR1: GFTFSGFGMH;

(SEQ ID NO: 15)
a heavy chain CDR2: YISSVSSRIYYADTVKG;

(SEQ ID NO: 16)
a heavy chain CDR3: EQTGPAWFAY;

(SEQ ID NO: 17)
a light chain CDR1: RSSRNIVQSTGNTYLE;

(SEQ ID NO: 18)
a light chain CDR2: KVSNRFS;
and (SEQ ID NO: 19)
a light chain CDR3: FQGSHVPPVVT.
```

An anti-podoplanin antibody according to one aspect of the present invention has at least one of the following six CDRs. These CDRs have a CDR sequence of LpMab-9.

```
a heavy chain CDR1: GYTFTKSGMQ;
                                         (SEQ ID NO: 20)

(SEQ ID NO: 21)
a heavy chain CDR2: WINTHSGVPKYAEDFKG;

(SEQ ID NO: 22)
a heavy chain CDR3: WGGDGAMDY;

(SEQ ID NO: 23)
a light chain CDR1: KSSQSLLKSSSQKNYLA;

(SEQ ID NO: 24)
a light chain CDR2: FASTRES;
and (SEQ ID NO: 25)
a light chain CDR3: QQHYSAPLS.
```

In the above aspects of the anti-podoplanin antibody, the anti-podoplanin antibodies of the present invention may contain any number of CDRs selected from the six CDRs insofar as they produce the advantage of the present invention. Examples include 2 or more, 3 or more, 4 or more, 5 or more, and 6.

In each of the above aspects, at least one of the heavy chains CDR1 to 3 and the light chains CDR1 to 3 may contain addition, substitution, or deletion of one to several amino acids.

In the present specification, the term "amino acid" is used in its broadest meaning and it embraces not only naturally occurring amino acids but also artificial amino acid variants and derivatives of them. The amino acids may be represented by a commonly used single-letter or three-letter code. Examples of the amino acid or derivatives thereof used herein include naturally occurring proteinogenic L-amino acids, non-naturally occurring amino acids, and chemically synthesized compounds having properties known in the art as characteristics of an amino acid. Examples of the non-naturally occurring amino acids include, but are not limited to, α,α-disubstituted amino acids (such as α-methylalanine), N-alkyl-α-amino acids, D-amino acids, β-amino acids, and α-hydroxy acids, each having a main chain structure different from that of naturally occurring amino acids; amino acids (such as norleucine and homohistidine) having a side-chain structure different from that of naturally occurring amino acids; amino acids (such as "homo" amino acids, homophenylalanine, and homohistidine) having extra methylene in the side chain thereof; and amino acids (such as cysteic acid) obtained by substituting a carboxylic acid functional group in the side chain by a sulfonic acid group.

When the expression "having addition, substitution, or deletion of one to several amino acids" is used herein, the number of amino acids to be deleted, substituted, or the like is not particularly limited insofar as the resulting polypeptide retains its function as a CDR. The number of amino acids is set at 1, 2, 3, or 4. The amino acid to be substituted or added may be, as well as a naturally-occurring proteinogenic amino acid, a non-naturally-occurring amino acid or an amino acid analog. The position of deletion, substitution, or addition of the amino acid may be any site of an original CDR sequence insofar as the function as a CDR is retained.

In each of the above aspects of the anti-podoplanin antibody, at least one of the heavy chains CDR1 to 3 and the light chains CDR 1 to 3 may have an amino acid sequence having 80% or more identity with the amino acid sequence of the original heavy chains CDR1 to 3 and light chains CDR 1 to 3.

The term "having 80% or more identity" as used herein means that when two polypeptides having an original sequence and a mutated sequence, respectively, are aligned so that their amino acid sequences show the maximum identity, the number of amino acid residues which they have in common is 80% or more of the number of amino acids of the original sequence.

The identity is not limited insofar as it is 80% or more and the function as a CDR can be retained. It can be set at, for example, 85% or more, 90% or more, 95% or more, 98% or more, or 99% or more.

A CDR composed of an amino acid sequence obtained by adding, substituting, or deleting an amino acid from the amino acid sequence of the heavy chains CDR1 to 3 and the light chains CDR1 to 3, or a CDR having 80% or more sequence identity with the amino acid sequence of the heavy chains CDR1 to 3 and the light chains CDR1 to 3 may be prepared using a known method such as site-specific mutagenesis, random mutagenesis, chain shuffling, or CDR walking. It is well known to those skilled in the art that when the above method is used, a CDR with more mature affinity may be obtained by presenting an antibody or antibody fragment having, in the CDR thereof, a variety of mutations on a phage surface by phage display, followed by screening using an antigen (e.g., Wu et al., PNAS, 95:6037-6042 (1998); Schier, R. et al., J. Mol. Bio. 263:551-567 (1996); Schier, R. et al., J. Mol. Biol. 255:28-43 (1996); Yang, W. P. et al., J. Mol. Biol., 254:392-403 (1995)).

An anti-podoplanin antibody according to another aspect of the present invention includes:
  a heavy chain having an amino acid sequence represented by SEQ ID NO: 26 or 63;
  a heavy chain having an amino acid sequence having, in the amino acid sequence represented by SEQ ID NO: 26 or 63, addition, substitution, or deletion of one to several amino acids; or
  a heavy chain having an amino acid sequence having 80% or more identity with the amino acid sequence represented by SEQ ID NO: 26 or 63.

The amino acid sequence represented by SEQ ID NO: 26 is an amino acid sequence of the heavy chain of LpMap-2 and the amino acid sequence represented by SEQ ID NO: 63 is an amino acid sequence of the chimeric heavy chain of LpMab-2.

When the expression "addition, substitution, or deletion of one to several amino acids in the amino acid sequence of the heavy chain or light chain" is used herein, the number of amino acids to be added, substituted, or deleted can be set at, for example, 1, 2, 3, 4, 5, 6, 7, 8, 9, or 10. Other terms have the same meaning as described above.

An anti-podoplanin antibody according to a further aspect of the present invention has:
  a light chain having an amino acid sequence represented by SEQ ID NO: 27;
  a light chain having an amino acid sequence having, in the amino acid sequence represented by SEQ ID NO: 27, addition, substitution, or deletion of one to several amino acids; or
  a light chain having an amino acid sequence having 80% or more identity with the amino acid sequence represented by SEQ ID NO: 27.

The amino acid sequence represented by SEQ ID NO: 27 is an amino acid sequence of the light chain of LpMab-2.

The anti-podoplanin of the present invention may include:
  the heavy chain having an amino acid sequence represented by SEQ ID NO: 26 or 63, the heavy chain having an amino acid sequence having, in the amino acid sequence represented by SEQ ID NO: 26 or 63, addition, substitution, or deletion of one to several amino acids, or the heavy chain having an amino acid sequence having 80% or more identity with an amino acid sequence represented by SEQ ID NO: 26 or 63; and the light chain having an amino acid sequence represented by SEQ ID NO: 27, the light chain having an amino acid sequence having, in the amino acid sequence represented by SEQ ID NO: 27, addition, substitution, or deletion of one to several amino acids, or the light chain having an amino acid sequence having 80% or more identity with the amino acid sequence represented by SEQ ID NO: 27.

An anti-podoplanin antibody according to a still further aspect of the present invention includes:
  a heavy chain having an amino acid sequence represented by SEQ ID NO: 28 or 65,
  a heavy chain having an amino acid sequence having, in the amino acid sequence represented by SEQ ID NO: 28 or 65, addition, substitution, or deletion of one to several amino acids, or
  a heavy chain having an amino acid sequence having 80% or more identity with the amino acid sequence represented by SEQ ID NO: 28 or 65.

The amino acid sequence represented by SEQ ID NO: 28 is an amino acid sequence of the heavy chain of LpMab-3 and the amino acid sequence represented by SEQ ID NO: 65 is an amino acid sequence of the chimeric heavy chain of LpMab-3.

An anti-podoplanin antibody according to a still further aspect of the present invention includes:
  a light chain having an amino acid sequence represented by SEQ ID NO: 29;
  a light chain having an amino acid sequence having, in the amino acid sequence represented by SEQ ID NO: 29, addition, substitution, or deletion of one to several amino acids; or
  a light chain having an amino acid sequence having 80% or more identity with the amino acid sequence represented by SEQ ID NO: 29.

The amino acid sequence represented by SEQ ID NO: 29 is an amino acid sequence of the light chain of LpMab-3.

An anti-podoplanin antibody according to a still further aspect of the present invention may include:
  the heavy chain having an amino acid sequence represented by SEQ ID NO: 28 or 65, the heavy chain having an amino acid sequence having, in the amino acid sequence represented by SEQ ID NO: 28 or 65, addition, substitution, or deletion of one to several amino acids, or the heavy chain having an amino acid sequence having 80% or more identity with the amino acid sequence represented by SEQ ID NO: 28 or 65; and
  the light chain having an amino acid sequence represented by SEQ ID NO: 29, the light chain having an amino acid sequence having, in the amino acid sequence represented by SEQ ID NO: 29, addition, substitution, or deletion of one to several amino acids; or the light chain having an amino acid sequence having 80% or more identity with the amino acid sequence represented by SEQ ID NO: 29.

An anti-podoplanin antibody according to a still further aspect of the present invention includes:
  a heavy chain having an amino acid sequence represented by SEQ ID NO: 30 or 67;
  a heavy chain having an amino acid sequence having, in the amino acid sequence represented by SEQ ID NO: 30 or 67, addition, substitution, or deletion of one to several amino acids; or
  a heavy chain having an amino acid sequence having 80% or more identity with the amino acid sequence represented by SEQ ID NO: 30 or 67.

The amino acid sequence represented by SEQ ID NO: 30 is an amino acid sequence of the heavy chain of LpMab-7 and the amino acid sequence represented by SEQ ID NO: 67 is an amino acid sequence of the chimeric heavy chain of LpMab-7.

An anti-podoplanin antibody according to a still further aspect of the present invention includes:
  a light chain having an amino acid sequence represented by SEQ ID NO: 31;
  a light chain having an amino acid sequence having, in the amino acid sequence represented by SEQ ID NO: 31, addition, substitution, or deletion of one to several amino acids; or
  a light chain having an amino acid sequence having 80% or more identity with the amino acid sequence represented by SEQ ID NO: 31.

The amino acid sequence represented by SEQ ID NO: 31 is an amino acid sequence of the light chain of LpMab-7.

An anti-podoplanin antibody according to a still further aspect of the present invention may include:
  the heavy chain having an amino acid sequence represented by SEQ ID NO: 30 or 67, the heavy chain having an amino acid sequence having, in the amino acid sequence represented by SEQ ID NO: 30 or 67, addition, substitution, or deletion of one to several amino acids, or the heavy chain having an amino acid sequence having 80% or more identity with the amino acid sequence represented by SEQ ID NO: 30 or 67; and
  the light chain having an amino acid sequence represented by SEQ ID NO: 31, the light chain having an amino acid sequence having, in the amino acid sequence represented by SEQ ID NO: 31, addition, substitution, or deletion of one to several amino acids, or the light chain having an amino acid sequence having 80% or more identity with the amino acid sequence represented by SEQ ID NO: 31.

An anti-podoplanin antibody according to a still further aspect of the present invention includes:
  a heavy chain having an amino acid sequence represented by SEQ ID NO: 32 or 69;
  a heavy chain having an amino acid sequence having, in the amino acid sequence represented by SEQ ID NO: 32 or 69, addition, substitution, or deletion of one to several amino acids; or
  a heavy chain having an amino acid sequence having 80% or more identity with the amino acid sequence represented by SEQ ID NO: 32 or 69.

The amino acid sequence represented by SEQ ID NO: 32 is an amino acid sequence of the heavy chain of LpMab-9 and the amino acid sequence represented by SEQ ID NO: 69 is an amino acid sequence of the chimeric heavy chain of LpMab-9.

An anti-podoplanin antibody according to a still further aspect of the present invention includes:
  a light chain having an amino acid sequence represented by SEQ ID NO: 33;

a light chain having an amino acid sequence having, in the amino acid sequence represented by SEQ ID NO: 33, addition, substitution, or deletion of one to several amino acids; or a light chain having an amino acid sequence having 80% or more identity with the amino acid sequence represented by SEQ ID NO: 33.

The amino acid sequence represented by SEQ ID NO: 33 is an amino acid sequence of the light chain of LpMab-9.

An anti-podoplanin antibody according to a still further aspect of the present invention may include:

the heavy chain having an amino acid sequence represented by SEQ ID NO: 32 or 69, the heavy chain having an amino acid sequence having, in the amino acid sequence represented by SEQ ID NO: 32 or 69, addition, substitution, or deletion of one to several amino acids, or the heavy chain having an amino acid sequence having 80% or more identity with the amino acid sequence represented by SEQ ID NO: 32 or 69; and the light chain having an amino acid sequence represented by SEQ ID NO: 33, the light chain having an amino acid sequence having, in an amino acid sequence represented by SEQ ID NO: 33, addition, substitution, or deletion of one to several amino acids, or the light chain having an amino acid sequence having 80% or more identity with an amino acid sequence represented by SEQ ID NO: 33.

The anti-podoplanin antibody according to the present invention may be an antibody having one or more N-linked sugar chains bound to the Fc region thereof and having no fucose bound to N-acetylglucosamine at reducing ends of the N-linked sugar chains.

For example, the Fc region of an IgG antibody has therein two binding sites of an N-linked sugar chain, to which sites complex-type sugar chains are bound to. The term "N-linked sugar chain" means a sugar chain to be bound to Asn of an Asn-X-Ser/Thr sequence and has a common structure Man$_3$GlcNAc$_2$-Asn. It is classified into a high mannose type, a hybrid type, a complex type, and the like, depending on the kind of the sugar chain bound to two mannoses (Man) at the non-reducing end.

Although fucose may be bound to N-acetylglucosamine (GlcNAc) at the reducing end of an N-linked sugar chain, it is known that when fucose is not bound thereto, compared with when fucose is bound thereto, ADCC activity shows a remarkable increase. This is described in, for example, the pamphlet of WO2002/031140, the disclosure of which is incorporated by reference herein in its entirety.

Since a remarkable improvement in ADCC activity may lead to a reduction of a dose when an antibody is used as a drug, adverse side effects can be alleviated and at the same time, medical expenses can be reduced.

The anti-podoplanin antibody of the present invention may be used after a substance having an anti-cancer activity is bound thereto.

The term "substance having an anti-cancer activity" as used herein means a substance which causes at least one of reduction (retardation or stopping) of a tumor size, inhibition of tumor metastasis, inhibition (retardation or stopping) of tumor growth, and alleviation of one or plural symptoms associated with cancer. Specific examples include, but are not limited to, toxins, anti-cancer agents, and radioisotopes.

Examples of a toxin having an anti-cancer activity include *Pseudomonas* exotoxin (PE) or a cytotoxic fragment thereof (for example, PE38), a diphtheria toxin, and ricin A. The toxin having an anti-cancer activity exhibits toxicity only to cells into which the toxin is incorporated together with the anti-podoplanin antibody, that is, cancer cells expressing podoplanin so that it has an advantage of specifically producing an effect without adversely affecting cells around them. In particular, the anti-podoplanin antibody of the present invention is useful because it specifically binds to anti-podoplanin that is expressed in tumor cells.

Examples of the anti-cancer agent include low molecular weight compounds such as adriamycin, daunomycin, mitomycin, cisplatin, vincristine, epirubicin, methotrexate, 5-fluorouracil, aclacinomycin, nitrogen mustards, cyclophosphamide, bleomycin, daunorubicin, doxorubicin, vincristine, vinblastine, vindesine, tamoxifen, and dexamethasone, and proteins such as cytokines activating immunocompetent cells (for example, human interleukin 2, human granulocyte-macrophage colony-stimulating factor, human macrophage colony-stimulating factor, and human interleukin 12).

Examples of the radioisotope having an anti-cancer activity include $^{32}$P, $^{14}$C, $^{125}$I, $^3$H, $^{131}$I, $^{211}$At, and $^{90}$Y. The radioisotope also exhibits toxicity to cells around cells to which the anti-podoplanin antibody binds, that is, podoplanin expression cells. In general, cancer cells are not uniform and podoplanin is not expressed in every cancer cell so that radioisotopes are useful for killing podoplanin-negative cancer cells around them. Further, when a radioisotope is bound, the anti-podoplanin antibody may be a low molecular weight antibody such as Fab or scFv.

The substance having an anti-cancer activity may be directly bound to the anti-podoplanin antibody by a known method. It may be bound to the anti-podoplanin antibody after enclosed in a carrier such as liposome.

When the substance having an anti-cancer activity is a protein or a polypeptide, the substance having an anti-cancer activity may be expressed as a fusion protein with the anti-podoplanin antibody by linking a nucleic acid (which will be described later) encoding the anti-podoplanin antibody of the present invention and DNA encoding the substance having an anti-cancer activity and then inserting it into an appropriate expression vector.

(Nucleic Acid)

The present invention embraces a nucleic acid encoding the anti-podoplanin antibody of the present invention. The nucleic acid may be either a naturally occurring nucleic acid or an artificial nucleic acid. Examples include, but are not limited to, DNA, RNA, and a chimera of DNA and RNA. The base sequence of the nucleic acid encoding the anti-podoplanin antibody can be determined by a method known to those skilled in the art or a method based thereon and prepared by a known method or a method based thereon.

Examples of the nucleic acid encoding the anti-podoplanin antibody of the present invention include, but are not limited to, DNA encoding the heavy chain of LpMab-2 represented by SEQ ID NO: 34, DNA encoding the light chain of LpMab-2 represented by SEQ ID NO: 35, DNA encoding the heavy chain of LpMab-3 represented by SEQ ID NO: 36, DNA encoding the light chain of LpMab-3 represented by SEQ ID NO: 37, DNA encoding the heavy chain of LpMab-7 represented by SEQ ID NO: 38, DNA encoding the light chain of LpMab-7 represented by SEQ ID NO: 38, DNA encoding the heavy chain of LpMab-9 represented by SEQ ID NO: 39, and DNA encoding the light chain of LpMab-9 represented by SEQ ID NO: 39.

The nucleic acids encoding respective CDRs of LpMab-2, LpMab-3, LpMab-7, and LpMab-9 are included in the DNA sequences represented by these SEQ ID NOS.

(Expression Vector)

The present invention also embraces an expression vector containing the nucleic acid encoding the anti-podoplanin antibody of the present invention. The expression vector can be selected as needed according to a host cell to be used. Examples include a plasmid, a retrovirus vector, an adenovirus vector, an adeno-associated virus (AAV) vector, a plant virus vector such as cauliflower mosaic virus vector or tobacco mosaic virus vector, a cosmid, a YAC, and an EBV-derived episome. The nucleic acid encoding the anti-podoplanin antibody of the present invention may be inserted into these expression vectors by a known method (such as a method using a restriction enzyme).

The expression vector of the present invention may further contain a promoter for controlling the expression of an antibody gene, a replication origin, a selection marker gene, or the like. The promoter and the replication origin may be selected as needed, depending on the nature of the host cell and vector.

(Transformant)

The present invention embraces a transformant containing the vector of the present invention. The transformant can be obtained by transfecting the vector of the present invention into appropriate host cells. Examples of the usable host cells include eukaryotic cells such as mammalian cells (CHO cells, COS cells, myeloma cells, HeLa cells, Vero cells, and the like), insect cells, plant cells, and fungus cells (*Saccharomyces, Aspergillus*, and the like), and prokaryotic cells such as *Escherichia coli* (*E. coli*) and *Bacillus subtilis*.

(Production Method of Antibody)

Although no limitation is imposed on the production method of the anti-podoplanin antibody of the present invention, an anti-podoplanin monoclonal antibody can be obtained, for example, by isolating antibody producing cells from a non-human mammal immunized with podoplanin or a fragment thereof, fusing them with myeloma cells or the like to obtain hybridomas, and purifying an antibody produced by the hybridomas. An anti-podoplanin polyclonal antibody can be obtained from the serum of an animal immunized with podoplanin or fragment thereof. The anti-podoplanin antibody of the present invention may be obtained using sugar chain-added podoplanin when a non-human animal is immunized.

When the anti-podoplanin antibody of the present invention is produced using genetic recombination, it may be produced, for example, by transforming a proper host with an expression vector containing the nucleic acid of the present invention, culturing the resulting transformant under appropriate conditions to express an antibody, and then isolating and purifying the antibody by a known method.

Examples of the isolating and purifying method include an affinity column using protein A or the like, another chromatography column, a filter, ultrafiltration, salting-out, and dialysis. These methods may be used in combination as needed.

An antibody that binds to a predetermined epitope sequence can be prepared using a method known to those skilled in the art or a method based thereon. For example, a peptide containing an epitope sequence is fixed to a solid phase carrier and binding between the peptide and a plurality of antibodies is detected, by which an antibody that specifically binds to the epitope can be obtained.

As the "plurality of antibodies", antibodies obtained by immunizing an animal with an antigen protein or a partial peptide thereof may be used or an antibody library or an antibody fragment library constructed by phage display may be used. When a library constructed by phage display is used, it is also possible to fix a peptide containing an epitope sequence to a solid phase carrier, repeat panning, and thereby obtain an antibody that specifically binds to the epitope.

A human chimeric antibody and a human CDR grafted antibody can be prepared by cloning an antibody gene from mRNA of hybridomas producing an antibody of an animal other than human and linking it to a portion of a human antibody gene by using genetic recombination technology.

For example, for the preparation of a human chimeric antibody, cDNA is synthesized using reverse transcriptase from mRNA of hybridomas that produce a mouse antibody, the heavy chain variable region (VH) and the light chain variable region (LH) are cloned by PCR, and then the sequence is analyzed. Next, a 5' primer containing a leader sequence is prepared from an antibody base sequence having a high identity and then a portion of the cDNA from the signal sequence to the 3' end of the variable region is cloned by PCR using the 5' primer and the variable region 3' primer. On the other hand, the constant region of the heavy chain and the light chain of human IgG1 is cloned and for the heavy chain and the light chain, the mouse antibody-derived variable region and the human antibody-derived constant region are linked to each other by Overlapping Hanging using PCR and amplified. The DNA thus obtained is inserted into an appropriate vector, followed by transformation to obtain a human chimeric antibody.

For the preparation of a CDR grafted antibody, a human antibody variable region having the highest homology with a mouse antibody variable region to be used is selected and cloned and the base sequence of CDR is altered by site-selective mutagenesis using mega-primer method. When humanization of an amino acid sequence constituting a framework region disturbs specific binding to an antigen, an amino acid of a portion of the framework may be converted from a human type to a rat type.

A CDR composed of an amino acid sequence having deletion, substitution or addition of one or two amino acids in the original amino acid sequence or a CDR composed of an amino acid sequence having X % or more identity to the original amino acid sequence may be prepared using a known method such as site-specific mutagenesis, random mutagenesis, chain shuffling, or CDR walking.

It is well known to those skilled in the art that according to these methods, a CDR having more mature affinity can be obtained by displaying an antibody or antibody fragment having a variety of mutations in CDRs on the phage surface by phage display and screening using an antigen (for example, Wu et al., PNAS, 95:6037-6042 (1998); Schier, R. et al., J. Mol. Bio. 263:551-567 (1996); Schier, R. et al., J. Mol. Biol. 255:28-43 (1996); Yang, W. P. et al., J. Mol. Biol., 254:392-403 (1995)). The present invention also embraces an antibody containing a CDR matured in such a manner.

Additional examples of the antibody production method include the Adlib system for obtaining an antibody producing line from Trichostatin A-treated chicken B cell-derived DT40 cell line (Seo, H. et al., Nat. Biotechnol., 6:731-736, 2002) and a method of preparing a human antibody by immunizing KM mice obtained by destroying the mouse antibody gene and introducing a human antibody gene (Itoh, K. et al., Jpn. J. Cancer Res., 92:1313-1321, 2001; Koide, A. et al., J. Mol. Biol., 284:1141-1151, 1998). These methods can also be applied to production of the antibody of the present invention.

The antigen binding fragment of the anti-podoplanin antibody according to the present invention may be expressed by the above-described method using DNA encoding the fragment. Alternatively, a full-length antibody is obtained and then treated with an enzyme such as papain or pepsin to fragment it.

The anti-podoplanin antibody according to the present invention may be different in amino acid sequence, molecular weight, isoelectric point, presence/absence of sugar chains, conformation or the like, depending on the preparation method or purification method. However, the antibody thus obtained is embraced in the present invention insofar as it has a function equivalent to that of the antibody of the present invention. For example, the antibody of the present invention expressed in a prokaryotic cell such as E. coli has a methionine residue at the N terminal of the amino acid sequence of the original antibody. The present invention also embraces such an antibody.

When the anti-podoplanin antibody of the present invention is an antibody having an N-linked sugar chain having no fucose bound to N-acetylglucosamine at the reducing end, such an antibody can be produced by a known method or a method based thereon. Such a method of producing an antibody is described in, for example, the pamphlet of WO2002/031140 or Japanese Patent Application Publication No. 2009-225781, the disclosure of which is incorporated herein by reference in its entirety.

Specifically, for example, an intended anti-podoplanin antibody can be obtained by transforming cells, whose enzymatic activity involved in the synthesis of GDP-fucose or α-1,6-fucosyltransferase activity has been reduced or deleted, by using a vector containing DNA encoding the anti-podoplanin antibody of the present invention, culturing the transformant thus obtained, and then purifying it. Examples of the enzyme involved in synthesis of GDP-fucose include GDP-mannose 4,6-dehydratase (GMP), GDP-keto-6-deoxymannose 3,5-epimerase, 4-reductase (Fx), and GDP-beta-L-fucose pyrophosphorylase (GFPP).

Here, the cells are not particularly limited, but are preferably mammalian cells. For example, CHO cells having the above-described enzymatic activity reduced or deleted may be used.

Although the antibody composition obtained by the above method may contain an antibody having fucose bound to N-acetylglucosamine at the reducing end, a proportion of the fucose-bound antibody is 20 wt % or less, preferably 10 wt % or less, more preferably 5 wt % or less, most preferably 3 wt % or less, each based on the total weight of the antibodies.

Further, the antibody having an N-linked sugar chain having no fucose bound to N-acetylglucosamine at the reducing end may also be obtained by introducing a vector containing DNA encoding the anti-podoplanin antibody of the present invention into insect eggs, hatching and growing the insects, and crossbreeding them if necessary to produce a transgenic insect, and extracting an anti-podoplanin antibody from the transgenic insect or a secretion thereof. As the insect, a silkworm may be used. In this case, the antibody can be extracted from silkworm cocoons.

Although the antibody composition obtained using the above method may also contain an antibody having fucose bound to N-acetylglucosamine at the reducing end, a proportion of the fucose-bound antibody is 20 wt % or less, preferably 10 wt % or less, more preferably 5 wt % or less, most preferably 3 wt % or less, each based on the total weight of the antibodies.

(Activity of the Antibody of the Present Invention)

The drug efficacy mechanism of antibody drugs is based on two biological activities of antibodies. One of them is a target antigen-specific binding activity, which is an activity neutralizing the function of a target antigen molecule through binding thereto. Functional neutralization of the target antigen molecule is exhibited through the Fab region.

The other one is a biological activity of an antibody called "effector activity". The effector activity is exhibited as antibody-dependent cellular cytotoxicity (ADCC), complement-dependent cytotoxicity (CDC), direct induction of apoptosis, or the like through an Fc region of an antibody.

The activities of the anti-podoplanin antibody of the present invention can be measured in the following methods.

(1) Binding Activity

The binding activity of an antibody can be measured by a known method, for example, ELISA (enzyme-linked immunosorbent assay), EIA (enzyme immunoassay), RIA (radioimmunoassay), a fluorescent antibody method, or an FACS method.

(2) ADCC Activity

The term "ADCC activity" means a target cell damaging activity by, when the antibody of the present invention binds to the cell surface antigen of target cells, Fcγ receptor-bearing cells (effector cells) bound to the Fc portion of the antibody through its Fcγ receptor.

The ADCC activity can be known by mixing podoplanin-expressing target cells, effector cells, and the antibody of the present invention, and measuring the degree of ADCC. As the effector cells, for example, mouse splenocytes, or monocytes isolated from the human peripheral blood or bone marrow may be used. As the target cells, for example, podoplanin-positive mesothelioma cells or podoplanin-positive glioblastoma cells may be used. The activity can be measured by labeling target cells with $^{51}$Cr or the like in advance, adding the antibody of the present invention to the resulting cells, incubating the resulting mixture, adding effector cells to the target cells at a ratio adequate therefor, incubating the resulting mixture, collecting the supernatant, and then counting the label in the supernatant.

(3) CDC Activity

The term "CDC activity" means cellular cytotoxicity caused by a complement system.

The CDC activity can be measured as in the ADCC activity test except for the use of a complement instead of effector cells (4) Tumor Growth Inhibitory Activity The tumor growth inhibitory activity can be measured using a tumor model animal. For example, a tumor is subcutaneously implanted into a mouse and the antibody of the present invention is administered thereto. A tumor growth inhibitory effect can be measured by comparing the volume of the tumor tissue between a non-administered group and an administered group.

The tumor growth inhibitory activity in the present invention may result from inhibition of growth of individual cells or may result from induction of apoptosis.

(Pharmaceutical Composition)

The anti-podoplanin antibody of the present invention may be used for prevention or treatment of a tumor that expresses a podoplanin antibody. A pharmaceutical composition according to one aspect of the present invention contains the anti-podoplanin antibody or antigen-binding fragment of the present invention as an effective ingredient and further contains a pharmacologically acceptable carrier or additive.

The anti-podoplanin antibody of the present invention may be used for delivery of a drug targeting tumor cells. A pharmaceutical composition according to another aspect of the present invention contains, as an effective ingredient, the anti-podoplanin antibody or antigen-binding fragment thereof to which the substance having anti-cancer activity has been bound and it further contains a pharmacologically acceptable carrier or additive.

Examples of the carrier and additive include, but are not limited to, water, saline, phosphate buffer, dextrose, pharmaceutically acceptable organic solvents such as glycerol and ethanol, collagen, polyvinyl alcohol, polyvinylpyrrolidone, carboxy vinyl polymers, carboxymethylcellulose sodium, sodium polyacrylate, sodium alginate, water-soluble dextran, sodium carboxymethyl starch, pectin, methylcellulose, ethylcellulose, xanthan gum, gum arabic, casein, agar, polyethylene glycol, diglycerin, glycerin, propylene glycol, petrolatum, paraffin, stearyl alcohol, stearic acid, human serum albumin, mannitol, sorbitol, lactose, and surfactants.

The pharmaceutical composition of the present invention may be provided in a variety of forms, for example, a solution (for example, an injection), a dispersion, a suspension, a tablet, a pill, a powder, or a suppository. A preferred aspect is an injection and parenteral administration (for example, intravenous, transdermal, intraperitoneal, or intramuscular administration) is preferred.

The pharmaceutical composition of the present invention is therapeutically effective for podoplanin-related diseases, for example, tumors, thrombosis, and arteriosclerosis.

It has been suggested that podoplanin causes platelet aggregation through binding thereof to CLEC-2. Further, it has been reported that CLEC-2, which is a receptor of podoplanin on platelets, is involved in thrombosis/arteriosclerosis, specifically, CLEC-2-deficient platelets are inferior in aggregation capacity both in vitro and in vivo, and CLEC-2 deficiency prolongs the bleeding time, thereby preventing occlusive arterial thrombus formation (May, F. et al., Blood 2009; 114(16: 3464-72).

Further, it has also been reported that high expression of podoplanin is found in an arteriosclerotic lesion (Patent Document 1). These facts have strongly suggested that the pharmaceutical composition of the present invention is therapeutically effective for thrombosis or arteriosclerosis.

Meanwhile, examples of podoplanin-related tumors include brain tumor, mesothelioma, testicular tumor, ovarian cancer, and squamous cell cancer. The squamous cell cancer includes, but is not limited to, oral cancer, pharyngeal cancer, laryngeal cancer, esophageal cancer, lung cancer, skin cancer, and uterine cervical cancer.

The present invention also embraces a method of treating a podoplanin-related disease, including administering a therapeutically effective amount of the antibody of the present invention.

The term "therapeutically effective amount" as used herein means an amount of an active substance capable of alleviating one or more symptoms of a disease to be treated to a certain extent. For an anti-cancer agent, it means an amount that causes at least one of reduction of a tumor size, inhibition (retardation or stopping) of tumor metastasis, inhibition of tumor growth (retardation or stopping), and alleviation of one or more symptoms associated with cancer.

Specifically, the dose of the antibody of the present invention may be in a range of, for example, from 0.025 to 50 mg/kg, preferably from 0.1 to 50 mg/kg, more preferably from 0.1 to 25 mg/kg, still more preferably from 0.1 to 10 mg/kg or from 0.1 to 3 mg/kg, but is not limited thereto.

(Marker and Diagnostic Agent)

As described above, podoplanin is highly expressed in certain tumor cells. The anti-podoplanin antibody of the present invention is therefore useful in the diagnosis of cancer, particularly of cancer in which podoplanin is highly expressed, such as brain tumor, mesothelioma, testicular tumor, ovarian cancer, and a variety of squamous cell cancers (oral cancer, pharyngeal cancer, laryngeal cancer, esophageal cancer, lung cancer, skin cancer, and uterine cervical cancer). The anti-podoplanin antibody of the present invention specifically binds to tumor cells so that it is particularly useful for diagnosis.

Further, it has been verified that podoplanin is highly expressed in an arteriosclerotic lesion and the anti-podoplanin antibody of the present invention is therefore also useful in the diagnosis of arteriosclerosis.

In an arteriosclerotic lesion, high expression of podoplanin was observed in a macrophage exudate lesion among early lesions. Since the macrophage exudate lesion has been known to easily become an advanced lesion, early detection of arteriosclerosis which is likely to lead to an advanced lesion is expected by a diagnostic method through the detection of podoplanin.

Therefore, the present invention also embraces a diagnostic agent of cancer or arteriosclerosis containing the antibody of the present invention, use of the antibody for the diagnosis of cancer or arteriosclerosis, and a diagnostic method of cancer or arteriosclerosis using the antibody of the present invention.

All the disclosed patent documents and non-patent documents to be cited herein are incorporated herein as an entirety by reference.

EXAMPLES

The present invention will hereinafter be described specifically based on embodiments. The present invention is not limited to or by them. Those skilled in the art can change the present invention into various aspects without departing from the gist of the present invention. Such a change is also embraced within the scope of the present invention.

1. Preparation of Anti-Podoplanin Antibody

Balb/c mice were immunized four times (once a week) with a cancer cell line in which full-length human podoplanin had been forcibly expressed and an antibody reactive with a recombinant protein purified from the cancer cell line was screened using ELISA (Enzyme-linked immunosorbent assay).

ELISA was performed in the following manner: The recombinant protein (1µ/ml) was immobilized on a 96 well plate (Nunc MaxiSorp; product of Thermo Fisher) at 37 degrees for 30 minutes, followed by blocking at 37 degrees for 30 minutes using SuperBlock/PBST (product of Thermo Fisher). Similarly, the culture supernatant and anti-mouse IgG-HRP (product of Dako) were reacted successively at 37 degrees for 30 minutes and its color was developed using TMB-Ultra (product of Thermo Fisher). Absorbance measurement (OD: 655 nm) was performed using a microplate reader (product of Bio-rad).

Secondary screening was performed using western blotting and four antibodies (LpMab-2, LpMab-3, LpMab-7, and LpMab-9) reactive with podoplanin were established.

As a result of subclass identification, they were found to be LpMab-2 (mouse IgG1, kappa), LpMab-3 (mouse IgG1, kappa), LpMab-7 (mouse IgG1, kappa), and LpMab-9 (mouse IgG1, kappa), respectively.

2. Western Blot Analysis

Cell lysates of seven cell lines (CHO/hPDPN, Lec1/hPDPN, Lec2/hPDPN, Lec8/hPDPN, CHO, LN229/hPDPN, and LN229) were prepared and subjected to SDS-PAGE electrophoresis at 10 µg/lane. After transfer to a PVDF membrane, blocking was performed at room temperature for one hour with 4% skim milk/0.05% Tween in PBS (blocking buffer). Five anti-podoplanin antibodies (NZ-1 (rat IgG2a, kappa), LpMab-2 (mouse IgG1, kappa), LpMab-3 (mouse IgG1, kappa), LpMab-7 (mouse IgG1, kappa), and LpMab-9 (mouse IgG1, kappa)) were diluted with the blocking buffer at a concentration of 1 µg/ml and reacted at room temperature for one hour. Secondary antibodies (anti-rat IgG-HRP and anti-mouse IgG-HRP: product of Dako, 1:1000 dilution) were reacted at room temperature for 30 minutes and color was developed using ECL-plus (product of Thermo Fisher). For detection, Sayaca-imager (product of DRC) was used.

The results are shown in FIG. 1. From the conventional anti-podoplanin antibody (NZ-1), two bands (upper band (40 kDa): glycosylated one, lower band (25 kDa): unglycosylated one) are detected. Antibodies established this time show different detection patterns.

In LpMab-2, only a band of 40 kDa is detected and it does not recognize podoplanin expressed in the glycosylation deficient lines (Lec2 and Lec8), suggesting that an epitope contains a sugar chain such as sialic acid or O-linked sugar chain.

In LpMab-3, in addition to a band of 40 kDA, a band of 30 kDA which has not been detected at all in the NZ-1 antibody or other commercially available antibodies is recognized. It does not recognize podoplanin expressed in the glycosylation deficient line (Lec2), suggesting that the epitope contains sialic acid.

Three bands of 40 kDa, 30 kDa, and 25 kDa are detected by LpMab-7. The band of 30 kDA which has not been recognized by the NZ-1 antibody is detected, suggesting that it is an antibody being able to recognize various podoplanin molecules with steric structure that cannot be recognized by the NZ-1 antibody.

In LpMab-9, only a band of 40 kDa is detected and podoplanin expressed in the glycosylation deficient lines (Lec2 and Lec8) is not recognized, suggesting that the epitope contains a sugar chain such as sialic acid or O-linked sugar chain.

3. Analysis of Epitope in Antibody

The epitope in each antibody was analyzed using ELISA. ELISA was performed in the following method. Various human podoplanin-Fc chimera recombinant proteins (25-57, 25-80, 25-103, 25-128, and 55-128) (1 µg/ml) were immobilized on a 96 well plate (Nunc MaxiSorp; product of Thermo Fisher) at 37 degrees for 30 minutes. Blocking was performed at 37 degrees for 30 minutes by using SuperBlock/PBST (product of Thermo Fisher). Primary antibodies (LpMab-2, LpMab-3, LpMab-7, LpMab-9) (1 µg/ml) and anti-mouse IgG-HRP (product of Dako, 1:1000 dilution) were reacted successively at 37 degrees for 30 minutes and their color was developed using TMB-Ultra (product of Thermo Fisher). After the reaction was stopped with 2M sulfuric acid, the absorbance was measured (OD: 450 nm) by using a microplate reader (product of Bio-Rad).

The results are shown in FIG. 2. Commercially available anti-podoplanin antibodies (NZ-1, D2-40, 18H5, etc.) are antibodies against PLAG domain (from position 25 to position 57 of SEQ ID NO: 1) in a platelet aggregation region (Prior Art Document: Ogasawara et al., Hybridoma 2008).

On the other hand, it has been found that LpMab-2 contains an epitope at from position 56 to position 80 (including Thr65, Thr66, Thr70, Ser71, Ser74, and Ter76) in SEQ ID at NO: 1, LpMab-3 contains an epitope at from position 81 to position 103 (including Ser98 and Thr100) in SEQ ID NO: 1, and LpMab-9 contains an epitope at from position 25 to position 57 (including Thr52) in SEQ ID NO: 1 (FIG. 2A).

LpMab-7 reacts with human podoplanin-Fc chimera (FIG. 2A) at from position 81 to position 103 of SEQ ID NO: 1 and also with a synthetic peptide at from position 69 to position 88 (FIG. 2B), showing that it contains an epitope at from position 81 to position 88 and the epitope does not contain a sugar chain. There has never been a report on a monoclonal antibody having an epitope other than PLAG domain and is useful in western blot, flow cytometry, immunohistostaining, or the like.

The position of the epitope of each antibody in the amino acid sequence (SEQ ID NO: 1) of podoplanin is shown below with an underline.

(Epitope of LpMab-2)
mwkvsallfvlgsaslwvlaegastgqpeddtettgleggvampgaeddv vtpgt<u>sedryksglttlvatsvnsvtgiri</u>edlptsestvhaqeqspsat asnvatshstekvdgdtqttvekdglstvtlvgiivgvllaigfiggiiv vvmrkmsgrysp (Epitope of LpMab-3)
mwkvsallfvlgsaslwvlaegastgqpeddtettgleggvampgaeddv vtpgtsedryksglttlvatsvnsvtgiri<u>edlptsestvhaqeqspsat</u>

<u>asn</u>vatshstekvdgdtqttvekdglstvtlvgiivgvllaigfiggiiv vvmrkmsgrysp (Epitope of LpMab-7)
mwkvsallfvlgsaslwvlaegastgqpeddtettgleggvampgaeddv vtpgtsedryksglttlvatsvnsvtgiri<u>edlptsest</u>vhaqeqspsat asnvatshstekvdgdtqttvekdglstvtlvgiivgvllaigfiggiiv vvmrkmsgrysp (Epitope of LpMab-9)
mwkvsallfvlgsaslwvlaega<u>stgqpeddtettgleggvampgaeddv</u>

<u>vtpgtsedryksglttlvatsvnsvtgiri</u>edlptsestvhaqeqspsat asnvatshstekvdgdtqttvekdglstvtlvgiivgvllaigfiggiiv vvmrkmsgrysp The glycosylation site of human podoplanin is identified by the following method (FIG. 2C).

A recombinant protein of human podoplanin was purified from a CHO/hPDPN line and then treated with trypsin into peptide fragments. The peptide fragments were each analyzed using a peptide sequencer (product of Shimadzu Corporation) and serine (Ser) or threonine (Thr) from which no amino acid was detected was identified as a glycosylation site.

4. Flow Cytometry

Reactivity of the anti-podoplanin antibodies (LpMab-2, LpMab-3, LpMab-7, and LpMab-9) with a podoplanin expression strain was studied by flow cytometry. First, LpMab-2, LpMab-3, LpMab-7, and LpMab-9 (1 µg/ml) were each reacted at 4° C. for 30 minutes with human podoplanin-expression cell lines (lymphatic epithelial cells, renal epithelial cells (HEK-293T), mesothelial cell lines (Met-5A), podoplanin gene expression strains in various glycosylation-deficient lines of CHO cells (CHO-hPDPN (parent strain), Lec1-hPDPN (N-linked glycosylation deficiency), Lec2-hPDPN (sialic acid deficiency), and Lec8- hPDPN (O-linked glycosylation deficiency)), glioblastoma cells (LN319), podoplanin gene expression strain in squamous cell cancer cells (RERF-LC-AI-hPDPN), podoplanin gene expression strain in malignant mesothelial cells (Y-MESO14-hPDPN), and HSC3/hPDPN (oral cancer cell line)). The reaction products were each reacted further with an anti-mouse IgG-FITC antibody (product of Life Technologies) at 4° C. for 30 minutes. As a negative control, only the secondary antibody of each of them was used. Fluorescence intensity was measured using EC800 (product of Sony).

Figure 3A:
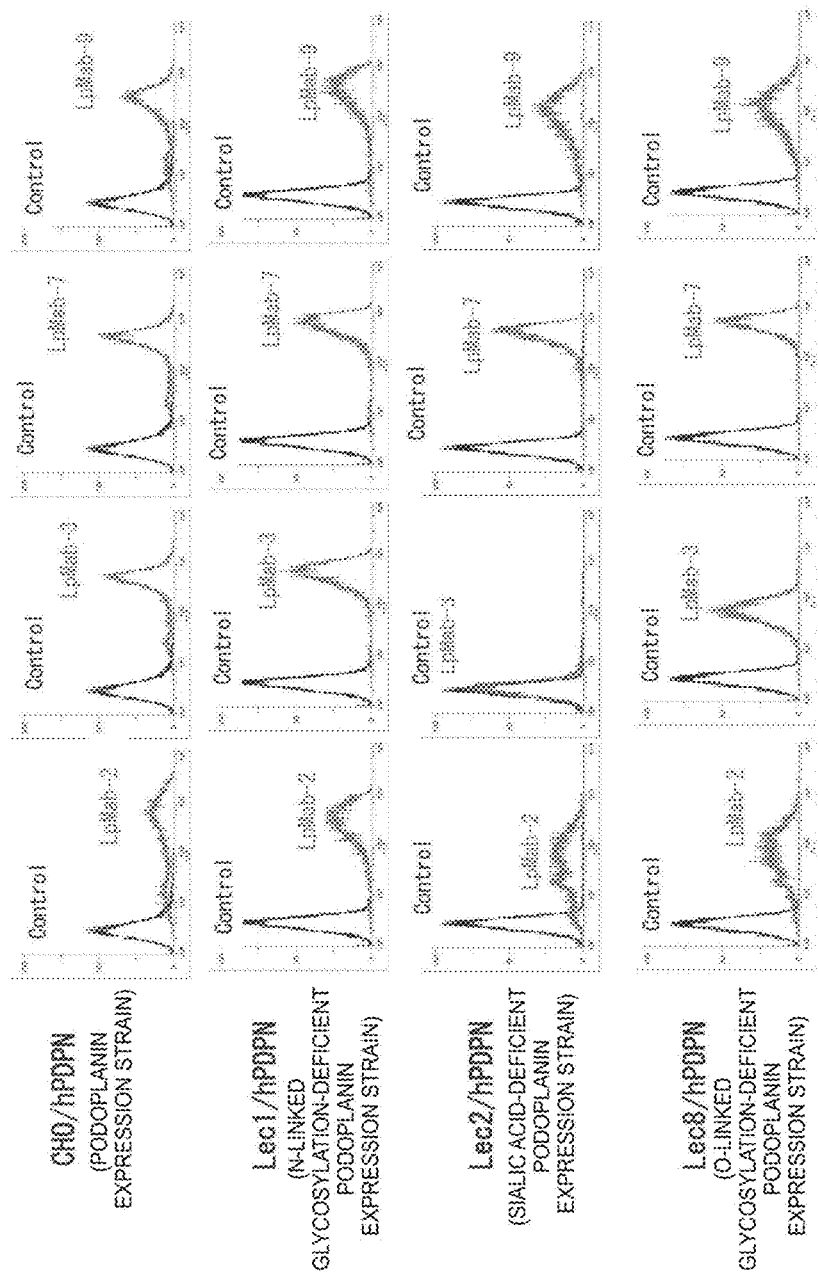
FIG. 3A shows the results of studying, by flow cytometry, reactivity of anti-podoplanin antibodies (LpMab-2, LpMab-3, LpMab-7, and LpMab-9) of the present invention with podoplanin expressed in a glycosylation deficient line of CHO.

The results are shown in FIG. 3. First, the reactivity of each antibody with podoplanin expressed in glycosylation deficient lines of CHO was studied (FIG. 3A).

LpMab-2 showed low reactivity with Lec2 and Lec8 among the glycosylation deficient lines of CHO. LpMab-3 showed low reactivity with Lec2. Lec9 showed low reactivity with Lec2 and Lec8.

Next, the reactivity of each antibody with human cancer cell lines was studied (FIG. 3B). The antibodies all showed high reactivity with podoplanin on tumor cells such as squamous cell cancer, glioblastoma, malignant mesothelioma, and oral cancer cells. On the other hand, LpMab-2 scarcely reacted with lymphatic endothelial cells, but the other antibodies all reacted therewith (FIG. 3C).

Although LpMab-2 did not react with normal renal epithelial cells (HEK-293T), the other antibodies all reacted with renal epithelial cells. Further, LpMab-2 and LpMab-9 did not react with a normal epithelial cell line (Met-5A), but LpMab-3 and LpMab-7 reacted with the epithelial cells.

Among the four antibodies used here, only LpMab-2 is a tumor-specific antibody. It is apparent that LpMab-2, LpMab-3, and LpMab-9 contain, in their epitopes, not only a peptide portion of podoplanin but also a sugar chain such as sialic acid or O-linked sugar chain. Since LpMab-9 reacts with epithelial cells but does not react with mesothelial cells, it partially shows tumor specificity.

Expression plasmids were prepared by TA cloning of the full-length H chain and L chain of LpMab-2, LpMab-3, LpMab-7, and LpMab-9 in a pcDNA3.1 vector (product of Life Technologies). The plasmids thus obtained were each introduced into a CHO cell line by lipofection to express recombinant antibodies. The recombinant antibodies (rLpMab-2, rLpMab-3, rLpMab-7, and rLpMab-9) in the culture supernatant (collected three days after gene introduction) were reacted with LN319 cells, that is, podoplanin-expression strain, at 4° C. for 30 minutes and then reacted further with an anti-mouse IgG-FITC antibody (product of Life Technologies) at 4° C. for 30 minutes. As a negative control, only a secondary antibody was used. Fluorescence intensity was measured using EC800 (product of Sony).

Figure 3D:
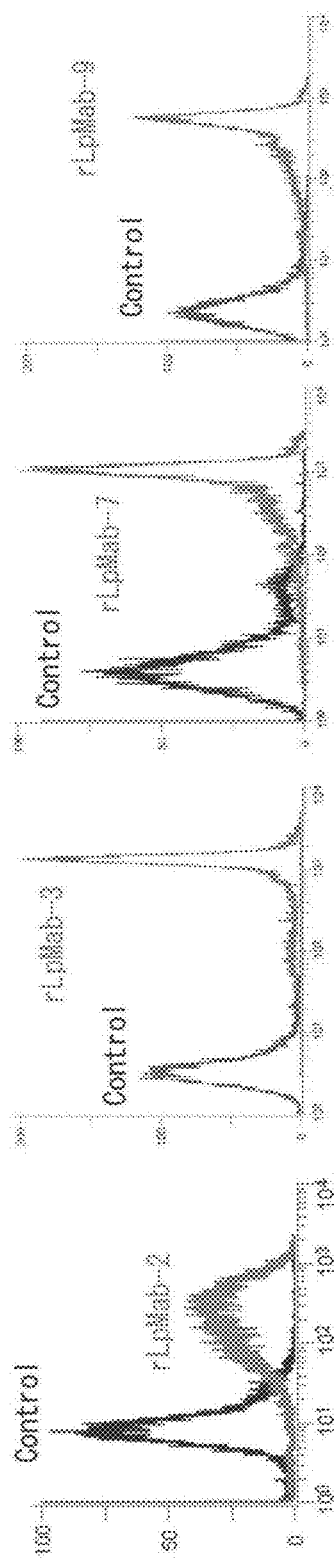
FIG. 3D shows the results of studying, by flow cytometry, the reactivity of recombinant anti-podoplanin antibodies (rLpMab-2, rLpMab-3, rLpMab-7, and rLpMab-9) of the present invention with brain tumor cell lines.

As a result, all the recombinant antibodies showed good reactivity in flow cytometry using LN319 cells (FIG. 3D). It has therefore been verified that the sequences of the H chain and the L chain of LpMab-2, LpMab-3, LpMab-7, and LpMab-9 shown in SEQ ID NOS: 26 to 41 are correct.

Further, human chimeric H chains of the variable region of the H chain of LpMab-2, LpMab-3, LpMab-7, and LpMab-9 and the constant region of a human IgG1 antibody were prepared. The chimeric H chain was prepared as follows. First, the constant region of the human IgG1 antibody was amplified using the following primer, while using a gene expression vector of the NZ-8H chain (Patent Document 1) with a template.

Primer Sequence

```
hIgG1CH1.BamHI:
                                          (SEQ ID NO: 52)
cacggaTCCACCAAGGGCCCATCGGTC hIgG1CH3-R1.NotI:
                                          (SEQ ID NO: 53)
aatgcggccgcTCATTTACCCGGAGACAGGGAG
```

For PCR reaction, QIAGEN HotStar HiFidelity DNA polymerase was used. The reaction was made under the following temperature conditions: first at 95 degrees for 5 minutes, next 35 cycles of 94 degrees for 15 seconds, 50 degrees for one minute, and 72 degrees for one minute, and then at 72° C. for 10 minutes. The amplified PCR product was purified inFastGene Gel/PCR Extraction kit and subcloned into pCAG-zeo via a BamHI-NotI restriction enzyme site. The basic sequence was determined from the vector primer. The vector was named "pCAGzeo-hIgG1h".

Variable regions of LpMab-2, LpMab-3, LpMab-7, and LpMab-9 were amplified using the following primers.

```
LpMab-2
HindIII-LpMab-2HatgS:
                                          (SEQ ID NO: 54)
ggcaagcttATGGAAAGGCACTGGATCTTT LpMab-2HVHR-BamHI:
                                          (SEQ ID NO: 55)
gccggatccTGAGGAGACTGTGAGAGTGGT LpMab-3
HindIII-LpMab-3HatgS:
                                          (SEQ ID NO: 56)
ggcaagcttATGAACTTTGTGCTCAGCTTG LpMab-3HVHR-BamHI:
                                          (SEQ ID NO: 57)
gccggatccTGCAGAGACAGTGACCAGAGT LpMab-7
HindIII-LpMab-7HatgS:
                                          (SEQ ID NO: 58)
ggcaagcttATGGACTCCAGGCTCAATTTA LpMab-7HVHR-BamHI:
                                          (SEQ ID NO: 59)
gccggatccTGCAGAGACAGTGACCAGAGT LpMab-9
HindIII-LpMab-9HatgS:
                                          (SEQ ID NO: 60)
ggcaagcttATGGAATGTCTGTGGAACTTG LpMab-9HVHR-BamHI:
                                          (SEQ ID NO: 61)
gccggatccTGAGGAGACGGTGACTGAGGT
```

The temperature conditions were set as follows: at 95° C. for 5 minutes, 35 cycles of 94 degrees for 15 seconds, 50 degrees for one minute, and 72 degrees for 1 minute, and then at 72 degrees for 10 minutes. After the amplified PCR product was purified using a FastGene Gel/PCR Extraction kit and the purified product was subcloned into a pCAGzeo-hIgG1 h vector via a HindIII-BamHI restriction enzyme site, the base sequence was determined from the vector primer.

Figure 3E:
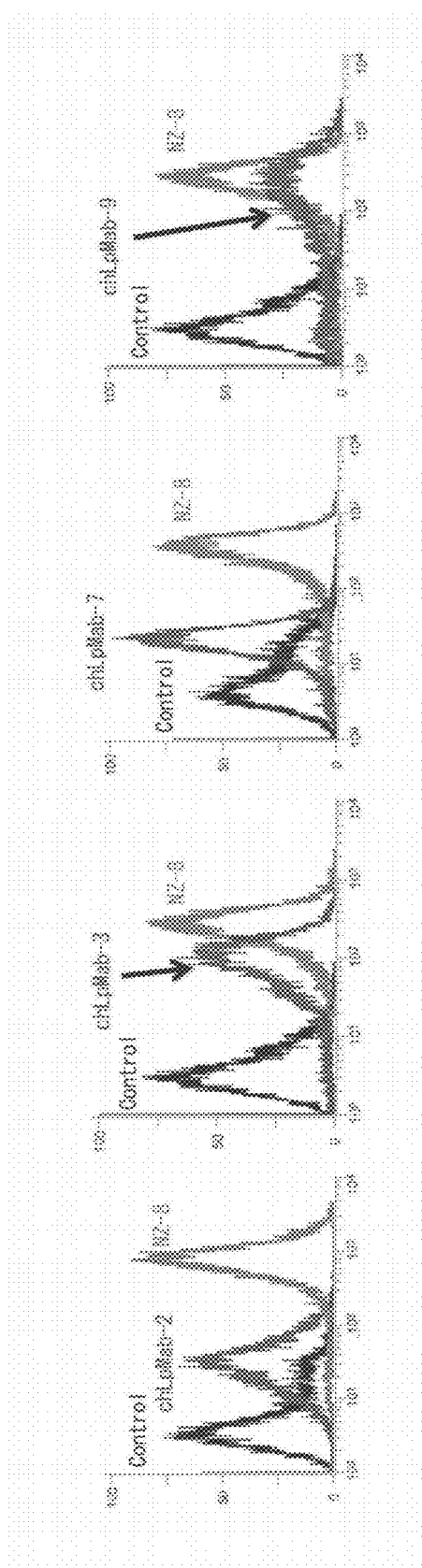
FIG. 3E shows the results of studying, by flow cytometry, the reactivity of human chimeric anti-podoplanin antibodies (chLpMab-2, chLpMab-3, chLpMab-7, and chLpMab-9) of the present invention with brain tumor cell lines.

Human chimeric antibodies (chLpMab-2, chLpMab-3, chLpMab-7, and chLpMab-9) were prepared by co-expressing combinations of the human chimeric H chain of each of LpMab-2, LpMab-3, LpMab-7, and LpMab-9 prepared above and the plasmid of mouse L chain. The amino acid sequences and DNA sequences of the chimeric H chains are shown in SEQ ID NOS: 62 to 69. The culture supernatant (1 ml) of each of chLpMab-2, chLpMab-3, chLpMab-7, and chLpMab-9 (collected 24 hours after gene introduction) was reacted with LN319 cells, podoplanin expression strain, at 4° C. for 30 minutes and then reacted further with anti-human IgG-FITC antibody (product of Life Technologies) at 4° C. for 30 minutes. As a negative control, only secondary antibodies of them were used. As a positive control antibody, an NZ-8 antibody (1 µg/ml) which was a human chimeric antibody of the NZ-1 antibody and had a constant region of a human IgG1 antibody same as that of chLpMab-2, chLpMab-3, chLpMab-7, and chLpMab-9 was used. Fluorescence intensity was measured using EC800 (product of Sony). As a result, all the human chimeric antibodies showed good reactivity with the LN 319 cells (FIG. 3E). It has been apparent that the ADCC/CDC activity depends on the constant region of the human IgG1 antibody and the NZ-8 antibody having a constant region similar to that of the human IgG1 antibody has high ADCC/CDC activity (Patent Document 1), suggesting that various human chimeric antibodies, LpMab-2, LpMab-3, LpMab-7, and LpMab-9, similarly have high ADCC/CDC activity against podoplanin and are therefore useful as an antibody drug.

5. Immunohistostaininq

Various paraffin sections were deparaffined in xylene and ethanol solutions. The resulting sections were autoclaved for 20 minutes using an antigen activator reagent (citrate buffer (pH 6.0): product of Dako). Endogenous peroxidase was inactivated with 3% $H_2O_2$. After blocking at room temperature for 10 minutes with SuperBlock (product of Thermo Fisher), a primary antibody was reacted at room temperature for one hour. After amplification using a LSAB kit (product of Dako), color was developed using DAB (product of Dako).

Figure 4:
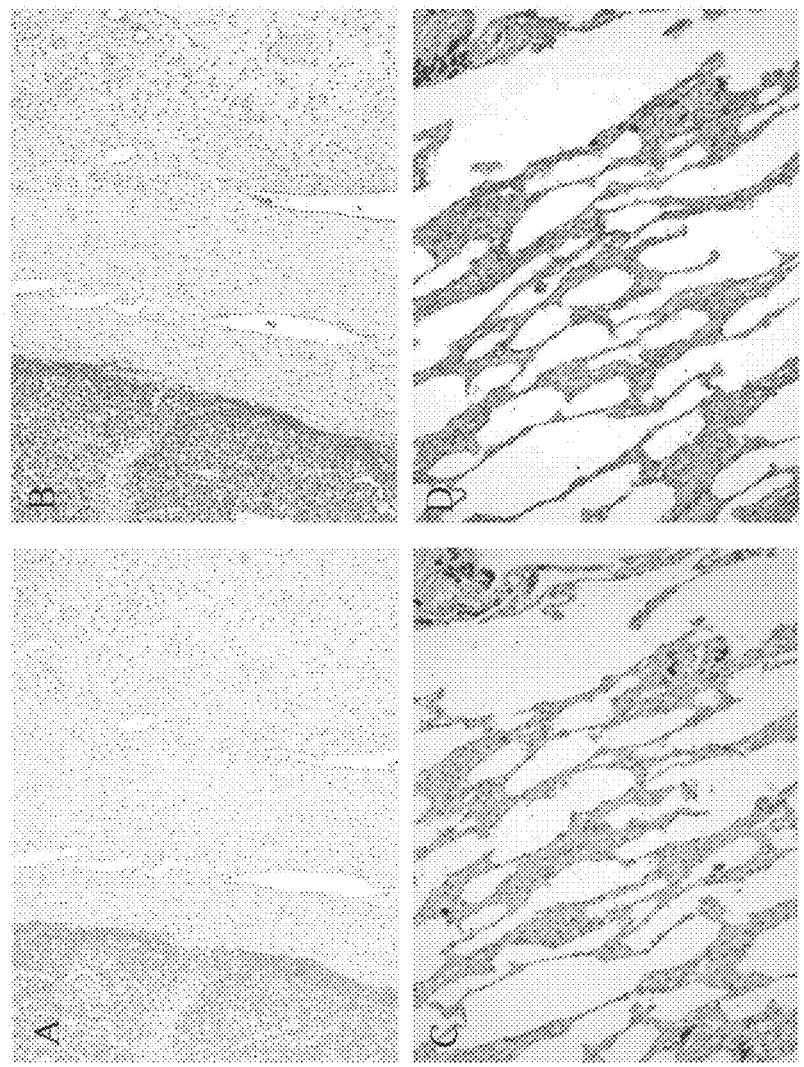
FIGS. 4A and B show the immunohistostaining results of testicular tumor cells with LpMab-2 and LpMab-7.
FIGS. 4C and D show the immunohistostaining results of normal alveolar epithelial cells with LpMab-2 and LpMab-7.

LpMab-2 is a tumor-specific antibody. LpMab-2 stained a tumor portion (left) of testicular tumor, but did not stain lymphatic epithelial cells at all (upper right) (FIG. 4A). LpMab-7 reacted with both (FIG. 4B), which coincided with the data of flow cytometry. LpMab-2 reacted with neither normal alveolar epithelial cells nor lymphatic cells (FIG. 4C). The LpMab-7 on the other hand stained alveolar epithelial cells and lymphatic vessel (FIG. 4D).

LpMab-3 showed a staining property similar to that of LpMab-7 but LpMab-9 showed no reactivity in immunohistostaining. LpMab-9, different from the other antibodies, has difficulty in reacting with podoplanin modified by formalin fixing and paraffin embedding, which has revealed that it is an antibody with a special epitope.

6. Antibody Gene Cloning 6-1. Determination of Amino Acid Sequence of Anti-Podoplanin Antibody and Base Sequence of Antibody Gene From hybridoma cells 1×10⁶ of the anti-podoplanin antibody, a total RNA was extracted using a QIAGEN RNeasy mini kit (product of Qlagen). From 1 µg of the total RNA, cDNA synthesis was performed using a SuperScript III First-Strand Syntheses kit (product of QIAGEN). The cDNA was used as a template in the following experiment.

For amplification of the H chain, the following primers were used:

```
                                          (SEQ ID NO: 42)
LpMab-2HatgS: ATG GAA AGG CAC TGG ATC TTT CTA (SEQ ID NO: 43)
LpMab-3HatgS: ATG AAC TTT GTG CTC AGC TTG ATT
```

```
                                          (SEQ ID NO: 44)
LpMab-7HatgS: ATG GAC TCC AGG CTC AAT TTA GTT (SEQ ID NO: 45)
LpMab-9HatgS: ATG GAA TGT CTG TGG AAC TTG CTA (SEQ ID NO: 46)
mIgG1woterAS: TTT ACC AGG AGA GTG GGA GA
```

The PCR reaction was performed using a QIAGEN HotStar Taq (product of QIAGEN). The reaction was made under the following temperature conditions: first at 95° C. for 15 minutes, next 35 cycles of 94° C. for 30 seconds, 50° C. for 30 seconds, and 72° C. for 1 minute 40 seconds, and then 72° C. for 10 minutes. The amplified PCR product was purified using a QIAGEN PCR purification kit. After subcloning using pcDNA3.1, the base sequence was determined from the vector primer.

The following primers were used for amplifying the L chain.

```
                                          (SEQ ID NO: 47)
LpMab-2LatgS: ATG AAG TTG CCT GTT AGG CTG TTG (SEQ ID NO: 48)
LpMab-3LatgS: ATG AAA TCA CAG ACC CAG GTC CTC (SEQ ID NO: 49)
LpMab-7LatgS: ATG AAG TTG CCT GTT AGG CTG TTG (SEQ ID NO: 50)
LpMab-9LatgS: ATG GAA TCA CAG ACC CAG GTC CTC (SEQ ID NO: 51)
moIgCKwoterAS: ACA CTC ATT CCT GTT GAA GC
```

The PCR reaction was performed using a QIAGEN HotStar Taq. The reaction was made under the following temperature conditions: first at 95° C. for 15 minutes, next 35 cycles of 94° C. for 30 seconds, 53° C. for 30 seconds, and 72° C. for 1 minute, and then 72° C. for 10 minutes. The amplified PCR product was purified using a QIAGEN PCR purification kit. After subcloning using pcDNA3.1, the base sequence was determined from the vector primer. The amino acid sequence was predicted from the base sequence.

The amino acid sequence of the CDR of each of the antibodies is shown in SEQ ID NOS: 2 to 25 and the amino acid sequence and the DNA sequence of the heavy chain and the light chain of each of the antibodies are shown in SEQ ID NOS: 26 to 41.

[Sequence Listing Free Text]

SEQ ID NO: 1 shows the amino acid sequence of human podoplanin protein.

SEQ ID NO: 2 shows the amino acid sequence of the heavy chain CDR1 of LpMab-2.

SEQ ID NO: 3 shows the amino acid sequence of the heavy chain CDR2 of LpMab-2.

SEQ ID NO: 4 shows the amino acid sequence of the heavy chain CDR3 of LpMab-2.

SEQ ID NO: 5 shows the amino acid sequence of the light chain CDR1 of LpMab-2.

SEQ ID NO: 6 shows the amino acid sequence of the light chain CDR2 of LpMab-2.

SEQ ID NO: 7 shows the amino acid sequence of the light chain CDR3 of LpMab-2.

SEQ ID NO: 8 shows the amino acid sequence of the heavy chain CDR1 of LpMab-3.

SEQ ID NO: 9 shows the amino acid sequence of the heavy chain CDR2 of LpMab-3.

SEQ ID NO: 10 shows the amino acid sequence of the heavy chain CDR3 of LpMab-3.
SEQ ID NO: 11 shows the amino acid sequence of the light chain CDR1 of LpMab-3.
SEQ ID NO: 12 shows the amino acid sequence of the light chain CDR2 of LpMab-3.
SEQ ID NO: 13 shows the amino acid sequence of the light chain CDR3 of LpMab-3.
SEQ ID NO: 14 shows the amino acid sequence of the heavy chain CDR1 of LpMab-7.
SEQ ID NO: 15 shows the amino acid sequence of the heavy chain CDR2 of LpMab-7.
SEQ ID NO: 16 shows the amino acid sequence of the heavy chain CDR3 of LpMab-7.
SEQ ID NO: 17 shows the amino acid sequence of the light chain CDR1 of LpMab-7.
SEQ ID NO: 18 shows the amino acid sequence of the light chain CDR2 of LpMab-7.
SEQ ID NO: 19 shows the amino acid sequence of the light chain CDR3 of LpMab-7.
SEQ ID NO: 20 shows the amino acid sequence of the heavy chain CDR1 of LpMab-9.
SEQ ID NO: 21 shows the amino acid sequence of the heavy chain CDR2 of LpMab-9.
SEQ ID NO: 22 shows the amino acid sequence of the heavy chain CDR3 of LpMab-9.
SEQ ID NO: 23 shows the amino acid sequence of the light chain CDR1 of LpMab-9.
SEQ ID NO: 24 shows the amino acid sequence of the light chain CDR2 of LpMab-9.
SEQ ID NO: 25 shows the amino acid sequence of the light chain CDR3 of LpMab-9.
SEQ ID NO: 26 shows the amino acid sequence of the heavy chain of LpMab-2.
SEQ ID NO: 27 shows the amino acid sequence of the light chain of LpMab-2.
SEQ ID NO: 28 shows the amino acid sequence of the heavy chain of LpMab-3.
SEQ ID NO: 29 shows the amino acid sequence of the light chain of LpMab-3.
SEQ ID NO: 30 shows the amino acid sequence of the heavy chain of LpMab-7.
SEQ ID NO: 31 shows the amino acid sequence of the light chain of LpMab-7.
SEQ ID NO: 32 shows the amino acid sequence of the heavy chain of LpMab-9.
SEQ ID NO: 33 shows the amino acid sequence of the light chain of LpMab-9.
SEQ ID NO: 34 shows the DNA sequence of the heavy chain of LpMab-2.
SEQ ID NO: 35 shows the DNA sequence of the light chain of LpMab-2.
SEQ ID NO: 36 shows the DNA sequence of the heavy chain of LpMab-3.
SEQ ID NO: 37 shows the DNA sequence of the light chain of LpMab-3.
SEQ ID NO: 38 shows the DNA sequence of the heavy chain of LpMab-7.
SEQ ID NO: 39 shows the DNA sequence of the light chain of LpMab-7.
SEQ ID NO: 40 shows the DNA sequence of the heavy chain of LpMab-9.
SEQ ID NO: 41 shows the DNA sequence of the light chain of LpMab-9.
SEQ ID NO: 42 shows the DNA sequence of primer LpMab-2HatgS.
SEQ ID NO: 43 shows the DNA sequence of primer LpMab-3HatgS.
SEQ ID NO: 44 shows the DNA sequence of primer LpMab-7HatgS.
SEQ ID NO: 45 shows the DNA sequence of primer LpMab-9HatgS.
SEQ ID NO: 46 shows the DNA sequence of primer mIgG1woterAS.
SEQ ID NO: 47 shows the DNA sequence of primer LpMab-2LatgS.
SEQ ID NO: 48 shows the DNA sequence of primer LpMab-3LatgS.
SEQ ID NO: 49 shows the DNA sequence of primer LpMab-7LatgS.
SEQ ID NO: 50 shows the DNA sequence of primer LpMab-9HatgS.
SEQ ID NO: 51 shows the DNA sequence of primer mIgCKwoterAS.
SEQ ID NO: 52 shows the DNA sequence of primer hIgG1CH1.BamHI.
SEQ ID NO: 53 shows the DNA sequence of primer hIgG1CH3-R1.NotI.
SEQ ID NO: 54 shows the DNA sequence of primer HindIII-LpMab-2HatgS.
SEQ ID NO: 55 shows the DNA sequence of primer LpMab-2HVHR-BamHI.
SEQ ID NO: 56 shows the DNA sequence of primer HindIII-LpMab-3HatgS.
SEQ ID NO: 57 shows the DNA sequence of primer LpMab-3HVHR-BamHI.
SEQ ID NO: 58 shows the DNA sequence of primer HindIII-LpMab-7HatgS.
SEQ ID NO: 59 shows the DNA sequence of primer LpMab-7HVHR-BamHI.
SEQ ID NO: 60 shows the DNA sequence of primer HindIII-LpMab-9HatgS.
SEQ ID NO: 61 shows the DNA sequence of primer LpMab-9HVHR-BamHI.
SEQ ID NO: 62 shows the DNA sequence of the chimeric heavy chain of LpMab-2.
SEQ ID NO: 63 shows the amino acid sequence of the chimeric heavy chain of LpMab-2.
SEQ ID NO: 64 shows the DNA sequence of the chimeric heavy chain of LpMab-3.
SEQ ID NO: 65 shows the amino acid sequence of the chimeric heavy chain of LpMab-3.
SEQ ID NO: 66 shows the DNA sequence of the chimeric heavy chain of LpMab-7.
SEQ ID NO: 67 shows the amino acid sequence of the chimeric heavy chain of LpMab-7.
SEQ ID NO: 68 shows the DNA sequence of the chimeric heavy chain of LpMab-9.
SEQ ID NO: 69 shows the amino acid sequence of the chimeric heavy chain of LpMab-9.

<Cancer Cell-Specific Anti-Podoplanin Antibody and Preparation Method Thereof>

TECHNICAL FIELD

The present invention relates to a cancer cell-specific novel anti-podoplanin antibody and preparation method thereof, and an anticancer agent containing the cancer cell-specific anti-podoplanin antibody, and the like.

BACKGROUND ART

Cancer cell-induced platelet aggregation is one of the causes of hematogenous metastasis. Cancer cells that have entered into blood vessels are destroyed by the attack of the immune system of hosts or by physical impact, but due to protection by platelet aggregation, metastasis occurs. Platelet aggregation promotes adhesion of cancer cells to vascular endothelial cells and releases growth factors to cause local growth of cancer cells. Further, embolus that occurs due to obstruction of capillary vessels with cancer cells and aggregates of blood platelets also contributes to the promotion of hematogenous metastasis.

Highly metastatic line NL-17 cells and lowly metastatic line NL-14 cells were established by experimentally repeating pulmonary metastasis of the mouse colon cancer cell line colon26 (Non-Patent Document 1a). In vitro experiment, the NL-17 cells caused platelet aggregation in mice but their activity was inhibited by an 8F11 antibody which is a monoclonal antibody highly reactive with the NL-17 cells and low reactive with the NL-14 cells. In vivo experiment, experimental pulmonary metastasis of the NL-17 cells was inhibited by the 8F11 antibody. This has suggested that the NL-17 cells aggregate blood platelets by a platelet aggregation factor recognized by the 8F11 antibody and thereby cause pulmonary metastasis. This platelet aggregation factor was found later to be a molecule equal to that of podoplanin (podoplanin/Aggrus/T1 alpha/gp36).

Mouse podoplanin was purified from the NL-17 cells by using an affinity column using the 8F11 antibody and a WGA lectin column (Non-Patent Document 2a). The mouse podoplanin caused platelet aggregation in the absence of a plasma component in a concentration dependent manner and the aggregation reaction was inhibited completely by the 8F11 antibody.

The present inventors have succeeded in gene cloning of podoplanin (Non-Patent Document 3a). Podoplanin is a type I transmembrane protein having, at the C terminal thereof, a transmembrane site. Epitope analysis of the 8F11 antibody which is a neutralizing of mouse podoplanin and detailed mutagenesis experiment have revealed that threonine of a PLAG domain (three repeats of the sequence EDxxVTPG) is an active site of podoplanin-induced platelet aggregation and is conserved across species (Non-Patent Document 4a). After that, it has been found that sialic acid of an O-linked sugar chain added to threonine of the PLAG domain is the active center of platelet aggregation (Non-Patent Document 5a).

The present inventors prepared a monoclonal antibody, an NZ-1 antibody, by using rats in order to purify human podoplanin (Non-Patent Document 6a). The NZ-1 antibody is useful in various experiments such as western blotting, flow cytometry, immunohistostaining, and immunoprecipitation. The present inventors have reported that the NZ-1 antibody also exhibits ADCC activity and CDC activity in human podoplanin-positive tumor cells (Patent Document 1a).

The NZ-1 antibody inhibited binding between human podoplanin and a murine or human C-type lectin-like receptor-2 (CLEC-2) and also inhibited human podoplanin-induced platelet aggregation in a concentration dependent manner, thereby significantly inhibiting human-podoplanin-induced pulmonary metastasis (Non-Patent Document 7a).

Human podoplanin is highly expressed in malignant brain tumor, malignant mesothelioma, testicular tumor (particularly, seminoma), ovarian cancer, and various squamous cell cancers (oral cancer, pharyngeal cancer, laryngeal cancer, esophageal cancer, lung cancer, skin cancer, and uterine cervical cancer) (Non-Patent Documents 8a to 11a). Human podoplanin is, on the other hand, expressed also in normal cells such as lymphatic epithelial cells and alveolar epithelial cells. An antibody against human podoplanin expressed specifically in cancer cells, if any, are useful as a drug, a diagnostic agent, a reagent, or the like.

Various anti-podoplanin antibodies have heretofore been prepared, but most of them react with both the cancer tissue and normal tissue. There is no report on a cancer cell-specific anti-podoplanin antibody useful for immunohistostaining and a strategic preparation method thereof.

CITATION LIST

Patent Document

[Patent Document 1a] WO2011/040565

Non-Patent Document

[Non-Patent Document 1a] Tsuruo T., Yamori T. et al., Cancer Res. 43, 5437-5442, 1983.
[Non-Patent Document 2a] Toyoshima M., Nakajima M. et al., Cancer Res. 55, 767-773, 1995.
[Non-Patent Document 3a] Kato Y., Fujita N. et al., J. Biol. Chem. 278, 51599-51605, 2003.
[Non-Patent Document 4a] Kaneko MK., Kato Y. et al., Gene 378C:52-57, 2006.
[Non-Patent Document 5a] Kaneko M., Kato Y. et al., J. Biol. Chem. 279, 38838-38843, 2004.
[Non-Patent Document 6a] Kato Y., Kaneko MK. et al., Biochem. Biophys. Res. Commun., 349:1301-1307, 2006
[Non-Patent Document 7a] Kato Y., Kaneko MK. et al., Cancer Sci. 99, 54-61, 2008.
[Non-Patent Document 8a] Kato Y., Sasagawa I. et al., Oncogene 23, 8552-8556, 2004.
[Non-Patent Document 9a] Kato Y., Kaneko M. et al., Tumor Biol. 26, 195-200, 2005.
[Non-Patent Document 10a] Mishima K., Kato Y. et al., Acta Neuropathol. 111(5):483-488, 2006a
[Non-Patent Document 11a] Mishima K., Kato Y. et al., Acta Neuropathol. 111(6):563-568. 2006b

SUMMARY

Technical Problem

An object of the present invention is to provide an antibody against cancer cell-specific podoplanin useful as a drug, a diagnostic agent, and a reagent, and a strategic preparation method thereof.

Solution to Problem

With a view to achieving the above-described object, the present inventors have proceeded with studies and found that an antibody against cancer cell-specific podoplanin, that is, a cancer cell-specific antibody (Cancer-specific monoclonal antibody: CasMab) can be established by expressing podoplanin in cells that add thereto a cancer cell-specific sugar-chain structure and thereby adding the cancer cell-specific sugar-chain structure to the podoplanin, immunizing an animal with these cells to obtain an antibody, and then carrying out primary screening to select an antibody that reacts with a cancer cell-specific podoplanin.

LpMab-23, one example of the antibody established by the above method, shows high reactivity, in immunohistostaining using testicular tumor or squamous cell cancer such as lung cancer or esophagus cancer, with podoplanin expressed in cancer cells but does not react with podoplanin expressed in normal cells such as lymphatic epithelial cells or alveolar epithelial Type 1 cells, showing that it is a cancer cell-specific anti-podoplanin antibody. This strongly suggests that LpMab-23 recognizes a sugar-chain structure or steric structure possessed only by podoplanin on cancer cells.

Described specifically, the present invention relates to:

[A1] a method of producing an antibody against podoplanin expressed in a cancer-cell specific manner, including:
  a step of introducing a nucleic acid encoding podoplanin into cells that express a cancer cell-specific sugar-chain structure and thereby expressing podoplanin;
  a step of immunizing a non-human mammal with the cells to obtain an antibody; and
  a step of using a purified cancer cell-specific podoplanin in primary screening of the antibody;

[A2] the method as described above in [A1], further including:
  a step of, after the primary screening, selecting an antibody that reacts with the tumor cells or tissue and does not react with the normal cells or tissue;

[A3] the method as described above in either [A1] or [A2], wherein the cells that express a cancer cell-specific sugar-chain structure are cancer cells;

[A4] the method as described above in [A3], wherein the cancer cells are cells derived from glioblastoma cell line LN229;

[A5] the method as described above in either [A1] or [A2], wherein the cells that express a cancer cell-specific sugar-chain structure are cells artificially altered to express the cancer cell-specific sugar-chain structure by introducing a glycosyltransferase;

[A6] the method as described above in any one of [A1] to [A5], wherein the step of selecting an antibody that reacts with the tumor cells or tissue and does not react with the normal cells or tissue is achieved by immunohistostaining or immunocytostaining;

[A7] a cancer-cell specific anti-podoplanin antibody or antigen-binding fragment thereof in any of the following (i) to (iii):
  (i) having at least one of the following six CDRs:

```
a heavy chain CDR1: GFSVTSYGIH
a heavy chain CDR2: VIWTSGNTNYNSALMS
a heavy chain CDR3: EDYYGYAMDY
a light chain CDR1: RSSQSLLYSNGKTYLN
a light chain CDR2: LVSKLDS
a light chain CDR3: VQGTHFPWT;
```

(ii) having, in at least one of the heavy chains CDR1 to 3 and light chains CDR1 to 3, addition, substitution, or deletion of one to several amino acids; and
  (iii) having, as at least one of the heavy chains CDR1 to 3 and light chains CDR1 to 3, an amino acid sequence with 80% or more identity with the amino acid sequence of the heavy chains CDR1 to 3 and light chains CDR1 to 3;

[A8] a cancer cell-specific anti-podoplanin antibody or antigen binding fragment thereof having:
  a heavy chain having an amino acid sequence represented by SEQ ID NO: 78;
  a heavy chain having, in the amino acid sequence represented by SEQ ID NO: 78, an amino acid sequence having addition, substitution, or deletion of one to several amino acids; or
  a heavy chain having an amino acid sequence having 80% or more identity with the amino acid sequence represented by SEQ ID NO: 78;

[A9] a cancer cell-specific anti-podoplanin antibody or an antigen binding fragment thereof having:
  a light chain having an amino acid sequence represented by SEQ ID NO: 77;
  a light chain having, in the amino acid sequence represented by SEQ ID NO: 77, an amino acid sequence having addition, substitution, or deletion of one to several amino acids; or
  a light chain having an amino acid sequence having 80% or more identity with the amino acid sequence represented by SEQ ID NO: 77;

[A10] the cancer cell-specific anti-podoplanin antibody or antigen binding fragment thereof as described above in any one of [A7] to [A9], wherein one or more N-linked sugar chains have been bound to an Fc region and fucose has not been bound to N-acetylglucosamine at a reducing end of the N-linked sugar chain;

[A11] a nucleic acid encoding any one of the heavy chains CDR1 to 3 and the light chains CDR1 to 3 as described above in [A7];

[A12] a nucleic acid encoding any one of the heavy chains described above in [A8] and the light chains as described above in [A9];

[A13] an expression vector containing the nucleic acid as described above in either [A11] or [A12];

[A14] a transformant containing the expression vector as described above in [A13];

[A15] a method of producing a cancer cell-specific anti-podoplanin antibody, including a step of expressing an antibody in the transformant as described above in [A14] and a step of collecting the antibody;

[A16] a pharmaceutical composition containing, as an effective ingredient thereof, the cancer cell-specific anti-podoplanin antibody or antigen-binding fragment thereof as described above in [A7];

[A17] a pharmaceutical composition containing, as an effective ingredient thereof, the cancer cell-specific anti-podoplanin antibody or antigen-binding fragment thereof as described above in [A6] to which a substance having an anti-cancer activity has been bound; and

[A18] the pharmaceutical composition as described above in either [A16] or [A17], which is a preventive or a therapeutic agent for at least one disease selected from the group consisting of cancers, thrombosis, and arteriosclerosis.

Advantageous Effects of Invention

The method of producing an antibody according to the present invention can provide a cancer cell-specific antibody (Cancer-specific monoclonal antibody: CasMab) against podoplanin.

When CasMab is used, the anti-tumor activity of the antibody can be exhibited in a cancer cell-specific manner and a drug having reduced side effects can be obtained. It is also useful for delivery of an agent targeting cancer cells and therefore is highly useful as a diagnostic agent or a reagent.

The cancer cell-specific anti-podoplanin antibody of the present invention is therefore useful as a reagent for research, a diagnostic agent, or a drug candidate

DESCRIPTION OF EMBODIMENTS

A method of producing an antibody against podoplanin expressed in a cancer cell specific manner, includes:

a step of introducing a nucleic acid encoding podoplanin into cells that express a cancer cell-specific sugar-chain structure and thereby expressing podoplanin;

a step of immunizing a non-human mammal with the cells to obtain an antibody; and a step of carrying out primary screening of the antibody while using a purified cancer cell-specific podoplanin.

The term "antibody against podoplanin expressed in a cancer cell-specific manner" as used herein means an antibody whose reactivity with podoplanin expressed in cancer cells is significantly higher than reactivity with podoplanin expressed in normal cells. In one aspect, the "antibody against podoplanin expressed in a cancer cell-specific manner" reacts with podoplanin expressed in cancer cells but does not react with podoplanin expressed in normal cells at all. In one aspect, the "antibody against podoplanin expressed in a cancer cell-specific manner" has markedly high reactivity with podoplanin expressed in cancer cells, while it reacts, to some extent, with podoplanin expressed in normal cells. Podoplanin expressed in cancer cells have a cancer cell-specific sugar-chain structure so that an antibody recognizing such a sugar-chain structure can discriminate podoplanin expressed in a cancer cell-specific manner from podoplanin expressed in normal cells.

The "antibody against podoplanin expressed in a cancer cell-specific manner" used herein may be called "cancer cell-specific anti-podoplanin antibody".

Podoplanin is highly expressed in in malignant brain tumor, malignant mesothelioma, testicular tumor (particularly, seminoma), ovarian cancer, and various squamous cell cancers (oral cancer, pharyngeal cancer, laryngeal cancer, esophageal cancer, lung cancer, skin cancer, and uterine cervical cancer), while it is expressed also in normal cells such as lymphatic epithelial cells or alveolar epithelial cells.

Human podoplanin is a protein represented by SEQ ID NO: 70. The term "podoplanin" as used herein embraces a functional variant thereof.

The "antibody" used herein has a structure in which two heavy chains (H chains) and two light chains (L chains) stabilized by a pair of disulfide bonds have been associated with each other. The heavy chain is composed of a heavy chain variable region VH, heavy chain constant regions CH1, CH2, and CH3, and a hinge region located between CH1 and CH2, while the light chain is composed of a light chain variable region VL and a light chain constant region CL. Of these regions, a variable region fragment (Fv) composed of VH and VL is a region directly involved in antigen binding and provides the antibody with diversity. The antigen binding region composed of VL, CL, VH, and CH1 is called "Fab region" and a region composed of the hinge region, CH2, and CH3 is called "Fc region".

Of the variable regions, the region in direct contact with an antigen shows a particularly large change and is called "complementarity-determining region: CDR". A relatively mutation-less region other than CDR is called framework (framework region: FR). The light chain variable region and the heavy chain variable region each have three CDRs (heavy chains CDR1 to 3 and light chains CDR1 to 3).

The "cells that express a cancer cell-specific sugar-chain structure" as used herein may be any cells insofar as they express a cancer cell-specific sugar-chain structure. For example, they may be cancer cells or cells obtained by introducing a necessary glycosyltransferase into non-cancer cells and thereby artificially altering them so that they express a cancer cell-specific sugar-chain structure. Examples of the "cells that express a cancer cell-specific sugar-chain structure" include the following cells:

Cells derived from glioblastoma cell line LN229.

Cells obtained by gene introduction of glycosyltransferase KSGal6ST into glioblastoma cell line LN464 cells (Hayatsu N, et al., Biochem Biophys Res Commun, 368, 217-222, 2008). The present inventors have reported in this document that a high expression strain of keratan sulfate known to be expressed highly in a brain tumor tissue can be obtained by gene introduction of glycosyltransferase KSGal6ST into glioblastoma cell line LN464 cells.

Cells obtained by gene introduction of a glycosyltransferase into cervical cancer cells (HeLa cells) or leukemia cells (Namalwa cells) (Kimura H, et al., Biochem Biophys Res Commun. 1997 Aug. 8; 237(1):131-7.). In this document, the present inventors observe in detail what kind of sugar chain is added by gene introduction of a glycosyltransferase into cervical cancer cells (HeLa cells) or leukemia cells (Namalwa cells).

cells obtained by gene introduction of a glycosyltransferase into Namalwa cells (Kaneko M, et al., H. *FEBS Lett.* 1999 Jun. 11; 452(3):237-42.) In this document, the present inventors observe in detail what kind of sugar chain is added by gene introduction of a glycosyltransferase into Namalwa cells.

cells obtained by introducing a glycosyltransferase into monkey kidney cells (COS1 cells) (Kaneko M, et al., Blood. 1997 Jul. 15; 90(2):839-49.)

cells obtained by introducing glycosyltransferase into hamster ovarian cells (CHO-Lec1 cells) (Kaneko M, et al., FEBS Lett. 2003 Nov. 20; 554(3):515-9.)

The "step of introducing a nucleic acid encoding podoplanin into cells that express a cancer cell-specific sugar-chain structure" described herein can be performed by those skilled in the art by a conventional method. The nucleic acid encoding podoplanin is usually not different between when podoplanin is cancer cell-specific podoplanin and when it is normal cell podoplanin so that the nucleic acid may encode either of them. The nucleic acid used herein is not limited insofar as it can express an intended protein and examples include DNA, RNA, DNA/RNA chimera, and artificial nucleic acid.

The "step of immunizing a non-human mammal with the cells to obtain an antibody" described herein is performed by administering whole cells that express cancer cell-specific podoplanin to a non-human mammal. Immunization may be performed by a conventional method. For example, from $1 \times 10^7$ to $1 \times 10^9$ cells can be administered peritoneally in a plurality of times once 10 days. The "non-human mammal" described herein typically means a mouse. It is however not particularly limited thereto and examples include rats, hamsters, rabbits, cats, dogs, monkeys, goats, sheep, cows, and horses.

The term "primary screening of the antibody" as used herein means first screening in a procedure of identifying and purifying an intended antibody from antibody producing cells. For example, it means screening using a culture supernatant of hybridomas producing a monoclonal antibody.

The primary screening of the antibody in the present invention is typically performed in the following manner.

First, podoplanin is expressed in a cell line that expresses a cancer cell-specific sugar-chain structure and is then purified using an affinity tag (FLAG tag, His tag, Myc tag, PA tag, or the like). The cancer cell-specific podoplanin thus purified is immobilized on an ELISA plate. An antibody obtained from antibody producing cells is added to the plate and wells in which reaction occurs are selected. Different from a method of immobilizing a synthetic peptide, an *Escherichia coli*-expressed protein, or a protein expressed by an animal cell line (CHO, COS, HEK-293T, or the like), which method is used in typical primary screening, the above-described method enables selection of a cancer cell-specific antibody at an early stage.

The method of producing a cancer cell-specific anti-podoplanin antibody according to the present invention may include, after the primary screening, a "step of comparing the reactivity of the antibody with tumor cells or tissue and that with normal cells or tissue".

The term "step of comparing the reactivity of the antibody with tumor cells or tissue and that with normal cells or tissue" as used herein means a step of reacting tumor cells or tissue with the resulting antibody to detect presence or absence of binding, while reacting normal cells or tissue with the resulting antibody to detect presence or absence of binding. This step can be achieved by flow cytometry, immunohistostaining (IHC), immunocytostaining (ICC), or the like.

A cancer cell-specific antibody can be obtained by comparing the reactivity of tumor cells or tissue with the resulting antibody and the reactivity of normal cells or tissue with the resulting antibody and then selecting an antibody having the reactivity with tumor cells or tissue significantly higher than the reactivity with normal cells or tissue. The cancer cell-specific antibody thus selected may thereafter be purified further.

The anti-podoplanin antibody of the present invention may be either a monoclonal antibody or a polyclonal antibody. The anti-podoplanin antibody of the present invention may be any isotype of IgG, IgM, IgA, IgD, and IgE. It may be obtained by immunizing a non-human animal such as mouse, rat, hamster, guinea pig, rabbit, or chicken. It may also be a recombinant or a chimeric antibody, a humanized antibody, a fully humanized antibody, or the like. The "chimeric antibody" means an antibody in which fragments of antibodies derived from different species have been linked to each other.

The term "humanized antibody" as used herein means an antibody obtained by substituting, with an amino acid sequence characteristic to an antibody derived from nonhuman, a sequence of a human antibody at a corresponding position. Examples of it include antibodies composed of heavy chains CDR1 to 3 and light-chains CDR1 to 3 of an antibody prepared by immunizing a mouse and all the other regions, including four respective framework regions (FR) of the heavy chains and light chains, derived from a human antibody. Such an antibody may also be called "CDR grafted antibody". The term "humanized antibody" may include a human chimeric antibody.

The term "antigen-binding fragment" of the anti-podoplanin antibody as used herein means a fragment of an anti-podoplanin antibody and a fragment that binds to podoplanin. Specific examples include, but are not limited to, Fab composed of VL, VH, CL, and CH1 regions; F(ab')2 having two Fabs connected to each other via a disulfide bond in a hinge region; Fv composed of VL and VH; a single-chain antibody scFv having VL and VH connected to each other via an artificial polypeptide linker; and bispecific antibodies such as diabody, scDb, tandem scFv, and leucine zipper.

The cancer cell-specific anti-podoplanin antibody in one aspect of the present invention has at least one of the following six CDRs. These CDRs have CDR sequences of LpMab-23.

```
                                         (SEQ ID NO: 71)
heavy chain CDR1: GFSVTSYGIH (SEQ ID NO: 72)
heavy chain CDR2: VIWTSGNTNYNSALMS (SEQ ID NO: 73)
heavy chain CDR3: EDYYGYAMDY (SEQ ID NO: 74)
light chain CDR1: RSSQSLLYSNGKTYLN (SEQ ID NO: 75)
light chain CDR2: LVSKLDS (SEQ ID NO: 76)
light chain CDR3: VQGTHFPWT
```

In respective aspects of the anti-podoplanin antibody, the anti-podoplanin antibody of the present invention may contain any number of the six CDRs insofar as it produces the advantage of the present invention. Examples include 2 or more, 3 or more, 4 or more, 5 or more, and 6.

In the above aspects, at least one of the heavy chains CDR1 to 3 and the light chains CDR1 to 3 may contain addition, substitution, or deletion of one to several amino acids.

In the present specification, the term "amino acid" is used in its broadest meaning and it embraces not only naturally occurring amino acids but also artificial amino acid variants and derivatives of them. The amino acids may be represented by a commonly used single-letter or three-letter code. Examples of the amino acid or derivatives thereof used herein include naturally occurring proteinogenic L-amino acids, non-naturally occurring amino acids, and chemically synthesized compounds having properties known in the art as characteristics of an amino acid. Examples of the non-naturally occurring amino acids include, but are not limited to, α,α-disubstituted amino acids (such as α-methylalanine), N-alkyl-α-amino acids, D-amino acids, β-amino acids, and α-hydroxy acids, each having a main chain structure different from that of naturally occurring amino acids; amino acids (such as norleucine and homohistidine) having a side-chain structure different from that of naturally occurring amino acids; amino acids (such as "homo" amino acids, homophenylalanine, and homohistidine) having extra methylene in the side chain thereof; and amino acids (such as cysteic acid) obtained by substituting a carboxylic acid functional group in the side chain by a sulfonic acid group.

When the expression "having addition, substitution, or deletion of one to several amino acids" is used herein, the number of amino acids to be deleted, substituted, or the like is not particularly limited insofar as the resulting polypeptide retains its function as a CDR. The number of amino acids is set at, for example, 1, 2, 3, or 4. The amino acid to be substituted or added may be, as well as a naturally-occurring proteinogenic amino acid, a non-naturally-occurring amino acid or an amino acid analog. The position of deletion, substitution, or addition of an amino acid may be any site of an original CDR sequence insofar as the function as a CDR is retained.

In each of the above-described aspects of the anti-podoplanin antibody, at least one of the heavy chains CDR1 to 3 and the light chains CDR 1 to 3 may have an amino acid sequence having 80% or more identity with the amino acid sequence of the original heavy chains CDR1 to 3 and the light chains CDR 1 to 3.

The term "having 80% or more identity" as used herein means that when two polypeptides having an original sequence and a mutated sequence, respectively, are aligned so that their amino acid sequences show the maximum identity, the number of amino acid residues which they have in common is 80% or more of the number of the amino acids of the original sequence.

The identity is not limited insofar as it is 80% or more and the function as a CDR can be retained. It can be set at, for example, 85% or more, 90% or more, 95% or more, 98% or more, or 99% or more.

A CDR composed of an amino acid sequence obtained by adding, substituting, or deleting an amino acid from the amino acid sequence of the heavy chains CDR1 to 3 and the light chains CDR1 to 3, or a CDR having 80% or more sequence identity to the amino acid sequence of the heavy chains CDR1 to 3 and the light chains CDR1 to 3 may be prepared using a known method such as site-specific mutagenesis, random mutagenesis, chain shuffling, or CDR walking. It is well known to those skilled in the art that when the above method is used, CDRs with more mature affinity may be obtained by displaying an antibody or antibody fragment having a variety of variations in CDRs on the phage surface by phage display, followed by screening using an antigen (for example, Wu et al., PNAS, 95:6037-6042 (1998); Schier, R. et al., J. Mol. Bio. 263:551-567 (1996); Schier, R. et al., J. Mol. Biol. 255:28-43 (1996); Yang, W. P. et al., J. Mol. Biol., 254:392-403 (1995).).

A cancer cell-specific anti-podoplanin antibody according to another aspect of the present invention has:
  a light chain having an amino acid sequence represented by SEQ ID NO: 77;
  a light chain having, in the amino acid sequence represented by SEQ ID NO: 77, an amino acid sequence with addition, substitution, or deletion of one to several amino acids; or
  a light chain having 80% or more identity with the amino acid sequence represented by SEQ ID NO: 77.

The amino acid sequence represented by SEQ ID NO: 77 is an amino acid sequence of the light chain of LpMab-23.

A cancer cell-specific anti-podoplanin antibody according to a further aspect of the present invention has:
  a heavy chain having an amino acid sequence represented by SEQ ID NO: 78;
  a heavy chain having, in the amino acid sequence represented by SEQ ID NO: 78, an amino acid sequence with addition, substitution, or deletion of one to several amino acids; or
  a heavy chain having an amino acid sequence having 80% or more identity with the amino acid sequence represented by SEQ ID NO: 78.

The amino acid sequence represented by SEQ ID NO: 78 is an amino acid sequence of the heavy chain of LpMab-23.

When the expression "having addition, substitution, or deletion of one to several amino acids in the amino acid sequence of the heavy chain or light chain" is used herein, the number of amino acids to be added, substituted or deleted can be set at, for example, 1, 2, 3, 4, 5, 6, 7, 8, 9, or 10. Other terms or expressions have the same meaning as described above.

The cancer cell-specific anti-podoplanin antibody according to the present invention may be an antibody in which one or more N-linked sugar chains have been bound to an Fc region and fucose has not been bound to N-acetylglucosamine at the reducing end of the N-linked sugar chains.

For example, the Fc region of an IgG antibody has therein two binding sites of an N-linked sugar chain and complex-type sugar chains are bound to these sites. The term "N-linked sugar chain" as used herein means a sugar chain to be bound to Asn of an Asn-X-Ser/Thr sequence and has a common structure $Man_3GlcNAc_2$-Asn. It is classified into a high mannose type, a hybrid type, a complex type, and the like, depending on the kind of the sugar chains bound to two mannoses (Man) at the non-reducing end.

Although fucose may bind to N-acetylglucosamine (GlcNAc) at the reducing end of an N-linked sugar chain, it is known that when fucose does not bind to it, compared with when fucose binds to it, ADCC activity shows a remarkable increase. This is described in, for example, the pamphlet of WO2002/031140, the disclosure of which is incorporated by reference herein in its entirety.

Since a remarkable improvement in ADCC activity may lead to a reduction of the dose when an antibody is used as a medicine, adverse side effects can be alleviated and at the same time, medical expenses can be reduced.

The anti-podoplanin antibody of the present invention may be used after a substance having an anti-cancer activity is bound thereto.

The term "substance having an anti-cancer activity" as used herein means a substance which causes at least one of reduction (retardation or stopping) of a tumor size, inhibition of tumor metastasis, inhibition (retardation or stopping) of tumor growth, and alleviation of one or plural symptoms associated with cancer. Specific examples thereof include, but are not limited to, toxins, anti-cancer agents, and radioisotopes.

Examples of a toxin having an anti-cancer activity include *Pseudomonas* exotoxin (PE) or a cytotoxic fragment thereof (for example, PE38), a diphtheria toxin, and ricin A. The toxin having an anti-cancer activity exhibits toxicity only against cells into which a toxin together with an anti-podoplanin antibody is incorporated, that is, cancer cells expressing podoplanin so that it is advantageous in that it is specifically effective without adversely affecting cells around it. In particular, the anti-podoplanin antibody of the present invention is useful because it specifically binds to anti-podoplanin that is expressed in tumor cells.

Examples of the anti-cancer agent include low molecular weight compounds such as adriamycin, daunomycin, mitomycin, cisplatin, vincristine, epirubicin, methotrexate, 5-fluorouracil, aclacinomycin, nitrogen mustards, cyclophosphamide, bleomycin, daunorubicin, doxorubicin, vincristine, vinblastine, vindesine, tamoxifen, and dexamethasone, and proteins such as cytokines activating immunocompetent cells (for example, human interleukin 2, human granulocyte-macrophage colony-stimulating factor, human macrophage colony-stimulating factor, and human interleukin 12).

Examples of the radioisotope having an anti-cancer activity include $^{32}P$, $^{14}C$, $^{125}I$, $^{3}H$, $^{131}I$, $^{211}At$, and $^{90}Y$. The radioisotope also exhibits toxicity to cells around cells to which an anti-podoplanin antibody binds, that is, podoplanin expression cells. In general, cancer cells are not uniform and not every cancer cell expresses podoplanin so that radioisotopes are useful for killing podoplanin-negative cancer cells around them. Further, when a radioisotope is bound, the anti-podoplanin antibody may be a low molecular weight antibody such as Fab or scFv.

The substance having an anti-cancer activity may be directly bound to an anti-podoplanin antibody by a known method. It may be bound to the anti-podoplanin antibody after enclosed in a carrier such as liposome.

When the substance having an anti-cancer activity is a protein or a polypeptide, the substance having an anti-cancer activity may be expressed as a fusion protein with an anti-podoplanin antibody by linking a nucleic acid (which will be described later) encoding the anti-podoplanin antibody of the present invention and DNA encoding the substance having an anti-cancer activity and inserting it into an appropriate expression vector.

(Nucleic Acid)

The present invention embraces a nucleic acid encoding the anti-podoplanin antibody of the present invention. The nucleic acid may be either a naturally occurring nucleic acid or an artificial nucleic acid. Examples include, but are not limited to, DNA, RNA, and a chimera of DNA and RNA. The base sequence of the nucleic acid encoding the anti-podoplanin antibody can be determined by a method known per se in the art or based thereon and can be prepared by a known method or a method based thereon.

Examples of the nucleic acid encoding the cancer-specific anti-podoplanin antibody of the present invention include, but are not limited to, DNA (SEQ ID NO: 80) encoding the heavy chain of LpMab-23 represented by SEQ ID NO: 78 and DNA (SEQ ID NO: 79) encoding the light chain of LpMab-23 represented by SEQ ID NO: 77.

The nucleic acids encoding the CDRs of LpMab-23, respectively, are contained in the DNA sequences represented by these SEQ ID NOs.

(Expression Vector)

The present invention also embraces an expression vector containing the nucleic acid encoding the anti-podoplanin antibody of the present invention. The expression vector can be selected as needed according to a host cell to be used. Examples include a plasmid, a retrovirus vector, an adenovirus vector, an adeno-associated virus (AAV) vector, a plant virus vector such as cauliflower mosaic virus vector or tobacco mosaic virus vector, a cosmid, a YAC, and an EBV-derived episome. The nucleic acid encoding the anti-podoplanin antibody of the present invention may be inserted into these expression vectors by a known method (such as by a method using a restriction enzyme).

The expression vector of the present invention may further contain a promoter for controlling the expression of an antibody gene, a replication origin, a selection marker gene, or the like. The promoter and the replication origin may be selected as needed, depending on the nature of the host cell and vector (Transformant)

The present invention embraces a transformant containing the vector of the present invention. The transformant can be obtained by transfecting the vector of the present invention into an appropriate host cell. Examples of the usable host cell usable include eukaryotic cells such as mammalian cells (CHO cells, COS cells, myeloma cells, HeLa cells, Vero cells, and the like), insect cells, plant cells, or fungus cells (*Saccharomyces, Aspergillus*, or the like), and prokaryotic cells such as *Escherichia coli* (*E. coli*) and *Bacillus subtilis*.

(Production Method of Antibody)

Although no limitation is imposed on the method of producing an anti-podoplanin antibody of the present invention, it can be obtained, for example, by isolating antibody producing cells from a non-human mammal immunized with podoplanin or a fragment thereof, fusing them with myeloma cells or the like to obtain hybridomas, and purifying an antibody produced by the hybridomas. An anti-podoplanin polyclonal antibody can be obtained from the serum of an animal immunized with podoplanin or fragment thereof. The anti-podoplanin antibody of the present invention may be obtained using sugar chain-added podoplanin when a non-human animal is immunized.

When the anti-podoplanin antibody of the present invention is produced using genetic recombination, it may be produced, for example, by transforming a proper host with an expression vector containing the nucleic acid of the present invention, culturing the resulting transformant under appropriate conditions to express an antibody, and then isolating and purifying the antibody by a known method.

Examples of the isolating and purifying method include an affinity column using protein A/G/L or the like, another chromatography column, a filter, ultrafiltration, salting-out, and dialysis. These methods may be used in combination as needed.

An antibody that binds to a predetermined epitope sequence can be prepared using a method known to those skilled in the art or a method based thereon. For example, a peptide containing an epitope sequence is fixed to a solid phase carrier and binding between the peptide and a plurality of antibodies is detected, by which an antibody that specifically binds to the epitope can be obtained.

As the "plurality of antibodies", antibodies obtained by immunizing an animal with an antigen protein or a partial peptide thereof may be used or an antibody library or an antibody fragment library constructed by phage display may be used. When a library constructed by phage display is used, it is also possible to fix a peptide containing an epitope sequence to a solid phase carrier, repeat panning, and thereby obtain an antibody that specifically binds to the epitope.

A human chimeric antibody and a human CDR grafted antibody can be prepared by cloning an antibody gene from mRNA of hybridomas producing an antibody of an animal other than human and linking it to a portion of a human antibody gene by using genetic recombination technology.

For example, for the preparation of a human chimeric antibody, cDNA is synthesized using reverse transcriptase from mRNA of hybridomas that produce a mouse antibody, the heavy chain variable region (VH) and the light chain variable region (LH) are cloned by PCR, and then the sequence is analyzed. Next, a 5' primer containing a leader sequence is prepared from an antibody base sequence having a high identity and then a portion of the cDNA from the signal sequence to the 3' end of the variable region is cloned by PCR using the 5' primer and the variable region 3' primer. On the other hand, the constant region of the heavy chain and the light chain of human IgG1 is cloned and for the heavy chain and the light chain, the mouse antibody-derived variable region and the human antibody-derived constant region are linked to each other by Overlapping Hanging using PCR and amplified. The DNA thus obtained is inserted into an appropriate vector, followed by transformation to obtain a human chimeric antibody.

For the preparation of a CDR grafted antibody, a human antibody variable region having the highest homology with a mouse antibody variable region to be used is selected and cloned and the base sequence of CDR is altered by site-selective mutagenesis using mega-primer method. When humanization of an amino acid sequence constituting a framework region disturbs specific binding to an antigen, an amino acid of a portion of the framework may be converted from a human type to a rat type.

A CDR composed of an amino acid sequence having deletion, substitution or addition of one or two amino acids in the original amino acid sequence or a CDR composed of an amino acid sequence having X % or more identity to the original amino acid sequence may be prepared using a known method such as site-specific mutagenesis, random mutagenesis, chain shuffling, or CDR walking.

It is well known to those skilled in the art that according to these methods, a CDR having more mature affinity can be obtained by displaying an antibody or antibody fragment having a variety of mutations in CDRs on the phage surface by phage display and screening using an antigen (for example, Wu et al., PNAS, 95:6037-6042 (1998); Schier, R. et al., J. Mol. Bio. 263:551-567 (1996); Schier, R. et al., J. Mol. Biol. 255:28-43 (1996); Yang, W. P. et al., J. Mol. Biol., 254:392-403 (1995)). The present invention also embraces an antibody containing a CDR matured in such a manner.

Additional examples of the antibody production method include the Adlib system for obtaining an antibody producing line from Trichostatin A-treated chicken B cell-derived DT40 cell line (Seo, H. et al., Nat. Biotechnol., 6:731-736, 2002) and a method of preparing a human antibody by immunizing KM mice obtained by destroying the mouse antibody gene and introducing a human antibody gene (Itoh, K. et al., Jpn. J. Cancer Res., 92:1313-1321, 2001; Koide, A. et al., J. Mol. Biol., 284:1141-1151, 1998). These methods can also be applied to production of the antibody of the present invention.

The antigen binding fragment of the anti-podoplanin antibody according to the present invention may be expressed by the above-described method using DNA encoding the fragment. Alternatively, a full-length antibody is obtained and then treated with an enzyme such as papain or pepsin to fragment it.

The anti-podoplanin antibody according to the present invention may be different in amino acid sequence, molecular weight, isoelectric point, presence/absence of sugar chains, conformation or the like, depending on the preparation method or purification method. However, the antibody thus obtained is embraced in the present invention insofar as it has a function equivalent to that of the antibody of the present invention. For example, when the antibody of the present invention is expressed in a prokaryotic cell such as E. coli, a methionine residue is added to the N-terminus of an amino acid sequence of an original antibody. The present invention also embraces such an antibody.

When the anti-podoplanin antibody of the present invention is an antibody having an N-linked sugar chain having no fucose bound to N-acetylglucosamine at the reducing end, such an antibody can be produced by a known method or a method based thereon. Such a method of producing an antibody is described in, for example, the pamphlet of WO2002/031140 or Japanese Patent Application Publication No. 2009-225781, the disclosure of which is incorporated herein by reference in its entirety.

Specifically, for example, an intended anti-podoplanin antibody can be obtained by transforming cells, whose enzymatic activity involved in the synthesis of GDP-fucose or α-1,6-fucosyltransferase activity has been reduced or deleted, by using a vector containing DNA encoding the anti-podoplanin antibody of the present invention, culturing the transformant thus obtained, and then purifying it. Examples of the enzyme involved in synthesis of GDP-fucose include GDP-mannose 4,6-dehydratase (GMP), GDP-keto-6-deoxymannose 3,5-epimerase, 4-reductase (Fx), and GDP-beta-L-fucose pyrophosphorylase (GFPP).

Here, the cells are not particularly limited, but are preferably mammalian cells. For example, CHO cells having the above-described enzymatic activity reduced or deleted may be used.

Although the antibody composition obtained by the above method may contain an antibody having fucose bound to N-acetylglucosamine at the reducing end, a proportion of the fucose-bound antibody is 20 wt % or less, preferably 10 wt % or less, more preferably 5 wt % or less, most preferably 3 wt % or less, each based on the total weight of the antibodies.

Further, the antibody having an N-linked sugar chain having no fucose bound to N-acetylglucosamine at the reducing end may also be obtained by introducing a vector containing DNA encoding the anti-podoplanin antibody of the present invention into insect eggs, hatching and growing the insects, and crossbreeding them if necessary to produce a transgenic insect, and extracting an anti-podoplanin antibody from the transgenic insect or a secretion thereof. As the insect, a silkworm may be used. In this case, the antibody can be extracted from silkworm cocoons.

Although the antibody composition obtained using the above method may also contain an antibody having fucose bound to N-acetylglucosamine at the reducing end, a proportion of the fucose-bound antibody is 20 wt % or less, preferably 10 wt % or less, more preferably 5 wt % or less, most preferably 3 wt % or less, each based on the total weight of the antibodies.

(Activity of the Antibody of the Present Invention)

The drug efficacy mechanism of antibody drugs is based on two biological activities of antibodies. One of them is a target antigen-specific binding activity, which is an activity neutralizing the function of a target antigen molecule through binding thereto. Functional neutralization of the target antigen molecule is exhibited through the Fab region.

The other one is a biological activity of an antibody called "effector activity". The effector activity is exhibited as antibody-dependent cellular cytotoxicity (ADCC), complement-dependent cytotoxicity (CDC), direct induction of apoptosis, or the like through an Fc region of an antibody.

The activities of the anti-podoplanin antibody of the present invention can be measured in the following methods.

(1) Binding Activity

The binding activity of an antibody can be measured by a known method, for example, ELISA (enzyme-linked immunosorbent assay), EIA (enzyme immunoassay), RIA (radioimmunoassay), a fluorescent antibody method, or an FACS method.

(2) ADCC Activity

The term "ADCC activity" means a target cell damaging activity by, when the antibody of the present invention binds to the cell surface antigen of target cells, Fcγ receptor-bearing cells (effector cells) bound to the Fc portion of the antibody through its Fcγ receptor.

The ADCC activity can be known by mixing podoplanin-expressing target cells, effector cells, and the antibody of the present invention, and measuring the degree of ADCC. As the effector cells, for example, mouse splenocytes, or monocytes isolated from the human peripheral blood or bone marrow may be used. As the target cells, for example, podoplanin-positive mesothelioma cells or podoplanin-positive glioblastoma cells may be used. The activity can be measured by labeling target cells with $^{51}$Cr or the like in advance, adding the antibody of the present invention to the resulting cells, incubating the resulting mixture, adding effector cells to the target cells at a ratio adequate therefor, incubating the resulting mixture, collecting the supernatant, and then counting the label in the supernatant.

(3) CDC Activity

The term "CDC activity" means cellular cytotoxicity caused by a complement system.

The CDC activity can be measured as in the ADCC activity test except for the use of a complement instead of effector cells.

(4) Tumor Growth Inhibitory Activity

The tumor growth inhibitory activity can be measured using a tumor model animal. For example, a tumor is subcutaneously implanted into a mouse and the antibody of the present invention is administered thereto. A tumor growth inhibitory effect can be measured by comparing the volume of the tumor tissue between a non-administered group and an administered group.

The tumor growth inhibitory activity in the present invention may result from inhibition of growth of individual cells or may result from induction of apoptosis.

(Pharmaceutical Composition)

The anti-podoplanin antibody of the present invention may be used for prevention or treatment of cancer that expresses a podoplanin antibody. A pharmaceutical composition according to one aspect of the present invention contains, as an effective ingredient, the cancer cell-specific anti-podoplanin antibody or antigen-binding fragment thereof according to the present invention and further contains a pharmacologically acceptable carrier or additive.

The cancer cell-specific anti-podoplanin antibody of the present invention may be used for delivery of a drug targeting cancer cells. A pharmaceutical composition according to another aspect of the present invention, contains, as an effective ingredient, an anti-podoplanin antibody or antigen-binding fragment thereof to which the above-described substance having anti-cancer activity has been bound and it further contains a pharmacologically acceptable carrier or additive.

Examples of the carrier and additive include, but are not limited to, water, saline, phosphate buffer, dextrose, pharmaceutically acceptable organic solvents such as glycerol and ethanol, collagen, polyvinyl alcohol, polyvinylpyrrolidone, a carboxy vinyl polymer, carboxymethylcellulose sodium, sodium polyacrylate, sodium alginate, water-soluble dextran, sodium carboxymethyl starch, pectin, methylcellulose, ethylcellulose, xanthan gum, gum arabic, casein, agar, polyethylene glycol, diglycerin, glycerin, propylene glycol, petrolatum, paraffin, stearyl alcohol, stearic acid, human serum albumin, mannitol, sorbitol, lactose, and surfactants.

The pharmaceutical composition of the present invention may be provided in a variety of forms, for example, a solution (for example, an injection), a dispersion, a suspension, a tablet, a pill, a powder, or a suppository. A preferred embodiment is an injection, and parenteral administration (for example, intravenously, transdermally, intraperitoneally, or intramuscularly) is preferred.

The pharmaceutical composition of the present invention is effective for the treatment of diseases in which podoplanin is involved, particularly, cancers.

Examples of the cancers in which podoplanin is involved include malignant brain tumor, malignant mesothelioma, testicular tumor, ovarian cancer, and squamous cell cancer. Examples of the squamous cell cancer described herein include, but are not limited to, oral cancer, pharyngeal cancer, laryngeal cancer, esophageal cancer, lung cancer, skin cancer, and uterine cervical cancer. The cancer cell-specific anti-podoplanin antibody of the present invention is particularly useful for these cancers.

The present invention also embraces a treatment method of a disease in which podoplanin is involved, including administering a therapeutically effective amount of the antibody of the present invention.

The term "therapeutically effective amount" as used herein means an amount of an acting substance which alleviates one or more symptoms of the disease to be treated to a certain extent. For an anti-cancer agent, it means an amount that causes at least one of reduction of a tumor size; inhibition of tumor metastasis (retardation or stopping); inhibition of tumor growth (retardation or stopping), and alleviation of one or more symptoms associated with cancer.

Specifically, the dose of the antibody of the present invention may be in a range of, for example, from 0.025 to 50 mg/kg, preferably from 0.1 to 50 mg/kg, more preferably from 0.1 to 25 mg/kg, still more preferably from 0.1 to 10 mg/kg or from 0.1 to 3 mg/kg, but is not limited thereto.

(Marker and Diagnostic Agent)

As described above, podoplanin is expressed highly in certain cancer cells. Therefore, the anti-podoplanin antibody of the present invention is useful in the diagnosis of cancers, particularly cancers in which podoplanin is highly expressed, such as malignant brain tumor, malignant mesothelioma, testicular tumor, ovarian cancer, and a variety of squamous cell cancers (oral cancer, pharyngeal cancer, laryngeal cancer, esophageal cancer, lung cancer, skin cancer, and uterine cervical cancer). The anti-podoplanin antibody of the present invention binds in a cancer cell-specific manner so that it is particularly useful for diagnosis.

The present invention embraces a diagnostic agent of cancer containing the antibody of the present invention, use of the antibody for diagnosis of cancer, and a diagnostic method of cancer using the antibody of the present invention.

All the disclosed patent documents and non-patent documents to be cited herein are incorporated herein as an entirety by reference.

EXAMPLES

The present invention will hereinafter be described specifically based on embodiments. The present invention is not limited to or by them. Those skilled in the art can change the present invention into various aspects without departing from the gist of the present invention. Such a change is also embraced within the scope of the present invention.

1. Gene Introduction of Human Podoplanin into Brain Tumor Cell Line and Analysis Using Lectin Microarray It is known that a carbohydrate antigen specific to brain tumor has been expressed in brain tumor cell line LN229 (purchased from ATCC). (Expression of highly sulfated keratan sulfate synthesized in human glioblastoma cells. Hayatsu N, et al., Biochem Biophys Res Commun. 2008 4; 368(2):217-22; Increased expression of highly sulfated keratan sulfate synthesized in malignant astrocytic tumors. Kato Y, et al., Biochem Biophys Res Commun. 2008 16; 369(4): 1041-6.).

A high expression strain of podoplanin (LN229/hPDPN) was established by gene introduction of the full-length human podoplanin into LN229 cells by lipofection. Described specifically, LN229 cells are cultured semiconfluently in a 10-cm dish. Immediately before lipofection, the medium is replaced with an OPTI-MEM medium (product of Life Technologies). After 15 ug of DNA is suspended in 3 mL of the OPTI-MEM medium, the resulting suspension is mixed successively with 15 µl of Plus reagent (product of Life Technologies) and 37.5 µl of Lipofectamin LTX reagent (product of Life Technologies). The resulting mixture is reacted at room temperature for 30 minutes. The suspension thus obtained is added to the cells. Six hours later, the medium is replaced by 10% FAB/DMEM. Twenty four hours later, G418 (product of Wako Pure Chemicals) is added to give a concentration of 1 mg/ml and only expression cells are selected. As control cells, a cell line (CHO/ hPDPN) obtained by introducing the full-length human podoplanin into CHO cells are used (Kato Y., et al., J Biol. Chem. 278, 51599-51605, 2003.).

As described above, human podoplanin genes were expressed in LN229 cells and CHO cells, respectively and they were purified using a FLAG tag added to the C terminal. For analysis using a lectin microarray (LecChip (trade mark); product of Glycotechnica), they were adjusted with PBS to give a concentration of 50 µg/ml. After 20 µl of the sample solutions thus prepared and Cy3 Mono-Reactive dye 100 ig labeling (Cy3 Mono-Reactive dye pack (product of GE Healthcare), dispensed for 100 µg labeling) were mixed, the resulting mixture was reacted at room temperature for one hour in a dark place. Desalting columns (Zeba™ Spin Desalting Columns, 7K MWCO, product of Thermo Scientific) were centrifuged at 1,500×g for one minute at 4° C. TBS (pH7.5, 300 µL) was applied to the desalting columns, followed by centrifugation at 1,500×g for one minute at 4° C. (column washing). Column washing was performed twice further. After application of a mixture of 20 µl of the sample solutions and Cy3 Mono-Reactive dye 100 µg labeling1 and 25 µL of TBS to the desalting columns, centrifugation was performed at 1,500×g for 2 minutes at 4° C. to remove an unreacted portion of Cy3. The samples were each applied with 455 µL of Probing Solution (product of Glycotechnica) to give 500 µL/tube (concentration=2 µg/mL). Further, by using Probing Solution, 7-point dilution series were prepared at a dilution ratio of ½. LecChip (trade mark) was washed three times with Probing Solution (100 µL/well) and then the samples (100 µL/well) thus prepared were applied. The LecChip (trade mark) was reacted at 20° C. for 17 hours or more. The LecChip (trade mark) in a liquid phase state with which the samples were being reacted was measured using a GlycoStation (trade mark) Reader 1200 (product of Glycotechnica) (measurement conditions: integration: 4 times, exposure time: 133 mSec, and camera gain: 85, 95, 105, 115, 125).

Figure 5:
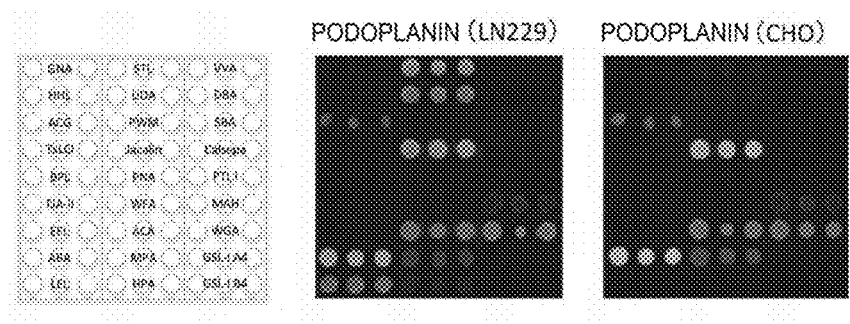
FIG. 5 shows the lectin microarray analysis results using antibodies purified from LN229/hPDPN and CHO/hPDPN with FLAG tags.

FIG. 5 shows the results at the camera gain 115 and protein concentration of 62.5 ng/ml. As shown therein, both human podoplanin expressed in LN229 and human podoplanin expressed in CHO showed reactivity with four lectins (Jacalin, *Agaricus bisporus* agglutinin (ABA), Jacalin, *Amaranthus caudatus* agglutinin (ACA), and *Maclura pomifera* agglutinin (MPA)) having a binding property to Corel±sialic acid (a Corel structure added with sialic acid, or only a Corel structure) and two lectins (*Maackia amurensis* hemagglutinin (MAH) and Wheat germ agglutinin (WGA)) having a binding property to sialo-mucin. On the other hand, only human podoplanin expressed in LN229 showed reactivity with three lectins (*Lycipersicon esculentum* lectin (LEL), *Solanum tuberosum* lectin (STL), *Urtica dioica* agglutinin (UDA)) having a binding property to a polylactosamine structure, that is, a Galβ1-4GlcNAc repeated structure. The above results have suggested that human podoplanin expressed in LN229 has a cancer cell-specific sugar-chain structure added thereto.

2. Immunoprecipitation and Western Blot Analysis

Since human podoplanin of LN229/hPDPN and CHO/hPDPN have, at the C terminal thereof, a FLAG tag, immunoprecipitation was performed using an antibody (M2 antibody, product of Sigma Aldrich) against the FLAG tag, followed by western blot analysis.

LN229/hPDPN and CHO/hPDPN cell lysates, each 100 µg, were added to M2 antibody beads against the FLA tag and reacted at 4 degrees for one hour. The reaction product was eluted with 100 ul of FLAG peptide (100 µg/ml) and 5 µl portions were boiled at 100 degrees together with 2× sample buffers (without 2ME). The 10 µl portions of the samples thus prepared were applied to a gel, followed by SDS-PAGE electrophoresis. After transfer to a PVDF membrane, blocking was performed at room temperature for one hour with 4% skim milk/0.05% Tween in PBS (blocking buffer). A monoclonal antibody 5D4 (product of Seikagaku Corporation) against highly sulfated keratin sulfate was diluted with a blocking buffer at a concentration of 2 µg/ml and reacted at room temperature for one hour. Then, a secondary antibody (anti-mouse IgG-HRP: product of Dako, 1:2,000 dilution) was reacted at room temperature for 30 minutes and color development was caused using ECL-plus (product of Thermo Fisher). For detection, EZ-Capture II (product of Atto Corporation) was used.

Figure 6:
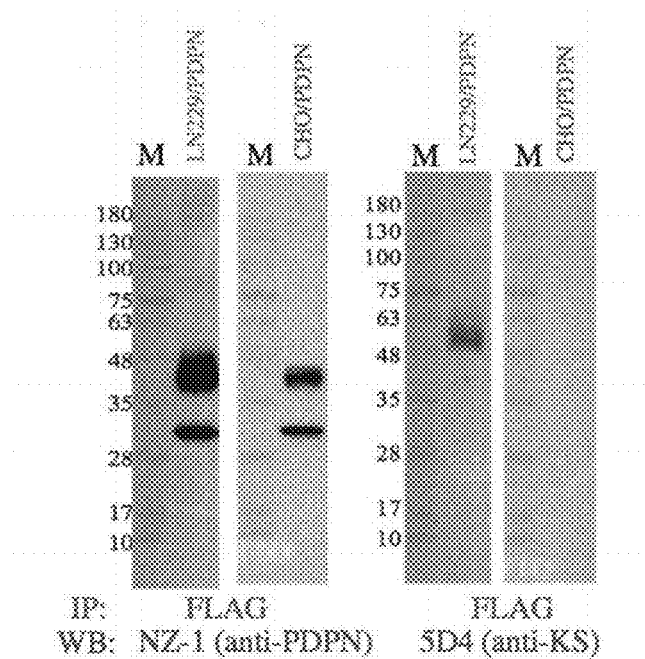
FIG. 6 shows the results of western blot of human podoplanins which is immunoprecipitated from LN229/hPDPN and CHO/hPDPN by using an antibody (M2) against FLAG tag, with an antibody (5D4 antibody) against highly sulfated keratan sulfate.

The results are shown in FIG. 6. The human podoplanin obtained by immunoprecipitation of LN229/hPDPN and CHO/hPDPN while using the antibody (M2) against FLAG tag was recognized by an NZ-1 antibody. Further, not only the podoplanin derived from LN229/hPDPN was recognized by a 5D4 antibody but also it had a molecular weight higher than the molecular weight of the typical podoplanin. On the other hand, the podoplanin derived from CHO/hPDPN was not recognized by the 5D4 antibody. It becomes apparent from the above findings that the podoplanin expressed in LN229 cells has been added with tumor-specific and highly-sulfated keratin sulfate recognized by the 5D4 antibody.

3. Preparation of Cancer-Cell Specific Anti-Podoplanin Antibody

Balb/c mice were each immunized with $1 \times 10^8$ LN229/hPDPN cells four times in total (once 10 days). An antibody reactive with a recombinant protein purified from the cancer cell line was screened by ELISA (Enzyme-linked immunosorbent assay).

The recombinant protein is purified as follows. The LN229/hPDPN cells are statically cultured and 10 g of cells was collected in total. To the resulting cells is added 10 ml of a 0.5% Triton/PBS solution and the cells are solubilized on ice by pipetting. The solution obtained by solubilization is centrifuged at 15,000 rpm for 30 minutes. The supernatant is added to 1 ml of an anti-FLAG antibody (M2) affinity column (product of Sigma Aldrich) and the resulting mixture is reacted at 4 degrees for 18 hours. The reaction product is washed three times with 10 ml of PBS. The recombinant protein adsorbed to the column is eluted by adding 0.1 mg/ml of FLAG peptide (product of Sigma Aldrich) in 1-ml portions. The absorbance at OD280 is measured, the fraction thus eluted is concentrated and the final concentration is adjusted to 0.1 mg/ml.

ELISA is performed as follows. Podoplanin purified to have 1 µg/ml is immobilized on a 96 well plate (Nunc MaxiSorp; product of Thermo Fisher) at 37 degrees for 30 minutes, followed by blocking at 37 degrees for 30 minutes by using SuperBlock/PBST (product of Thermo Fisher). Similarly, anti-mouse IgG-HRP (product of Dako), that is, a mouse hybridoma-derived supernatant is reacted successively under conditions of 37 degrees and 30 minutes and color is developed using TMB-Ultra (product of Thermo Fisher). The absorbance (OD: 655 nm) is measured using a microplate reader (product of Bio-Rad).

The cancer cell-specific anti-podoplanin antibody selected is named LpMab-23.

4. Determination of Amino Acid Sequence of Anti-Podoplanin Antibody and Base Sequence of Antibody Gene From $1 \times 10^6$ hybridoma cells of the anti-podoplanin antibody LpMab-23, a total RNA was extracted using a QIAGEN RNeasy mini kit (product of Qlagen). From 1 µg of the total RNA, cDNA synthesis was performed using a Super- Script III First-Strand Syntheses kit (product of QIAGEN). The cDNA was used as a template in the following experiment.

For amplification of the H chain, the following primers were used.

```
LpMab-23
                                          (SEQ ID NO: 81)
LpMab-23HatgS: aataagcttAGCATGGCTGTCCTGGTGCT (SEQ ID NO: 82)
mIgG1terAS: ggcggccgcTCATTTACCAGGAGAGTGGGAGA
```

The PCR reaction was performed using QIAGEN HotStar Taq (product of Qiagen). The reaction was made under the following temperature conditions: first at 95° C. for 15 minutes, next 35 cycles of 94° C. for 30 seconds, 50° C. for 30 seconds, and 72° C. for 1 minute and 40 seconds, and lastly 72° C. for 10 minutes. The amplified PCR product was purified using a QIAGEN PCR purification kit. After subcloning into pcDNA3.1, the base sequence was determined from a vector primer.

Amplification of the L chain was performed using the following primers.

```
LpMab-23
                                          (SEQ ID NO: 83)
LpMab-23LatgS: aataagcttAAAATGATGAGTCCTGCCCAG moIgCKterAS:
                                          (SEQ ID NO: 84)
ggcggccgcCTAACACTCATTCCTGTTGAA
```

The PCR reaction was performed using QIAGEN HotStar Taq. The reaction was made under the following temperature conditions: first at 95° C. for 15 minutes, next 35 cycles of 94° C. for 30 seconds, 53° C. for 30 seconds, and 72° C. for 1 minute, and lastly 72° C. for 10 minutes. The amplified PCR product was purified using a QIAGEN PCR purification kit. After subcloning into pcDNA3.1, the base sequence was determined from a vector primer. The amino acid sequence was predicted from the base sequence.

The amino acid sequences of heavy chains CDR1 to 3 and light chains CDR1 to 3 of LpMab-23 were as shown by SEQ ID NOS: 71 to 76.

The heavy chain DNA sequence of LpMab-23 was as shown by SEQ ID NO: 80.

The light chain DNA sequence of LpMab-23 was as shown by SEQ ID NO: 79.

The heavy chain amino acid sequence of LpMab-23 was as shown by SEQ ID NO: 78.

The light chain amino acid sequence of LpMab-23 was as shown by SEQ ID NO: 77.

5. Flow Cytometry

Reactivity of the anti-podoplanin antibody (LpMab-23) with a podoplanin expression strain was studied by flow cytometry. First, LpMab-23 (1 μg/ml) was reacted at 4° C. for 30 minutes with various human podoplanin-expressed cell lines and then reacted further with an anti-mouse IgG-FITC antibody (product of Life Technologies) at 4° C. for 30 minutes. As a positive control, LpMab-7, an anti-podoplanin antibody, was used and as a negative control, only a secondary antibody was used. Fluorescence intensity was measured using EC800 (product of Sony).

Figure 7:
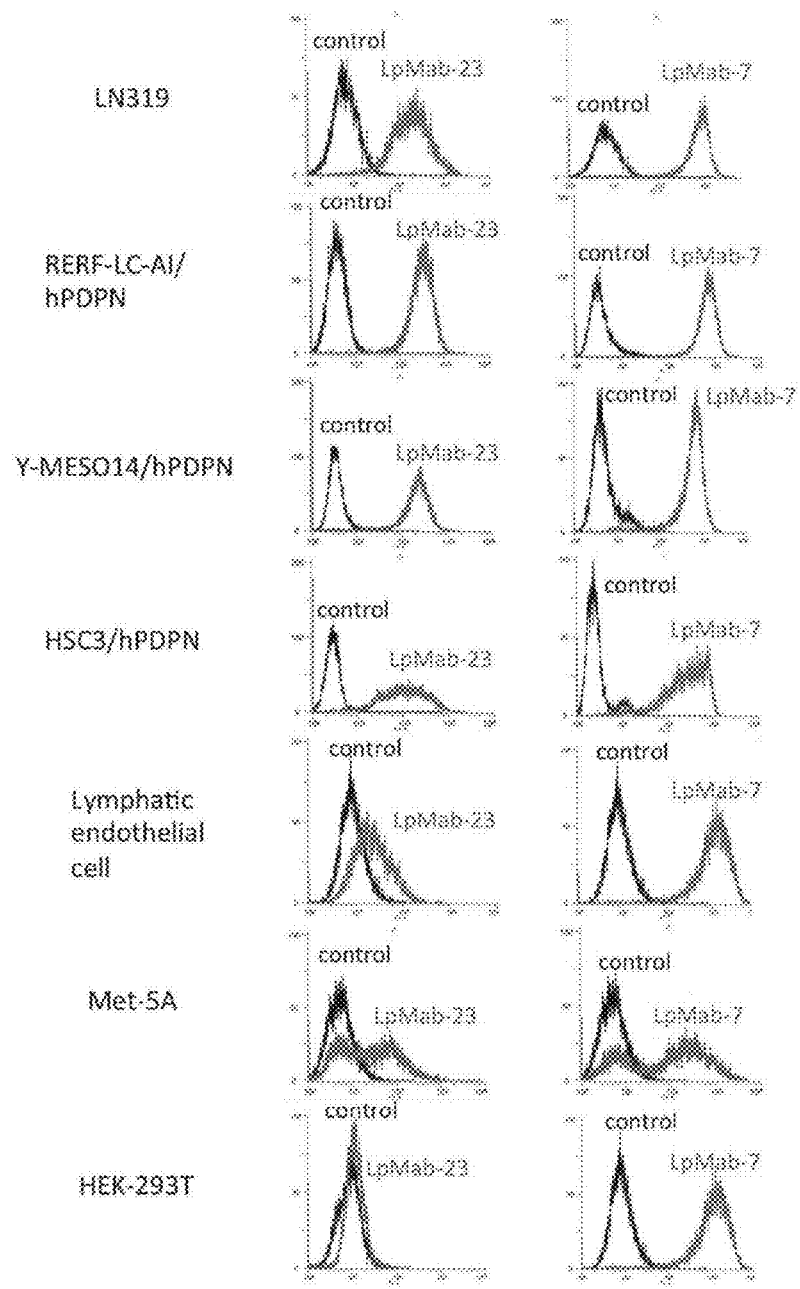
FIG. 7 shows the results of flow cytometry using glioblastoma (LN319), lung squamous cell cancer (RERF-LC-AI/hPDPN), malignant mesothelioma (Y-MESO14/hPDPN), oral cancer (HSC3/hPDPN), lymphatic epithelial cells, normal mesothelial cells (Met-5A), and renal epithelial cells (HEK-293T).

The results are shown in FIG. 7. The LpMab-23 antibody showed high reactivity with podoplanin on cancer cells such as glioblastoma (LN319), squamous cell cancer (RERF-LC-AI-hPDPN), malignant mesothelioma (Y-MESO14-hP-DPN), or oral cancer (HSC3/hPDPN) cells. On the other hand, it showed weak reactivity with lymphatic epithelial cells, normal mesothelial cells (Met-5A), and renal epithelial cells (HEK-293T).

Figure 9:
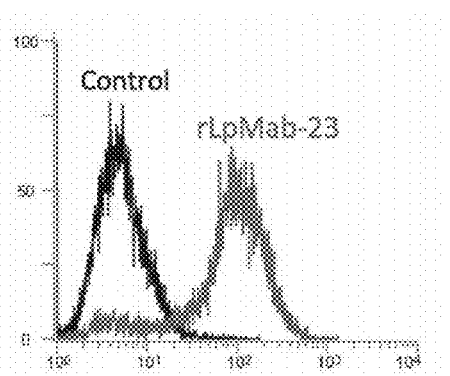
FIG. 9 shows the results of flow cytometry of the recombinant antibody (rLpMab-23) against LN319 cells.

Expression plasmids were prepared by TA cloning of the full-length H chain and L chain of LpMab-23 into a pcDNA3.1 vector (product of Life Technologies). The resulting plasmids were each introduced into a CHO cell line by lipofection to express recombinant antibodies. The recombinant antibodies (rLpMab-23) in the culture supernatant (collected one day after gene introduction) were each reacted with LN319 cells, a podoplanin expression strain, at 4° C. for 30 minutes and then reacted further with an anti-mouse IgG-FITC antibody (product of Life Technologies) at 4° C. for 30 minutes. As a negative control, only a secondary antibody was used. Fluorescence intensity was measured using Cell Analyzer EC800 (product of Sony). As a result, as shown in FIG. 9, rLpMab-23 showed good reactivity in flow cytometry using the LN319 cells. It has therefore been verified that the H chain and L chain sequences of LpMab-23 shown in SEQ ID NOS: from 77 to 11 are correct.

Figure 10:
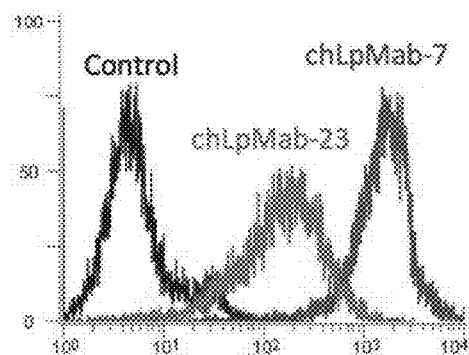
FIG. 10 shows the results of flow cytometry of the human chimeric antibody (chLpMab-23) of LpMab-23 by using LN319 cells.

Expression plasmids of a human chimeric LpMab-23 antibody (chLpMab-23) were prepared by incorporating a variable region of the H chain and the L chain of LpMab-23 in a pcDNA3.1 vector having therein a human IgG1 constant region. They were introduced into a CHO cell line by lipofection and recombinant antibodies of chLpMab-23 were expressed in the culture supernatant. One day after gene introduction, the culture supernatant was collected. It was reacted with LN319 cells at 4° C. for 30 minutes and then reacted further with an anti-human IgG-FITC antibody (product of Life Technologies) at 4° C. for 30 minutes. As a positive control, human chimeric LpMab-7 (chLpMab-7) was used and as a negative control, only a secondary antibody was used. Fluorescence intensity was measured using Cell Analyzer EC800 (product of Sony). As a result, as shown in FIG. 10, the chLpMab-23 antibody showed high reactivity with podoplanin of glioblastoma (LN319).

The heavy chain amino acid sequence, the light chain amino acid sequence, the heavy chain DNA sequence, and the light chain DNA acid sequence of the chLpMab-23 antibody are shown in SEQ ID NOS: 85 to 88.

6. Immunohistostaining

Various paraffin sections were deparaffined in xylene and ethanol solutions. Antigen activation operation was not performed. The endogenous peroxidase was inactivated with 3% $H_2O_2$. Blocking was performed at room temperature for 10 minutes with SuperBlock (product of Thermo Fisher) and the primary antibody was reacted at room temperature for one hour. After amplification using a LSAB kit (product of Dako), color was developed using DAB (product of Dako).

Figure 8:
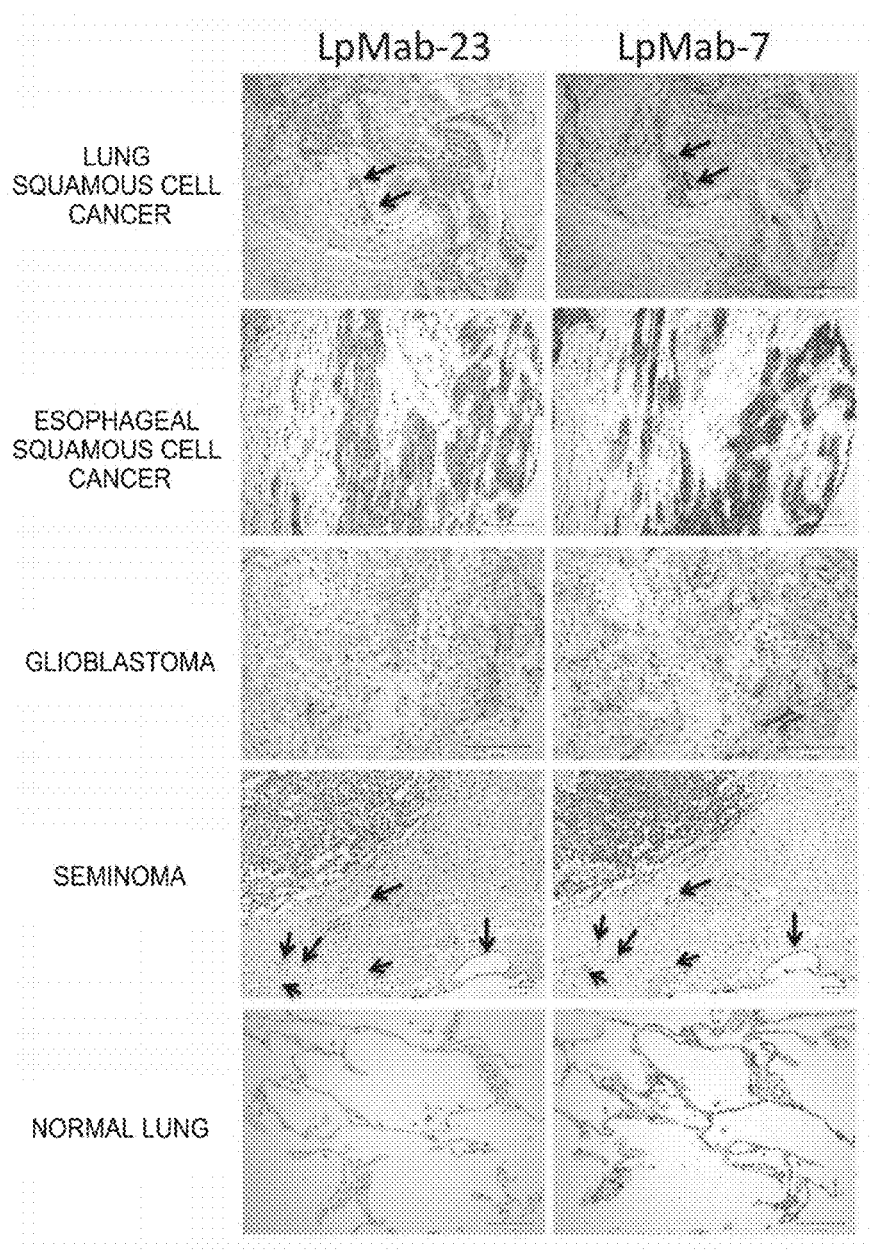
FIG. 8 shows the results of immunohistostaining of lung squamous cell cancer, esophageal squamous cell cancer, glioblastoma, seminoma, and normal lung with LpMab-23.

Staining results of LpMab-23 are shown in FIG. 8. LpMab-23 is a cancer cell-specific antibody. Described specifically, LpMab-23 stained a tumor portion of lung squamous cell cancer, esophagus squamous cell cancer, glioblastoma, and seminoma, but did not stain the lymphatic endothelial cells (arrow) at all. LpMab-7 used as a positive control reacted with both cancer cells and lymphatic epithelial cells. LpMab-23 did not react with alveolar epithelial cells, while LpMab-7 stained alveolar epithelial cells.

ABSTRACT

An object of the present invention 2 is to provide a cancer cell-specific anti-podoplanin antibody useful as a drug, a diagnostic agent, and a reagent and a strategic preparation method thereof. The present invention 2 provides a method of producing an antibody against podoplanin expressed in a cancer cell-specific manner which method includes a step of introducing a nucleic acid encoding podoplanin into cells that express a cancer cell-specific sugar-chain structure, a step of immunizing a non-human mammal with the cells to obtain antibodies, and a step of selecting an antibody reactive with cancer cell-specific podoplanin by primary screening of the antibodies.

Method of Producing Monoclonal Antibody

TECHNICAL FIELD

The present invention relates to a method of producing an active monoclonal antibody through reactivation of hybridomas.

BACKGROUND ART

A monoclonal antibody is prepared by fusing antibody producing cells of an experimental animal (usually, a mouse) and myeloma cells to prepare hybridomas and screening the hybridomas to select a strain producing an intended antibody. Georges J. F. Kohler and Cesar Milstein who invented a preparation method of a monoclonal antibody in 1975 won the Nobel Prize in Physiology or Medicine in 1984. For screening of hybridomas that secrete an intended monoclonal antibody, ELISA is typically employed and wells providing high activity are subjected to single cell cloning. As a result, fusion cells in the wells that provide high activity are hybridomas producing the intended monoclonal antibody.

Antibodies produced by the hybridomas obtained by single cell cloning however often fail to reproduce the activity obtained in first ELISA. There are presumed to be two reasons. First one is that hybridomas that are producing an intended antibody stop their growth when they are placed in one well (of, for example, a 96-well plate) and a clone cannot be established. The second one is that the although a clone can be obtained, an intended antibody gene is lost during subcloning from a 96-well plate to a 24-well plate, a 6-well plate, and a 10-cm dish, making it difficult to establish them as hybridomas.

The reason why the activity is not reproduced in single cell cloning has not yet been elucidated at all, but is presumed that an antibody gene intrinsic to myeloma cells may exclude an intended antibody gene introduced later by cell fusion. There is also a possibility that either an antibody gene derived from myeloma cells or an intended antibody gene derived from antibody producing cells is excluded stochastically. Anyway, the intended antibody gene tends to be excluded because it is unnecessary for the survival of hybridomas.

SUMMARY

Technical Problem

An object of the present invention is to provide a method of preparing an active antibody by improving the antibody producing ability of hybridomas, in particular, recovering the antibody producing ability of hybridomas that do not reproduce activity in single cell cloning or hybridomas that have stopped production of an active antibody during subculture.

Solution to Problem

With a view to achieving the above-described object, the present inventors have investigated and as a result, thought that supposing that an intended antibody gene is excluded stochastically during preparation of hybridomas, by adding another cell fusion operation to hybridomas of antibody producing cells and myeloma cells, there is a possibility of an antibody gene derived from myeloma cells being excluded and an intended antibody gene remaining in a second cell fusion step.

It has been confirmed that hybridomas producing an active antibody can be obtained by fusing hybridomas obtained by fusing antibody producing cells with myeloma cells with hybridoma or myeloma cells and performing single cell cloning using the resulting hybridomas, leading to the completion of the present invention.

Described specifically, the present invention relates to:

[B1] a method of producing an antibody, including:
    a cell fusion step for fusing first hybridomas with second hybridomas or myeloma cells, and
    a step of obtaining a monoclonal antibody from the fusion cells;

[B2] the method of producing an antibody as described above in [B1], wherein the first hybridomas are hybridomas having reduced ability of active monoclonal antibody production;

[B3] the method of producing an antibody as described above in [B1] or [B2], wherein the second hybridomas are derived from a line the same as that of the first hybridomas;

[B4] the method described above in any one of [B1] to [B3], wherein the cell fusion step is performed in the presence of inactivated Sendai virus or polyethylene glycol;

[B5] the method as described above in [B4], wherein the inactivated Sendai virus is an inactivated Sendai virus envelope;

[B6] the method as described above in any one of [B1] to [B5], wherein the myeloma cells are P3U1 cells; and

[B7] the method as described above in any one of [B1] to [B6], wherein in the cell fusion step, a ratio of the number of the first hybridomas to that of the myeloma cells is set to fall within a range of from 1:10 to 10:1.

Advantageous Effects of Invention

The present invention makes it possible to enhance the antibody producing ability of hybridomas by fusing them with other hybridomas or myeloma. Particularly, the method of the present invention makes it possible to re-activate hybridomas whose activity has not been reproduced in single cell cloning or hybridomas which have stopped production of an active antibody during subculturing and thereby prepare an active monoclonal antibody.

DESCRIPTION OF EMBODIMENTS

A method of producing an antibody according to one aspect of the present invention includes a cell fusion step for fusing first hybridomas with second hybridomas, and a step of purifying a monoclonal antibody from the fusion cells thus obtained.

The term "hybridomas" as used herein means proliferable monoclonal antibody producing cells obtained by fusing antibody producing cells and proliferable tumor cells. The antibody producing cells used are, for example, B cells, spleen cells, lympho node cells, thymocytes, peripheral blood cells of a non-human mammal immunized with an intended antigen. These cells can be obtained by peritoneally or subcutaneously injecting an immunized animal with an antigen to administer the antigen, finding an increase in the level of an intended antibody in the serum meaning immunization, and collecting antibody producing cells from the immunized animal. More specifically, they can be obtained by excising from the immunized animal the spleen, lympho node, thymus, or peripheral blood and fracturing, filtering, or centrifuging the tissue thus excised.

The non-human mammal used herein is not particularly limited but examples include mice, guinea pigs, hamsters, rats, rabbits, goats, pigs, sheep, and horses. As the non-human mammal, a transgenic non-human mammal created to produce an antibody derived from another animal may be used.

As the tumor cells used for hybridomas, myeloma cells (myeloma cells) derived from non-human mammal are used. Examples of the myeloma cells include, but are not limited to, Sp2/0, SP2/0-Ag14, P3X63Ag8, P3X63Ag8U1 (P3U1), NS-1, and P3X63Ag8.653.

The antibody producing cells can be fused with the tumor cells by a known method. For example, Sendai virus, polyethylene glycol (PEG), or a method electrically inducing cell fusion can be used. The antibody producing cells and the tumor cells may be derived from animals of the same kind or animals of a different kind. The hybridomas thus prepared are selected by culturing in a typical selection medium, for example, a HAT medium (a medium containing hypoxanthine, aminopterin, and thymidine). Culturing in the HAT medium is continued for a period (typically, from several days to several weeks) sufficient for killing cells (non-fusion cells) other than the intended hybridomas.

The first hybridomas may be hybridomas having reduced ability of active monoclonal antibody production. The term "hybridomas having reduced ability of active monoclonal antibody production" means hybridomas which have once been found to produce an active antibody but have lost the whole or part of its active monoclonal antibody producing ability. The reduced ability of active monoclonal antibody production may be caused by single cell cloning or subculturing performed a plurality of times, but the reason is not limited to them.

A deterioration degree of the active antibody producing ability is not particularly limited. Examples of such hybridomas include hybridomas that do not allow purification of an intended monoclonal antibody therefrom, hybridomas having a reduced antibody production amount, hybridomas capable of producing only an inactive or activity-reduced monoclonal antibody though the production amount of the antibody is kept same as that in the beginning, hybridomas having cell growth ability less than that at the time of establishment, hybridomas whose growth has been retarded or stopped by exchange of a medium into a serum-free medium, a low-protein medium, a chemically synthesized medium, or the like, hybridomas that cannot prepare mouse ascites, and hybridomas that can produce mouse ascites but do not produce an intended antibody in the ascites.

As the second hybridomas used herein, any hybridomas are usable. Examples include hybridomas derived from a line same as that for the first hybridomas and hybridomas that produce another antibody and have reduced active antibody producing ability. The second hybridomas may have reduced active antibody producing ability or may still have the original antibody producing ability.

The cell fusion step for fusing the first hybridomas with the second hybridomas can be performed, as in the above-described method of producing hybridomas, using inactivated Sendai virus or PEG. The inactivated Sendai virus may be a Sendai virus envelope. Although the molecular weight of PEG is not particularly limited, for example, PEG having a molecular weight of from about 1000 to 5000 or that having a molecular weight of from 1500 to 4500 may be used. The cell fusion step may be performed using commercially-available inactivated Sendai virus or PEG in accordance with a protocol attached thereto.

Although a ratio of the number of the first hybridomas to the second hybridomas is not particularly limited, it can be set, for example, at from 1:10 to 10:1. Alternatively, it can be set at from about 1:5 to 5:1, from about 1:3 to 3:1, from about 1:2 to 2:1, or from about 1:1.

Cell fusion using inactivated Sendai virus is ordinarily performed in the following procedure. Cells to be fused are prepared, mixed in a conical tube, and centrifuged. The supernatant is then removed. An ice-cooled buffer for fusion is added and the resulting mixture is converted into a uniform suspension by pipetting. To the resulting suspension is added an ice-cooled Sendai virus suspension and the resulting mixture is left at rest on ice for 5 minutes. The mixture is centrifuged at 1,000 rpm for 5 minutes, followed by incubation as is at 37 degree for 15 minutes. The cells are seeded on a 96-well plate and from the next day, cultured after exchange for a HAT medium.

The cell fusion using PEG is ordinarily performed in the following procedure. The cells to be fused are prepared and mixed. A PEG solution is added slowly to the cells while stirring. A medium is added to the cells slowly while stirring further. After centrifugation, the supernatant is removed. A medium is added, the cells are seeded on a 96-well plate, and they are cultured from the next day in a HAT medium substituted for the medium.

The step of obtaining a monoclonal antibody from the thus-obtained fusion cells of the first hybridomas and the second hybridomas can be performed in accordance with a known method for obtaining an antibody from typical hybridomas. The term "obtain an antibody" as used herein embraces not only purification of an antibody but also collection of a culture supernatant containing the antibody.

Purification of an antibody is achieved, for example, by culturing cells in a HAT medium, carrying out limiting dilution after cells (non-fusion cells) other than hybridomas are killed, and performing single cell cloning of hybridomas that produce an intended antibody. Then, screening of hybridomas that produce an intended antibody can be performed by the screening method known in the art such as immune thin-layer chromatography, ELISA, RIA, BIAcore, or fluorescent antibody method.

The monoclonal antibody can be purified, for example, by ammonium sulfate precipitation, a protein A or protein G column, DEAE ion exchange chromatography, or affinity column.

The hybridomas thus prepared can produce an active monoclonal antibody instead of the monoclonal antibody produced using the first hybridomas having reduced production ability.

A method of producing an antibody according to another aspect of the present invention includes a cell fusion step for fusing first hybridomas with myeloma cells and a step of purifying a monoclonal antibody from the resulting fusion cells. The first hybridomas may be those having reduced ability of active monoclonal antibody production.

The myeloma cells used in the present aspect are similar to those employed for the preparation of the above-described hybridomas. The cell fusion step for fusing hybridomas with myeloma cells and a step of purifying a monoclonal antibody from the resulting fusion cells can be performed as in the aspect of fusing the first hybridomas with the second hybridomas.

The hybridomas thus prepared can also produce an active monoclonal antibody instead of the monoclonal antibody produced using the first hybridomas having reduced production ability.

As a method of producing an antibody according to a further aspect of the present invention, third hybridomas or myeloma cells may be fused with the hybridomas obtained by fusing the first hybridomas with the second ones and from the resulting fusion cells, a monoclonal antibody may be purified.

Alternatively, third hybridomas or myeloma cells may be fused with the hybridomas obtained by fusing the first hybridomas with myeloma cells and from the resulting fusion cells, a monoclonal antibody may be purified.

EXAMPLES

The present invention will hereinafter be described specifically based on embodiments. The present invention is not limited to or by them. Those skilled in the art can change the present invention into various aspects without departing from the gist of the present invention. Such changes are also embraced in the scope of the present invention.

Example 1

A DH2 antibody (anti-GM3 antibody) was established as a mouse antibody (Dohi T et al., Cancer Res. 48, 5680-5685, 1988) and it was used in a number of papers. Due to reduction in antibody producing ability from hybridomas, however, it was not suited for use in experiments such as immune thin-layer chromatography reported first.

In various laboratories, re-cloning of hybridomas by the limiting dilution method was performed, but even if an antibody purified therefrom was used, reactivity in immune thin-layer chromatography was completely lost. A plurality of reasons for this loss of reactivity of the purified antibody can be considered, for example, incorporation of a plurality of antibody genes in the DH2 hybridomas or possibility of mixing of an antibody derived from mouse when mouse ascites is produced. This purified antibody is therefore not a DH2 antibody which was originally active but has lost its activity.

The hybridomas DH2 of the DH2 antibody that produced an active antibody in a markedly reduced amount and produced only an unintended antibody were fused with P3U1 cells, followed by re-cloning. Cell fusion was performed using a Sendai virus envelope GenomONE-CF (product of Ishihara Sangyo Kaisha). First, cells (DH2 and P3U1 cells) to be fused were prepared at 1:1. They were placed in a conical tube, mixed, and centrifuged. The supernatant was then removed. An ice-cooled fusion buffer was added and the mixture was converted into a uniform suspension by pipetting. An ice-cooled Sendai virus suspension was added to the resulting suspension and the mixture thus obtained was left at rest for 5 minutes on ice. After centrifugation at 1,000 rpm for 5 minutes, incubation was performed as was at 37 degrees for 15 minutes. The cells were seeded on a 96-well plate and from the next day, they were cultured after exchange for a HAT medium. The fusion method using a Sendai virus envelope was called RESET (Refusion by Sendai-virus Envelope Transformation) method.

After re-cloning, the hybridomas in the well in which an active antibody was produced were subjected to expansion culturing and retention of activity even after subculturing in a 10-cm dish was verified. The hybridomas were named DH2R and mass cultured using a serum-free medium. An antibody was purified using a ProteinG column. The amount of the antibody purified from the hybridomas DH2R increased by about three times the amount of the antibody purified from the hybridomas DH2.

The antigen-binding activity of the antibody thus obtained was analyzed using immune thin-layer chromatography.

Figure 11:
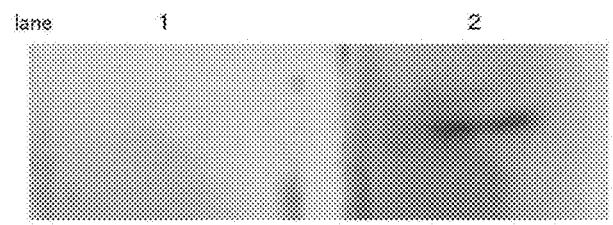
FIG. 11 shows the results of immune thin-layer chromatography, in which an antibody purified from the culture supernatant of hybridomas before re-activated is shown in lane 1 and an antibody purified from the culture supernatant of hybridomas reactivated by the method of the invention is shown in lane 2.

The purified GM3 (100 ng/lane) was developed using thin-layer chromatography and the purified antibody (lane 1) from the culture supernatant of the hybridomas DH2 was reacted with the purified antibody (lane 2) from the culture supernatant of the hybridomas DH2R established by RESET method, each 1 µg/mL. Then, the reaction product was reacted with anti-mouse IgG-HRP and ECL color development was detected using LAS3000. The results are shown in FIG. 11. The band of GM3 was detected only in lane 2.

Although the antibody production amount from the hybridomas DH2R was only about three times that from the hybridomas DH2, a specific reaction to GM3 was found only in the purified antibody derived from the hybridomas DH2R and no activity was found in the purified antibody derived from the hybridomas DH2 as a result of immune thin-layer chromatography. This suggests that the hybridomas DH2 have a plurality of antibody genes and due to continuation of subcloning, expression of an intended antibody gene of the DH2 antibody is suppressed or deleted and an inactive antibody gene is preferentially expressed, resulting in continuation of preferential production of an inactive antibody.

In fact, hybridomas producing a monoclonal antibody are known to have a plurality of antibody genes and cloning of an antibody gene from hybridomas results in cloning of a plurality of heavy-chain and light-chain genes from single hybridomas. This means that hybridomas contain, in addition to antibody genes derived from myeloma cells, antibody genes obtained by fusion of antibody producing cells due to fusion of a plurality of antibody producing cells. It is therefore presumed that when these unintended antibody genes become predominant, an intended antibody gene is deleted or its expression is suppressed.

Example 2

The present inventors established a YM-1 antibody (anti-podoplanin antibody) as a rat antibody (Kaneko M et al., J Biol Chem. 2004 Sep. 10; 279(37):38838-43). The YM-1 antibody has considerably high activity for human podoplanin and it has been used in a plurality of papers thereafter. Re-cloning of YM-1 hybridomas by limiting dilution method however failed to establish clones. The antibody amount in the culture supernatant is very small and a purified antibody cannot be acquired easily so that the supernatant is used in the papers. The YM-1 antibody is commercially available (Medical & Biological Laboratories (MBL)). Since a purified antibody cannot be acquired, it is sold as a concentrated antibody. Detailed study of the culture supernatant of the YM-1 antibody has revealed that it contains an inactive IgM class antibody and YM-1 hybridomas contain a plurality of antibody genes. Presence of this IgM class antibody gene is presumed to prevent stable production of an active anti-podoplanin antibody.

Culture supernatants can be used without a problem for various experiments (western blot, immunohistostaining, immunocytostaining, and the like), but a large amount of a purified antibody becomes necessary for use in animal experiments. Therefore, YM-1 hybridomas are fused with P3U1 cells and re-cloning performed. First, cells to be fused (YM-1 hybridomas and P3U1 cells) were prepared in a serum-free medium and they were mixed at 1:1 in the number of cells. While stirring the resulting cells vigorously in a warm bath of 37 degrees, 1 ml of a PEG1,500 solution (product of Sigma Aldrich) was added slowly to the cells. While stirring further, 5 ml of a serum-free medium (RPMI medium: product of Sigma Aldrich) was then added slowly to the cells. After centrifugation, the supernatant was removed and a RPMI medium containing 10% FBS (product of Life Technologies) was added. The cells were seeded on a 96-well plate and from the next day, they were cultured after replacement of the medium with a HAT-containing medium. The fusing method using PEG was named "REPEAT (Refusion by PEG attachment) method".

After re-cloning, the hybridomas in the well in which an active antibody was produced were subjected to expansion culture and retention of activity even after subculturing in a 10-cm dish was verified. The hybridomas were named YM-1R. They were mass cultured in a serum-free medium and an antibody was purified using a ProteinG column. A purified antibody was not obtained at all from the hybridomas YM-1 but a purified antibody was obtained from the hybridomas YM-1R. Experiment results using the YM-1 culture supernatant were therefore reproduced.

ABSTRACT

An object of the present invention is to provide a method of preparing an active antibody by re-activating hybridomas whose activity is not reproducible by single cell cloning or hybridomas which has stopped production of an active antibody in the subculturing procedure. The present invention provides a method of producing an antibody including a cell fusion step for fusing first hybridomas that have deteriorated ability of active monoclonal antibody production with second hybridomas or myeloma cells and a step of purifying a monoclonal antibody from the resulting fusion cells.

What is claimed is:

1. An anti-podoplanin antibody or antigen-binding fragment thereof, comprising one of the following three sets of CDRs:

(1)

a heavy chain CDR1: GYTFTSYTIH; (SEQ ID NO: 2)

a heavy chain CDR2: YINPGSGYTNYNEKFQD; (SEQ ID NO: 3)

a heavy chain CDR3: WDRGY; (SEQ ID NO: 4)

a light chain CDR1: RSSQTIVHSNGNTYLE; (SEQ ID NO: 5)

a light chain CDR2: KVSNRFS; (SEQ ID NO: 6) and a light chain CDR3: FQGSHVPYT, (SEQ ID NO: 7)

(2)

a heavy chain CDR1: GFTFSGFGMH; (SEQ ID NO: 14)

a heavy chain CDR2: YISSVSSRIYYADTVKG; (SEQ ID NO: 15)

a heavy chain CDR3: EQTGPAWFAY; (SEQ ID NO: 16)

a light chain CDR1: RSSRNIVQSTGNTYLE; (SEQ ID NO: 17)

```
                                                  (SEQ ID NO: 18)
a light chain CDR2: KVSNRFS;
and (SEQ ID NO: 19)
a light chain CDR3: FQGSHVPPWT,
and (3)
                                                  (SEQ ID NO: 71)
a heavy chain CDR1: GFSVTSYGIH;

(SEQ ID NO: 72)
a heavy chain CDR2: VIWTSGNTNYNSALMS;

(SEQ ID NO: 73)
a heavy chain CDR3: EDYYGYAMDY;

(SEQ ID NO: 74)
a light chain CDR1: RSSQSLLYSNGKTYLN;

(SEQ ID NO: 75)
a light chain CDR2: LVSKLDS;
and (SEQ ID NO: 76)
a light chain CDR3: VQGTHFPWT.
```

2. The anti-podoplanin antibody or antigen-binding fragment thereof according to claim 1, comprising:
a heavy chain having an amino acid sequence represented by SEQ ID NO: 26 or 63 and a light chain having an amino acid sequence represented by SEQ ID NO: 27.

3. The anti-podoplanin antibody or antigen-binding fragment thereof according to claim 1, comprising:
a heavy chain having an amino acid sequence represented by SEQ ID NO: 30 or 67 and a light chain having an amino acid sequence represented by SEQ ID NO: 31.

4. An anti-podoplanin antibody or antigen-binding fragment thereof, comprising:
a heavy chain having an amino acid sequence represented by SEQ ID NO: 78 and a light chain having an amino acid sequence represented by SEQ ID NO: 77.

5. The anti-podoplanin antibody or antigen-binding fragment thereof according to claim 1, wherein the anti-podoplanin antibody or antigen-binding fragment specifically binds podoplanin from a cancer cell, wherein the cancer is selected from the group consisting of malignant brain tumor, malignant mesothelioma, testicular tumor, ovarian cancer, and squamous cell cancer.

6. A pharmaceutical composition comprising the anti-podoplanin antibody or antigen-binding fragment thereof according to claim 1.

7. The pharmaceutical composition according to claim 1, and further comprising a substance having an anti-cancer activity bound to the anti-podoplanin antibody or antigen-binding fragment thereof.

8. A method for treating a subject of a cancer selected from the group consisting of malignant brain tumor, malignant mesothelioma, testicular tumor, ovarian cancer, and squamous cell cancer, which comprises administering to the subject the pharmaceutical composition according to claim 7.

9. The anti-podoplanin antibody or antigen-binding fragment thereof according to claim 1, wherein the anti-podoplanin antibody or antigen-binding fragment specifically binds podoplanin from a cancer cell, wherein the cancer is selected from the group consisting of malignant brain tumor, malignant mesothelioma, testicular tumor, ovarian cancer, and squamous cell cancer.

10. A pharmaceutical composition comprising the anti-podoplanin antibody or antigen-binding fragment thereof according to claim 1.

11. The pharmaceutical composition according to claim 10, and further comprising a substance having an anti-cancer activity bound to the anti-podoplanin antibody or antigen-binding fragment thereof.

12. A method for treating a subject of a cancer selected from the group consisting of malignant brain tumor, malignant mesothelioma, testicular tumor, ovarian cancer, and squamous cell cancer, which comprises administering to the subject the pharmaceutical composition according to claim 11.

* * * * *

SEQUENCE LISTING

<160> NUMBER OF SEQ ID NOS: 88

<210> SEQ ID NO 1
<211> LENGTH: 162
<212> TYPE: PRT
<213> ORGANISM: Homo sapiens

<400> SEQUENCE: 1

Met Trp Lys Val Ser Ala Leu Leu Phe Val Leu Gly Ser Ala Ser Leu
1               5                   10                  15

Trp Val Leu Ala Glu Gly Ala Ser Thr Gly Gln Pro Glu Asp Asp Thr
            20                  25                  30

Glu Thr Thr Gly Leu Glu Gly Gly Val Ala Met Pro Gly Ala Glu Asp
        35                  40                  45

Asp Val Val Thr Pro Gly Thr Ser Glu Asp Arg Tyr Lys Ser Gly Leu
    50                  55                  60

Thr Thr Leu Val Ala Thr Ser Val Asn Ser Val Thr Gly Ile Arg Ile
65                  70                  75                  80

Glu Asp Leu Pro Thr Ser Glu Ser Thr Val His Ala Gln Glu Gln Ser
                85                  90                  95

Pro Ser Ala Thr Ala Ser Asn Val Ala Thr Ser His Ser Thr Glu Lys
            100                 105                 110

Val Asp Gly Asp Thr Gln Thr Thr Val Glu Lys Asp Gly Leu Ser Thr
        115                 120                 125

Val Thr Leu Val Gly Ile Ile Val Gly Val Leu Leu Ala Ile Gly Phe
    130                 135                 140

Ile Gly Gly Ile Ile Val Val Met Arg Lys Met Ser Gly Arg Tyr
145                 150                 155                 160

Ser Pro

<210> SEQ ID NO 2
<211> LENGTH: 10
<212> TYPE: PRT
<213> ORGANISM: Artificial
<220> FEATURE:
<223> OTHER INFORMATION: Heavy chain CDR1 of LpMab-2.

<400> SEQUENCE: 2

Gly Tyr Thr Phe Thr Ser Tyr Thr Ile His
1               5                   10

<210> SEQ ID NO 3
<211> LENGTH: 17
<212> TYPE: PRT
<213> ORGANISM: Artificial
<220> FEATURE:
<223> OTHER INFORMATION: Heavy chain CDR2 of LpMab-2.

<400> SEQUENCE: 3

Tyr Ile Asn Pro Gly Ser Gly Tyr Thr Asn Tyr Asn Glu Lys Phe Gln
1               5                   10                  15

Asp

<210> SEQ ID NO 4
<211> LENGTH: 5
<212> TYPE: PRT
<213> ORGANISM: Artificial
<220> FEATURE:
<223> OTHER INFORMATION: Heavy chain CDR3 of LpMab-2.

<400> SEQUENCE: 4

Trp Asp Arg Gly Tyr
1               5

<210> SEQ ID NO 5
<211> LENGTH: 16
<212> TYPE: PRT
<213> ORGANISM: Artificial
<220> FEATURE:
<223> OTHER INFORMATION: Light chain CDR1 of LpMab-2.

<400> SEQUENCE: 5

Arg Ser Ser Gln Thr Ile Val His Ser Asn Gly Asn Thr Tyr Leu Glu
1               5                   10                  15

<210> SEQ ID NO 6
<211> LENGTH: 7
<212> TYPE: PRT
<213> ORGANISM: Artificial
<220> FEATURE:
<223> OTHER INFORMATION: Light chain CDR2 of LpMab-2.

<400> SEQUENCE: 6

Lys Val Ser Asn Arg Phe Ser
1               5

<210> SEQ ID NO 7
<211> LENGTH: 9
<212> TYPE: PRT
<213> ORGANISM: Artificial
<220> FEATURE:
<223> OTHER INFORMATION: Light chain CDR3 of LpMab-2.

<400> SEQUENCE: 7

Phe Gln Gly Ser His Val Pro Tyr Thr
1               5

<210> SEQ ID NO 8
<211> LENGTH: 10
<212> TYPE: PRT
<213> ORGANISM: Artificial
<220> FEATURE:
<223> OTHER INFORMATION: Heavy chain CDR1 of LpMab-3.

```
<400> SEQUENCE: 8

Gly Phe Thr Phe Thr Arg Tyr Ala Met Ser
1               5                   10

<210> SEQ ID NO 9
<211> LENGTH: 17
<212> TYPE: PRT
<213> ORGANISM: Artificial
<220> FEATURE:
<223> OTHER INFORMATION: Heavy chain CDR2 of LpMab-3.

<400> SEQUENCE: 9

Thr Ile Ser Asn Gly Gly Ser Tyr Thr Tyr Tyr Leu Asp Ser Val Lys
1               5                   10                  15

Gly

<210> SEQ ID NO 10
<211> LENGTH: 13
<212> TYPE: PRT
<213> ORGANISM: Artificial
<220> FEATURE:
<223> OTHER INFORMATION: Heavy chain CDR3 of LpMab-3.

<400> SEQUENCE: 10

Arg Glu Gly Gly Gln Ala Gly Pro Ala Trp Phe Val Tyr
1               5                   10

<210> SEQ ID NO 11
<211> LENGTH: 17
<212> TYPE: PRT
<213> ORGANISM: Artificial
<220> FEATURE:
<223> OTHER INFORMATION: Light chain CDR1 of LpMab-3.

<400> SEQUENCE: 11

Lys Ser Ser Gln Ser Leu Leu Asn Ser Ser Asn Gln Lys Asn Tyr Leu
1               5                   10                  15

Ala

<210> SEQ ID NO 12
<211> LENGTH: 7
<212> TYPE: PRT
<213> ORGANISM: Artificial
<220> FEATURE:
<223> OTHER INFORMATION: Light chain CDR2 of LpMab-3.

<400> SEQUENCE: 12

Phe Ala Ser Thr Arg Glu Ser
1               5

<210> SEQ ID NO 13
<211> LENGTH: 9
<212> TYPE: PRT
<213> ORGANISM: Artificial
<220> FEATURE:
<223> OTHER INFORMATION: Light chain CDR3 of LpMab-3.

<400> SEQUENCE: 13

Gln Gln Tyr Tyr Ser Thr Pro Pro Thr
1               5

<210> SEQ ID NO 14
<211> LENGTH: 10
<212> TYPE: PRT
<213> ORGANISM: Artificial
```

<220> FEATURE:
<223> OTHER INFORMATION: Heavy chain CDR1 of LpMab-7.

<400> SEQUENCE: 14

Gly Phe Thr Phe Ser Gly Phe Gly Met His
1               5                   10

<210> SEQ ID NO 15
<211> LENGTH: 17
<212> TYPE: PRT
<213> ORGANISM: Artificial
<220> FEATURE:
<223> OTHER INFORMATION: Heavy chain CDR2 of LpMab-7.

<400> SEQUENCE: 15

Tyr Ile Ser Ser Val Ser Ser Arg Ile Tyr Tyr Ala Asp Thr Val Lys
1               5                   10                  15

Gly

<210> SEQ ID NO 16
<211> LENGTH: 10
<212> TYPE: PRT
<213> ORGANISM: Artificial
<220> FEATURE:
<223> OTHER INFORMATION: Heavy chain CDR3 of LpMab-7.

<400> SEQUENCE: 16

Glu Gln Thr Gly Pro Ala Trp Phe Ala Tyr
1               5                   10

<210> SEQ ID NO 17
<211> LENGTH: 16
<212> TYPE: PRT
<213> ORGANISM: Artificial
<220> FEATURE:
<223> OTHER INFORMATION: Light chain CDR1 of LpMab-7.

<400> SEQUENCE: 17

Arg Ser Ser Arg Asn Ile Val Gln Ser Thr Gly Asn Thr Tyr Leu Glu
1               5                   10                  15

<210> SEQ ID NO 18
<211> LENGTH: 7
<212> TYPE: PRT
<213> ORGANISM: Artificial
<220> FEATURE:
<223> OTHER INFORMATION: Light chain CDR2 of LpMab-7.

<400> SEQUENCE: 18

Lys Val Ser Asn Arg Phe Ser
1               5

<210> SEQ ID NO 19
<211> LENGTH: 10
<212> TYPE: PRT
<213> ORGANISM: Artificial
<220> FEATURE:
<223> OTHER INFORMATION: Light chain CDR3 of LpMab-7.

<400> SEQUENCE: 19

Phe Gln Gly Ser His Val Pro Pro Trp Thr
1               5                   10

<210> SEQ ID NO 20
<211> LENGTH: 10
<212> TYPE: PRT

<213> ORGANISM: Artificial
<220> FEATURE:
<223> OTHER INFORMATION: Heavy chain CDR1 of LpMab-9.

<400> SEQUENCE: 20

Gly Tyr Thr Phe Thr Lys Ser Gly Met Gln
1               5                   10

<210> SEQ ID NO 21
<211> LENGTH: 17
<212> TYPE: PRT
<213> ORGANISM: Artificial
<220> FEATURE:
<223> OTHER INFORMATION: Heavy chain CDR2 of LpMab-9.

<400> SEQUENCE: 21

Trp Ile Asn Thr His Ser Gly Val Pro Lys Tyr Ala Glu Asp Phe Lys
1               5                   10                  15

Gly

<210> SEQ ID NO 22
<211> LENGTH: 9
<212> TYPE: PRT
<213> ORGANISM: Artificial
<220> FEATURE:
<223> OTHER INFORMATION: Heavy chain CDR3 of LpMab-9.

<400> SEQUENCE: 22

Trp Gly Gly Asp Gly Ala Met Asp Tyr
1               5

<210> SEQ ID NO 23
<211> LENGTH: 17
<212> TYPE: PRT
<213> ORGANISM: Artificial
<220> FEATURE:
<223> OTHER INFORMATION: Light chain CDR1 of LpMab-9.

<400> SEQUENCE: 23

Lys Ser Ser Gln Ser Leu Leu Lys Ser Ser Gln Lys Asn Tyr Leu
1               5                   10                  15

Ala

<210> SEQ ID NO 24
<211> LENGTH: 7
<212> TYPE: PRT
<213> ORGANISM: Artificial
<220> FEATURE:
<223> OTHER INFORMATION: Light chain CDR2 of LpMab-9.

<400> SEQUENCE: 24

Phe Ala Ser Thr Arg Glu Ser
1               5

<210> SEQ ID NO 25
<211> LENGTH: 9
<212> TYPE: PRT
<213> ORGANISM: Artificial
<220> FEATURE:
<223> OTHER INFORMATION: Light chain CDR3 of LpMab-9.

<400> SEQUENCE: 25

Gln Gln His Tyr Ser Ala Pro Leu Ser
1               5

-continued

```
<210> SEQ ID NO 26
<211> LENGTH: 457
<212> TYPE: PRT
<213> ORGANISM: Artificial
<220> FEATURE:
<223> OTHER INFORMATION: Heavy chain of LpMab-2.

<400> SEQUENCE: 26
```

| | | | | | | | | | | | | | | | |
|---|---|---|---|---|---|---|---|---|---|---|---|---|---|---|---|
| Met | Glu | Arg | His | Trp | Ile | Phe | Leu | Leu | Leu | Ser | Val | Thr | Ala | Gly | |
| 1 | | | | 5 | | | | | 10 | | | | | 15 | |
| Val | His | Ser | Gln | Val | Gln | Val | Gln | Ser | Gly | Ala | Glu | Leu | Ala | Arg | |
| | | | 20 | | | | | 25 | | | | | 30 | | |
| Pro | Gly | Ala | Ser | Val | Lys | Met | Ser | Cys | Lys | Ala | Ser | Gly | Tyr | Thr | Phe |
| | | 35 | | | | | 40 | | | | | 45 | | | |
| Thr | Ser | Tyr | Thr | Ile | His | Trp | Val | Lys | Gln | Arg | Pro | Arg | Gln | Gly | Leu |
| | 50 | | | | | 55 | | | | | 60 | | | | |
| Glu | Trp | Ile | Gly | Tyr | Ile | Asn | Pro | Gly | Ser | Gly | Tyr | Thr | Asn | Tyr | Asn |
| 65 | | | | | 70 | | | | | 75 | | | | | 80 |
| Glu | Lys | Phe | Gln | Asp | Lys | Ala | Thr | Leu | Thr | Ala | Asp | Lys | Ser | Ser | Thr |
| | | | | 85 | | | | | 90 | | | | | 95 | |
| Thr | Ala | Tyr | Met | Gln | Leu | Ser | Ser | Leu | Thr | Ser | Glu | Asp | Ser | Ala | Val |
| | | | 100 | | | | | 105 | | | | | 110 | | |
| Tyr | Tyr | Cys | Ala | Arg | Trp | Asp | Arg | Gly | Tyr | Trp | Gly | Gln | Gly | Thr | Thr |
| | | 115 | | | | | 120 | | | | | 125 | | | |
| Leu | Thr | Val | Ser | Ser | Ala | Lys | Thr | Thr | Pro | Pro | Ser | Val | Tyr | Pro | Leu |
| | 130 | | | | | 135 | | | | | 140 | | | | |
| Ala | Pro | Gly | Ser | Ala | Ala | Gln | Thr | Asn | Ser | Met | Val | Thr | Leu | Gly | Cys |
| 145 | | | | | 150 | | | | | 155 | | | | | 160 |
| Leu | Val | Lys | Gly | Tyr | Phe | Pro | Glu | Pro | Val | Thr | Val | Thr | Trp | Asn | Ser |
| | | | | 165 | | | | | 170 | | | | | 175 | |
| Gly | Ser | Leu | Ser | Ser | Gly | Val | His | Thr | Phe | Pro | Ala | Val | Leu | Gln | Ser |
| | | | 180 | | | | | 185 | | | | | 190 | | |
| Asp | Leu | Tyr | Thr | Leu | Ser | Ser | Ser | Val | Thr | Val | Pro | Ser | Ser | Thr | Trp |
| | | 195 | | | | | 200 | | | | | 205 | | | |
| Pro | Ser | Glu | Thr | Val | Thr | Cys | Asn | Val | Ala | His | Pro | Ala | Ser | Ser | Thr |
| | 210 | | | | | 215 | | | | | 220 | | | | |
| Lys | Val | Asp | Lys | Lys | Ile | Val | Pro | Arg | Asp | Cys | Gly | Cys | Lys | Pro | Cys |
| 225 | | | | | 230 | | | | | 235 | | | | | 240 |
| Ile | Cys | Thr | Val | Pro | Glu | Val | Ser | Ser | Val | Phe | Ile | Phe | Pro | Pro | Lys |
| | | | | 245 | | | | | 250 | | | | | 255 | |
| Pro | Lys | Asp | Val | Leu | Thr | Ile | Thr | Leu | Thr | Pro | Lys | Val | Thr | Cys | Val |
| | | | 260 | | | | | 265 | | | | | 270 | | |
| Val | Val | Asp | Ile | Ser | Lys | Asp | Asp | Pro | Glu | Val | Gln | Phe | Ser | Trp | Phe |
| | | 275 | | | | | 280 | | | | | 285 | | | |
| Val | Asp | Asp | Val | Glu | Val | His | Thr | Ala | Gln | Thr | Gln | Pro | Arg | Glu | Glu |
| | 290 | | | | | 295 | | | | | 300 | | | | |
| Gln | Phe | Asn | Ser | Thr | Phe | Arg | Ser | Val | Ser | Glu | Leu | Pro | Ile | Met | His |
| 305 | | | | | 310 | | | | | 315 | | | | | 320 |
| Gln | Asp | Trp | Leu | Asn | Gly | Lys | Glu | Phe | Lys | Cys | Arg | Val | Asn | Ser | Ala |
| | | | | 325 | | | | | 330 | | | | | 335 | |
| Ala | Phe | Pro | Ala | Pro | Ile | Glu | Lys | Thr | Ile | Ser | Lys | Thr | Lys | Gly | Arg |
| | | | 340 | | | | | 345 | | | | | 350 | | |
| Pro | Lys | Ala | Pro | Gln | Val | Tyr | Thr | Ile | Pro | Pro | Pro | Lys | Glu | Gln | Met |
| | | 355 | | | | | 360 | | | | | 365 | | | |
| Ala | Lys | Asp | Lys | Val | Ser | Leu | Thr | Cys | Met | Ile | Thr | Asp | Phe | Phe | Pro |

```
                370                 375                 380
Glu Asp Ile Thr Val Glu Trp Gln Trp Asn Gly Gln Pro Ala Glu Asn
385                 390                 395                 400

Tyr Lys Asn Thr Gln Pro Ile Met Asp Thr Asp Gly Ser Tyr Phe Val
                405                 410                 415

Tyr Ser Lys Leu Asn Val Gln Lys Ser Asn Trp Glu Ala Gly Asn Thr
                420                 425                 430

Phe Thr Cys Ser Val Leu His Glu Gly Leu His Asn His His Thr Glu
                435                 440                 445

Lys Ser Leu Ser His Ser Pro Gly Lys
                450                 455

<210> SEQ ID NO 27
<211> LENGTH: 238
<212> TYPE: PRT
<213> ORGANISM: Artificial
<220> FEATURE:
<223> OTHER INFORMATION: Light chain of LpMab-2.

<400> SEQUENCE: 27

Met Lys Leu Pro Val Arg Leu Leu Val Leu Met Phe Trp Ile Pro Ala
1               5                   10                  15

Ser Ser Thr Asp Val Leu Met Thr Gln Thr Pro Leu Ser Leu Pro Ile
                20                  25                  30

Ser Leu Gly Asp Gln Ala Ser Ile Ser Cys Arg Ser Ser Gln Thr Ile
                35                  40                  45

Val His Ser Asn Gly Asn Thr Tyr Leu Glu Trp Tyr Leu Gln Lys Pro
                50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Leu Thr
                85                  90                  95

Leu Lys Ile Ser Arg Val Glu Ala Glu Asp Leu Gly Val Tyr Tyr Cys
                100                 105                 110

Phe Gln Gly Ser His Val Pro Tyr Thr Phe Gly Gly Gly Thr Lys Leu
                115                 120                 125

Glu Ile Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
                180                 185                 190

Lys Asp Ser Thr Tyr Ser Met Ser Ser Thr Leu Thr Leu Thr Arg Asp
                195                 200                 205

Glu Tyr Glu Arg His Asn Ser Tyr Thr Cys Glu Ala Thr His Lys Thr
                210                 215                 220

Ser Thr Ser Pro Ile Val Lys Ser Phe Asn Arg Asn Glu Cys
225                 230                 235

<210> SEQ ID NO 28
<211> LENGTH: 465
<212> TYPE: PRT
<213> ORGANISM: Artificial
<220> FEATURE:
<223> OTHER INFORMATION: Heavy chain of LpMab-3.
```

<400> SEQUENCE: 28

Met Asn Phe Val Leu Ser Leu Ile Phe Leu Ala Leu Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Thr Arg Tyr Ala Met Ser Trp Val Arg Gln Thr Pro Glu Lys Arg Leu
    50                  55                  60

Glu Trp Val Ala Thr Ile Ser Asn Gly Gly Ser Tyr Thr Tyr Tyr Leu
65                  70                  75                  80

Asp Ser Val Lys Gly Arg Phe Thr Leu Ser Arg Asp Asn Ala Lys Asn
                85                  90                  95

Thr Leu Tyr Leu Gln Met Ser Ser Leu Arg Ser Glu Asp Thr Ala Met
            100                 105                 110

Tyr Tyr Cys Ala Arg Arg Glu Gly Gln Ala Gly Pro Ala Trp Phe
        115                 120                 125

Val Tyr Trp Gly Gln Gly Thr Leu Val Thr Val Ser Ala Ala Lys Thr
130                 135                 140

Thr Pro Pro Ser Val Tyr Pro Leu Ala Pro Gly Ser Ala Ala Gln Thr
145                 150                 155                 160

Asn Ser Met Val Thr Leu Gly Cys Leu Val Lys Gly Tyr Phe Pro Glu
                165                 170                 175

Pro Val Thr Val Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205

Val Thr Val Pro Ser Ser Thr Trp Pro Ser Glu Thr Val Thr Cys Asn
210                 215                 220

Val Ala His Pro Ala Ser Ser Thr Lys Val Asp Lys Lys Ile Val Pro
225                 230                 235                 240

Arg Asp Cys Gly Cys Lys Pro Cys Ile Cys Thr Val Pro Glu Val Ser
                245                 250                 255

Ser Val Phe Ile Phe Pro Pro Lys Pro Lys Asp Val Leu Thr Ile Thr
            260                 265                 270

Leu Thr Pro Lys Val Thr Cys Val Val Val Asp Ile Ser Lys Asp Asp
        275                 280                 285

Pro Glu Val Gln Phe Ser Trp Phe Val Asp Asp Val Glu Val His Thr
290                 295                 300

Ala Gln Thr Gln Pro Arg Glu Glu Gln Phe Asn Ser Thr Phe Arg Ser
305                 310                 315                 320

Val Ser Glu Leu Pro Ile Met His Gln Asp Trp Leu Asn Gly Lys Glu
                325                 330                 335

Phe Lys Cys Arg Val Asn Ser Ala Ala Phe Pro Ala Pro Ile Glu Lys
            340                 345                 350

Thr Ile Ser Lys Thr Lys Gly Arg Pro Lys Ala Pro Gln Val Tyr Thr
        355                 360                 365

Ile Pro Pro Pro Lys Glu Gln Met Ala Lys Asp Lys Val Ser Leu Thr
370                 375                 380

Cys Met Ile Thr Asp Phe Phe Pro Glu Asp Ile Thr Val Glu Trp Gln
385                 390                 395                 400

Trp Asn Gly Gln Pro Ala Glu Asn Tyr Lys Asn Thr Gln Pro Ile Met

```
                    405                 410                 415
Asp Thr Asp Gly Ser Tyr Phe Val Tyr Ser Lys Leu Asn Val Gln Lys
                420                 425                 430

Ser Asn Trp Glu Ala Gly Asn Thr Phe Thr Cys Ser Val Leu His Glu
            435                 440                 445

Gly Leu His Asn His His Thr Glu Lys Ser Leu Ser His Ser Pro Gly
        450                 455                 460

Lys
465

<210> SEQ ID NO 29
<211> LENGTH: 240
<212> TYPE: PRT
<213> ORGANISM: Artificial
<220> FEATURE:
<223> OTHER INFORMATION: Light chain of LpMab-3.

<400> SEQUENCE: 29

Met Glu Ser Gln Thr Gln Val Leu Met Phe Leu Leu Leu Trp Val Ser
1               5                   10                  15

Gly Ala Cys Ala Asp Ile Val Met Thr Gln Ser Pro Ser Ser Leu Ala
                20                  25                  30

Met Ser Val Gly Gln Lys Val Thr Met Asn Cys Lys Ser Ser Gln Ser
            35                  40                  45

Leu Leu Asn Ser Ser Asn Gln Lys Asn Tyr Leu Ala Trp Tyr Gln Gln
        50                  55                  60

Lys Pro Gly Gln Ser Pro Lys Leu Leu Val Tyr Phe Ala Ser Thr Arg
65                  70                  75                  80

Glu Ser Gly Val Pro Asp Arg Phe Ile Gly Ser Gly Ser Gly Thr Asp
                85                  90                  95

Phe Thr Leu Thr Ile Ser Ser Ala Gln Ala Glu Asp Leu Ala Asp Tyr
                100                 105                 110

Phe Cys Gln Gln Tyr Tyr Ser Thr Pro Pro Thr Phe Gly Ala Gly Thr
            115                 120                 125

Lys Leu Glu Leu Lys Arg Ala Asp Ala Ala Pro Thr Val Ser Ile Phe
        130                 135                 140

Pro Pro Ser Ser Glu Gln Leu Thr Ser Gly Gly Ala Ser Val Val Cys
145                 150                 155                 160

Phe Leu Asn Asn Phe Tyr Pro Lys Asp Ile Asn Val Lys Trp Lys Ile
                165                 170                 175

Asp Gly Ser Glu Arg Gln Asn Gly Val Leu Asn Ser Trp Thr Asp Gln
                180                 185                 190

Asp Ser Lys Asp Ser Thr Tyr Ser Met Ser Ser Thr Leu Thr Leu Thr
            195                 200                 205

Lys Asp Glu Tyr Glu Arg His Asn Ser Tyr Thr Cys Glu Ala Thr His
        210                 215                 220

Lys Thr Ser Thr Ser Pro Ile Val Lys Ser Phe Asn Arg Asn Glu Cys
225                 230                 235                 240

<210> SEQ ID NO 30
<211> LENGTH: 462
<212> TYPE: PRT
<213> ORGANISM: Artificial
<220> FEATURE:
<223> OTHER INFORMATION: Heavy chain of LpMab-7.

<400> SEQUENCE: 30
```

```
Met Asp Ser Arg Leu Asn Leu Val Phe Leu Val Ile Leu Lys Gly
1               5                   10                  15

Val Gln Cys Asp Val Gln Leu Val Glu Ser Gly Gly Gly Leu Val Gln
            20                  25                  30

Pro Gly Gly Ser Arg Lys Leu Ser Cys Ala Ala Ser Gly Phe Thr Phe
                35                  40                  45

Ser Gly Phe Gly Met His Trp Val Arg Gln Ala Pro Glu Lys Gly Leu
    50                  55                  60

Glu Trp Val Ala Tyr Ile Ser Ser Val Ser Arg Ile Tyr Tyr Ala
65                      70                  75                  80

Asp Thr Val Lys Gly Arg Phe Thr Ile Ser Arg Asp Asn Pro Lys Asn
                85                  90                  95

Thr Leu Phe Leu Gln Met Thr Ser Leu Arg Ser Glu Asp Thr Ala Met
                100                 105                 110

Tyr Tyr Cys Ala Arg Glu Gln Thr Gly Pro Ala Trp Phe Ala Tyr Trp
            115                 120                 125

Gly Gln Gly Thr Leu Val Thr Val Ser Ala Ala Lys Thr Thr Pro Pro
        130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
                180                 185                 190

Ala Val Leu Gln Ser Asp Leu Tyr Thr Leu Ser Ser Ser Val Thr Val
            195                 200                 205

Pro Ser Ser Thr Trp Pro Ser Glu Thr Val Thr Cys Asn Val Ala His
        210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
                260                 265                 270

Lys Val Thr Cys Val Val Val Asp Ile Ser Lys Asp Asp Pro Glu Val
            275                 280                 285

Gln Phe Ser Trp Phe Val Asp Asp Val Glu Val His Thr Ala Gln Thr
        290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Ala Ala Phe Pro Ala Pro Ile Glu Lys Thr Ile Ser
                340                 345                 350

Lys Thr Lys Gly Arg Pro Lys Ala Pro Gln Val Tyr Thr Ile Pro Pro
            355                 360                 365

Pro Lys Glu Gln Met Ala Lys Asp Lys Val Ser Leu Thr Cys Met Ile
        370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                405                 410                 415

Gly Ser Tyr Phe Val Tyr Ser Lys Leu Asn Val Gln Lys Ser Asn Trp
```

Glu Ala Gly Asn Thr Phe Thr Cys Ser Val Leu His Glu Gly Leu His
                435                 440                 445

Asn His His Thr Glu Lys Ser Leu Ser His Ser Pro Gly Lys
        450                 455                 460

<210> SEQ ID NO 31
<211> LENGTH: 239
<212> TYPE: PRT
<213> ORGANISM: Artificial
<220> FEATURE:
<223> OTHER INFORMATION: Light chain of LpMab-7.

<400> SEQUENCE: 31

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Arg Asn Ile
        35                  40                  45

Val Gln Ser Thr Gly Asn Thr Tyr Leu Glu Trp Tyr Leu Gln Lys Pro
    50                  55                  60

Gly Gln Ser Pro Lys Leu Leu Ile Phe Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Pro Trp Thr Phe Gly Gly Gly Thr Lys
        115                 120                 125

Leu Glu Ile Lys Arg Ala Asp Ala Ala Pro Thr Val Ser Ile Phe Pro
130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

<210> SEQ ID NO 32
<211> LENGTH: 461
<212> TYPE: PRT
<213> ORGANISM: Artificial
<220> FEATURE:
<223> OTHER INFORMATION: Heavy chain of LpMab-9.

<400> SEQUENCE: 32

Met Glu Cys Leu Trp Asn Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

```
Pro Gly Glu Thr Val Arg Ile Ser Cys Lys Ala Ser Gly Tyr Thr Phe
        35                  40                  45
Thr Lys Ser Gly Met Gln Trp Val Gln Lys Met Ser Gly Lys Gly Leu
 50                  55                  60
Lys Trp Ile Gly Trp Ile Asn Thr His Ser Gly Val Pro Lys Tyr Ala
 65                  70                  75                  80
Glu Asp Phe Lys Gly Arg Phe Ala Phe Ser Leu Glu Thr Ser Ala Ser
                 85                  90                  95
Ser Ala Tyr Leu Gln Ile Ser Asn Leu Lys Asn Glu Asp Thr Ala Thr
            100                 105                 110
Tyr Phe Cys Ala Arg Trp Gly Asp Gly Ala Met Asp Tyr Trp Gly
            115                 120                 125
Gln Gly Thr Ser Val Thr Val Ser Ser Ala Lys Thr Thr Pro Pro Ser
130                 135                 140
Val Tyr Pro Leu Ala Pro Gly Ser Ala Ala Gln Thr Asn Ser Met Val
145                 150                 155                 160
Thr Leu Gly Cys Leu Val Lys Gly Tyr Phe Pro Glu Pro Val Thr Val
                165                 170                 175
Thr Trp Asn Ser Gly Ser Leu Ser Ser Gly Val His Thr Phe Pro Ala
            180                 185                 190
Val Leu Gln Ser Asp Leu Tyr Thr Leu Ser Ser Ser Val Thr Val Pro
        195                 200                 205
Ser Ser Thr Trp Pro Ser Glu Thr Val Thr Cys Asn Val Ala His Pro
    210                 215                 220
Ala Ser Ser Thr Lys Val Asp Lys Lys Ile Val Pro Arg Asp Cys Gly
225                 230                 235                 240
Cys Lys Pro Cys Ile Cys Thr Val Pro Glu Val Ser Ser Val Phe Ile
                245                 250                 255
Phe Pro Pro Lys Pro Lys Asp Val Leu Thr Ile Thr Leu Thr Pro Lys
            260                 265                 270
Val Thr Cys Val Val Val Asp Ile Ser Lys Asp Asp Pro Glu Val Gln
        275                 280                 285
Phe Ser Trp Phe Val Asp Asp Val Glu Val His Thr Ala Gln Thr Gln
    290                 295                 300
Pro Arg Glu Glu Gln Phe Asn Ser Thr Phe Arg Ser Val Ser Glu Leu
305                 310                 315                 320
Pro Ile Met His Gln Asp Trp Leu Asn Gly Lys Glu Phe Lys Cys Arg
                325                 330                 335
Val Asn Ser Ala Ala Phe Pro Ala Pro Ile Glu Lys Thr Ile Ser Lys
            340                 345                 350
Thr Lys Gly Arg Pro Lys Ala Pro Gln Val Tyr Thr Ile Pro Pro Pro
        355                 360                 365
Lys Glu Gln Met Ala Lys Asp Lys Val Ser Leu Thr Cys Met Ile Thr
370                 375                 380
Asp Phe Phe Pro Glu Asp Ile Thr Val Glu Trp Gln Trp Asn Gly Gln
385                 390                 395                 400
Pro Ala Glu Asn Tyr Lys Asn Thr Gln Pro Ile Met Asp Thr Asp Gly
                405                 410                 415
Ser Tyr Phe Val Tyr Ser Lys Leu Asn Val Gln Lys Ser Asn Trp Glu
            420                 425                 430
Thr Gly Asn Thr Phe Thr Cys Ser Val Leu His Glu Gly Leu His Asn
        435                 440                 445
His His Thr Glu Lys Ser Leu Ser His Ser Pro Gly Lys
```

<210> SEQ ID NO 33
<211> LENGTH: 240
<212> TYPE: PRT
<213> ORGANISM: Artificial
<220> FEATURE:
<223> OTHER INFORMATION: Light chain of LpMab-9.

<400> SEQUENCE: 33

Met Glu Ser Gln Thr Gln Val Leu Met Phe Leu Leu Leu Trp Val Ser
1               5                   10                  15
Gly Ala Cys Ala Asp Ile Val Met Thr Gln Ser Pro Ser Ser Leu Thr
            20                  25                  30
Met Ser Val Gly Gln Arg Val Thr Met Ser Cys Lys Ser Ser Gln Ser
        35                  40                  45
Leu Leu Lys Ser Ser Ser Gln Lys Asn Tyr Leu Ala Trp Tyr Gln Gln
    50                  55                  60
Lys Pro Gly Gln Ser Pro Lys Leu Leu Val Tyr Phe Ala Ser Thr Arg
65                  70                  75                  80
Glu Ser Gly Val Pro Asp Arg Phe Ile Gly Ser Gly Ser Gly Thr Asp
                85                  90                  95
Phe Thr Leu Thr Ile Ser Ser Val Gln Ala Glu Asp Leu Ala Asp Tyr
            100                 105                 110
Phe Cys Gln Gln His Tyr Ser Ala Pro Leu Ser Phe Gly Ala Gly Thr
        115                 120                 125
Lys Leu Glu Leu Arg Arg Ala Asp Ala Ala Pro Thr Val Ser Ile Phe
    130                 135                 140
Pro Pro Ser Ser Glu Gln Leu Thr Ser Gly Gly Ala Ser Val Val Cys
145                 150                 155                 160
Phe Leu Asn Asn Phe Tyr Pro Lys Asp Ile Asn Val Lys Trp Lys Ile
                165                 170                 175
Asp Gly Ser Glu Arg Gln Asn Gly Val Leu Asn Ser Trp Thr Asp Gln
            180                 185                 190
Asp Ser Lys Asp Ser Thr Tyr Ser Met Ser Ser Thr Leu Thr Leu Thr
        195                 200                 205
Lys Asp Glu Tyr Glu Arg His Asn Ser Tyr Thr Cys Glu Ala Thr His
    210                 215                 220
Lys Thr Ser Thr Ser Pro Ile Val Lys Ser Phe Asn Arg Asn Glu Cys
225                 230                 235                 240

<210> SEQ ID NO 34
<211> LENGTH: 1371
<212> TYPE: DNA
<213> ORGANISM: Artificial
<220> FEATURE:
<223> OTHER INFORMATION: Heavy chain of LpMab-2.

<400> SEQUENCE: 34
atggaaaggc actggatctt tctactcctg ttgtcagtaa ctgcaggtgt ccactcccag      60
gtccaggtgc agcagtctgg ggctgaactg gcaagacctg gggcctcagt gaagatgtcc     120
tgcaaggctt ctggctacac ctttactagc tacacgatac actgggtaaa acagaggcct     180
agacagggtc tggaatggat tggatacatt aatcctggca gtggttatac taattacaat     240
gagaagttcc aggacaaggc acattgact gcagacaaat cctccaccac agcctacatg      300
caactgagca gcctgacatc tgaggactct gcagtctatt actgtgcaag atgggatagg     360

| | |
|---|---|
| ggctactggg gccaaggcac cactctcaca gtctcctcag ccaaaacgac acccccatct | 420 |
| gtctatccac tggcccctgg atctgctgcc caaactaact ccatggtgac cctgggatgc | 480 |
| ctggtcaagg gctatttccc tgagccagtg acagtgacct ggaactctgg atccctgtcc | 540 |
| agcggtgtgc acaccttccc agctgtcctg cagtctgacc tctacactct gagcagctca | 600 |
| gtgactgtcc cctccagcac ctggcccagc gagaccgtca cctgcaacgt tgcccacccg | 660 |
| gccagcagca ccaaggtgga caagaaaatt gtgcccaggg attgtggttg taagccttgc | 720 |
| atatgtacag tcccagaagt atcatctgtc ttcatcttcc ccccaaagcc caaggatgtg | 780 |
| ctcaccatta tctgactcc taaggtcacg tgtgttgtgg tagacatcag caaggatgat | 840 |
| cccgaggtcc agttcagctg gtttgtagat gatgtggagg tgcacacagc tcagacgcaa | 900 |
| ccccgggagg agcagttcaa cagcactttc cgctcagtca gtgaacttcc catcatgcac | 960 |
| caggactggc tcaatggcaa ggagttcaaa tgcagggtca cagtgcagc tttcctgcc | 1020 |
| cccatcgaga aaccatctc caaaccaaa ggcagaccga aggctccaca ggtgtacacc | 1080 |
| attccacctc ccaaggagca gatggccaag ataaagtca gtctgacctg catgataaca | 1140 |
| gacttcttcc ctgaagacat tactgtggag tggcagtgga tgggcagcc agcggagaac | 1200 |
| tacaagaaca ctcagcccat catggacaca gatggctctt acttcgtcta cagcaagctc | 1260 |
| aatgtgcaga gagcaactg ggaggcagga aatactttca cctgctctgt gttacatgag | 1320 |
| ggcctgcaca accaccatac tgagaagagc ctctcccact tcctggtaa a | 1371 |

<210> SEQ ID NO 35
<211> LENGTH: 714
<212> TYPE: DNA
<213> ORGANISM: Artificial
<220> FEATURE:
<223> OTHER INFORMATION: Light chain of LpMab-2.

<400> SEQUENCE: 35

| | |
|---|---|
| atgaagttgc ctgttaggct gttggtgctg atgttctgga ttcctgcttc cagcactgat | 60 |
| gttttgatga cccaaactcc actctccctg cctatcagtc ttggagatca agcctccatc | 120 |
| tcttgcagat ctagtcagac cattgtacat agtaatggaa acacctattt agaatggtac | 180 |
| ctgcagaaac caggccagtc tccaaagctc ctgatctaca agtttccaa ccgattttct | 240 |
| ggggtcccag acaggttcag tggcagtgga tcagggacag atctcacact caagatcagc | 300 |
| agagtggagg ctgaggatct gggagtttat tactgctttc aaggttcaca tgttccgtac | 360 |
| acgttcggag gggggaccaa gctggaaata aaacgggctg atgctgcacc aactgtatcc | 420 |
| atcttcccac catccagtga gcagttaaca tctggaggtg cctcagtcgt gtgcttcttg | 480 |
| aacaacttct accccaaaga catcaatgtc aagtggaaga ttgatggcag tgaacgacaa | 540 |
| aatggcgtcc tgaacagttg gactgatcag gacagcaaag acagcaccta cagcatgagc | 600 |
| agcaccctca cgttgaccag ggacgagtat gaacgacata acagctatac ctgtgaggcc | 660 |
| actcacaaga catcaacttc acccattgtc aagagcttca caggaatga gtgt | 714 |

<210> SEQ ID NO 36
<211> LENGTH: 1395
<212> TYPE: DNA
<213> ORGANISM: Artificial
<220> FEATURE:
<223> OTHER INFORMATION: Heavy chain of LpMab-3.

<400> SEQUENCE: 36

| | |
|---|---|
| atgaactttg tgctcagctt gattttcctt gccctcattt taaaggtgt ccagtgtgaa | 60 |

```
gtgcagctgg tggagtctgg gggaggctta gtgaagcctg gagggtccct gaaactctcc      120
tgtgcagcct ctggattcac tttcactaga tatgccatgt cttgggttcg tcagactccg      180
gagaagaggc tggagtgggt cgcaaccatt agtaatggtg gtagttatac ctactattta      240
gacagtgtga agggtcgatt caccttatcc agagacaatg ccaagaacac cctgtacctg      300
caaatgagca gtctgaggtc tgaggacacg gccatgtatt actgtgcaag acgggagggc      360
ggacaggccg ggcccgcctg gtttgtttac tggggccaag ggactctggt cactgtctct      420
gcagccaaaa cgacacccc atctgtctat ccactggccc ctggatctgc tgcccaaact       480
aactccatgg tgaccctggg atgcctggtc aagggctatt ccctgagcc agtgacagtg       540 acctggaact ctggatccct gtccagcggt gtgcacacct cccagctgt cctgcagtct       600 gacctctaca ctctgagcag ctcagtgact gtccctcca gcacctggcc cagcgagacc       660
gtcacctgca acgttgccca cccggccagc agcaccaagg tggacaagaa aattgtgccc      720
agggattgtg gttgtaagcc ttgcatatgt acagtcccag aagtatcatc tgtcttcatc      780
ttccccccaa agcccaagga tgtgctcacc attactctga ctcctaaggt cacgtgtgtt      840
gtggtagaca tcagcaagga tgatcccgag gtccagttca gctggtttgt agatgatgtg      900
gaggtgcaca cagctcagac gcaaccccgg gaggagcagt tcaacagcac tttccgctca      960
gtcagtgaac ttcccatcat gcaccaggac tggctcaatg gcaaggagtt caaatgcagg     1020
gtcaacagtg cagctttccc tgcccccatc gagaaaacca tctccaaaac caaaggcaga     1080
ccgaaggctc cacaggtgta caccattcca cctcccaagg agcagatggc caaggataaa     1140
gtcagtctga cctgcatgat aacagacttc ttccctgagg acattactgt ggagtggcag     1200
tggaatgggc agccagcgga gaactacaag aacactcagc ccatcatgga cacagatggc     1260
tcttacttcg tctacagcaa gctcaatgtg cagaagagca ctgggaggc aggaaatact     1320 ttcacctgct ctgtgttaca tgagggcctg cacaaccacc atactgagaa gagcctctcc     1380
cactctcctg gtaaa                                                     1395
```

<210> SEQ ID NO 37
<211> LENGTH: 720
<212> TYPE: DNA
<213> ORGANISM: Artificial
<220> FEATURE:
<223> OTHER INFORMATION: Light chain of LpMab-3.

<400> SEQUENCE: 37

```
atggaatcac agacccaggt cctcatgttt cttctgctct gggtatctgg tgcctgtgca       60
gacattgtga tgacacagtc tccatcctcc ctggctatgt cagtaggaca gaaggtcact      120
atgaactgca agtccagtca gagccttta aatagtagca tcaaaagaa ctatctggcc        180 tggtaccagc agaaaccagg acagtctcct aaacttctgg tatattttgc atccactagg      240
gaatctgggg tccctgatcg cttcataggc agtggatctg ggacagattt cactcttacc      300
atcagcagtg cgcaggctga agacctggca gattatttct gtcagcaata ttatagcact      360
cctcccacgt tcggtgctgg gaccaagctg gagctgaaac gggctgatgc tgcaccaact      420
gtatccatct tcccaccatc cagtgagcag ttaacatctg gaggtgcctc agtcgtgtgc      480
ttcttgaaca acttctaccc caaagacatc aatgtcaagt ggaagattga tggcagtgaa      540
cgacaaaatg gcgtcctgaa cagttggact gatcaggaca gcaaagacag cacctacagc      600
atgagcagca ccctcacgtt gaccaaggac gagtatgaac gacataacag ctatacctgt      660
```
gaggccactc acaagacatc aacttcaccc attgtcaaga gcttcaacag gaatgagtgt    720

<210> SEQ ID NO 38
<211> LENGTH: 1386
<212> TYPE: DNA
<213> ORGANISM: Artificial
<220> FEATURE:
<223> OTHER INFORMATION: Heavy chain of LpMab-7.

<400> SEQUENCE: 38
atggactcca ggctcaattt agttttcctt gtccttattt taaaaggtgt ccagtgtgat     60
gtgcagctgg tggagtctgg gggaggctta gtgcagcctg agggtcccg gaaactctcc    120 tgtgcagcct ctggattcac tttcagtggc tttggaatgc actgggttcg tcaggctcca    180 gagaagggc tggagtgggt cgcatatatt agtagtgtca gtagtagaat ctactatgca    240
gacacagtga agggccgatt caccatctcc agagacaatc caagaacac cctgttcctg    300 caaatgacca gtctaaggtc tgaggacacg gccatgtatt attgtgcaag agagcaaact    360
gggcccgcct ggtttgctta ctggggccaa gggactctgg tcactgtctc tgcagccaaa    420
acgacacccc catctgtcta tccactggcc cctggatctg ctgcccaaac taactccatg    480
gtgaccctgg gatgcctggt caagggctat ttccctgagc cagtgacagt gacctggaac    540
tctggatccc tgtccagcgg tgtgcacacc ttcccagctg tcctgcagtc tgacctctac    600
actctgagca gctcagtgac tgtccctcc agcacctggc ccagcgagac cgtcacctgc    660
aacgttgccc acccggccag cagcaccaag gtggataaga aattgtgcc cagggattgt    720 ggttgtaagc cttgcatatg tacagtccca gaagtatcat ctgtcttcat cttcccccca    780
aagcccaagg atgtgctcac cattactctg actcctaagg tcacgtgtgt tgtggtagac    840
atcagcaagg atgatcccga ggtccagttc agctggtttg tagatgatgt ggaggtgcac    900
acagctcaga cgcaaccccg ggaggagcag ttcaacagca cttccgctc agtcagtgaa    960 cttcccatca tgcaccagga ctggctcaat ggcaaggagt tcaaatgcag ggtcaacagt   1020
gcagctttcc ctgccccat cgagaaaacc atctccaaaa ccaaaggcag accgaaggct   1080
ccacaggtgt acaccattcc acctcccaag gagcagatgg ccaaggataa agtcagtctg   1140
acctgcatga taacagactt cttccctgaa gacattactg tggagtggca gtggaatggg   1200
cagccagcgg agaactacaa gaacactcag cccatcatgg acacagatgg ctcttacttc   1260
gtctacagca agctcaatgt gcagaagagc aactgggagg cagggaatac tttcacctgc   1320
tctgtgttac atgagggcct gcacaaccac catactgaga gagcctctc ccactctcct   1380 ggtaaa                                                              1386

<210> SEQ ID NO 39
<211> LENGTH: 717
<212> TYPE: DNA
<213> ORGANISM: Artificial
<220> FEATURE:
<223> OTHER INFORMATION: Light chain of LpMab-7.

<400> SEQUENCE: 39
atgaagttgc tgttaggct gttggtgctg atgttctgga ttcctgcctc cagcagtgat     60
gttttgatga cccaaactcc actctccctg cctgtcagtc ttggagatca agcctccatc    120
tcttgcagat ctagtcggaa cattgttcaa agtactggaa acacctattt agaatggtac    180
ctgcagaaaa caggccagtc tccaaagctc ctgatcttca aagttccaa ccgattttct    240 ggggtcccag acaggttcag tggcagtgga tcagggacag atttcacact caagatcagt    300

```
agagtggagg ctgaggatct gggagtttat tactgctttc aaggttcaca tgttcctccg      360
tggacgttcg gtggaggcac caagctggaa atcaaacggg ctgatgctgc accaactgta      420
tccatcttcc caccatccag tgagcagtta acatctggag gtgcctcagt cgtgtgcttc      480
ttgaacaact tctaccccaa agacatcaat gtcaagtgga agattgatgg cagtgaacga      540
caaaatggcg tcctgaacag ttggactgat caggacagca agacagcac ctacagcatg       600 agcagcaccc tcacgttgac caaggacgag tatgaacgac ataacagcta cctgtgtgag      660
gccactcaca agacatcaac ttcacccatt gtcaagagct caacaggaa tgagtgt         717

<210> SEQ ID NO 40
<211> LENGTH: 1383
<212> TYPE: DNA
<213> ORGANISM: Artificial
<220> FEATURE:
<223> OTHER INFORMATION: Heavy chain of LpMab-9.

<400> SEQUENCE: 40
atggaatgtc tgtggaactt gctatttctc atggcagcag ctcaaagtat ccaagcacag       60
atccagttgg tgcagtctgg acctgagctg aagaagcctg agagacagt caggatctcc      120 tgcaaggctt ctgggtatac cttcacaaaa tctggaatgc agtgggttca aagatgtca      180 ggaaagggtt tgaagtggat tggctggata acaccccact ctggagtgcc aaaatatgca      240
gaagacttca agggacggtt tgccttctct ttggaaacct ctgccagcag tgcatattta      300
cagataagca acctcaaaaa tgaggacacg gctacgtatt tctgtgcgag atggggcggg      360
gacggggcta tggactactg gggtcaagga acctcagtca ccgtctcctc agccaaaacg      420 acaccccat ctgtctatcc actggcccct ggatctgctg cccaaactaa ctccatggtg       480
accctgggat gcctggtcaa gggctatttc cctgagccag tgacagtgac ctggaactct      540
ggatccctgt ccagcggtgt gcacaccttc ccagctgtcc tgcagtctga cctctacact      600
ctgagcagct cagtgactgt cccctccagc acctggccca gcgagaccgt cacctgcaac      660
gttgcccacc cggccagcag caccaaggtg gacaagaaaa ttgtgcccag ggattgtggt      720
tgtaagcctt gcatatgtac agtcccagaa gtatcatctg tcttcatctt cccccaaag      780 cccaaggatg tgctcaccat tactctgact cctaaggtca cgtgtgttgt ggtagacatc      840
agcaaggatg atcccgaggt ccagttcagc tggtttgtag atgatgtgga ggtgcacaca      900
gctcagacgc aaccccggga ggagcagttc aacagcactt tccgctcagt cagtgaactt      960
cccatcatgc accaggactg gctcaatggc aaggagttca atgcagggt caacagtgca     1020 gctttccctg cccccatcga gaaaaccatc tccaaaacca aggcagacc gaaggctcca     1080 caggtgtaca ccattccacc tcccaaggag cagatggcca aggataaagt cagtctgacc     1140
tgcatgataa cagacttctt ccctgaagac attactgtgg agtggcagtg gaatgggcag     1200
ccagcggaga actacaagaa cactcagccc atcatggaca cagatggctc ttacttcgtc     1260
tacagcaagc tcaatgtgca gaagagcaac tgggagacag gaaatacttt cacctgctct     1320
gtgttacatg agggcctgca caaccaccat actgagaaga gcctctccca ctctcctggt     1380
aaa                                                                   1383

<210> SEQ ID NO 41
<211> LENGTH: 720
<212> TYPE: DNA
<213> ORGANISM: Artificial
<220> FEATURE:
```

<223> OTHER INFORMATION: Light chain of LpMab-9.

<400> SEQUENCE: 41

```
atggaatcac agacccaggt cctcatgttt cttctgctct gggtatctgg tgcctgtgcg    60
gacattgtga tgacacagtc tccatcctcc ctgactatgt cagtaggaca gagggtcact   120
atgagctgca agtccagtca gagtctttta aagagtagca gtcaaaagaa ctatttggcc   180
tggtaccagc agaaaccagg acagtctcca aaacttctgg tatactttgc atccactagg   240
gaatctgggg tccctgatcg cttcataggc agtggatctg gacagattt cactcttacc    300
atcagcagtg tgcaggctga agacctggca gattacttct gtcaacaaca ttatagcgct   360
ccgctgtcgt tcggtgctgg gaccaagctg gagctgagac gggctgatgc tgcaccaact   420
gtatccatct tcccaccatc cagtgagcag ttaacatctg gaggtgcctc agtcgtgtgc   480
ttcttgaaca acttctaccc caaagacatc aatgtcaagt ggaagattga tggcagtgaa   540
cgacaaaatg gcgtcctgaa cagttggact gatcaggaca gcaaagacag cacctacagc   600
atgagcagca ccctcacgtt gaccaaggac gagtatgaac acataacag ctatacctgt    660
gaggccactc acaagacatc aacttcaccc attgtcaaga gcttcaacag gaatgagtgt   720
```

<210> SEQ ID NO 42
<211> LENGTH: 24
<212> TYPE: DNA
<213> ORGANISM: Artificial
<220> FEATURE:
<223> OTHER INFORMATION: Synthesized primer: LpMab-2HatgS.

<400> SEQUENCE: 42

```
atggaaaggc actggatctt tcta                                            24
```

<210> SEQ ID NO 43
<211> LENGTH: 24
<212> TYPE: DNA
<213> ORGANISM: Artificial
<220> FEATURE:
<223> OTHER INFORMATION: Synthesized primer: LpMab-3HatgS.

<400> SEQUENCE: 43

```
atgaactttg tgctcagctt gatt                                            24
```

<210> SEQ ID NO 44
<211> LENGTH: 24
<212> TYPE: DNA
<213> ORGANISM: Artificial
<220> FEATURE:
<223> OTHER INFORMATION: Synthesized primer: LpMab-7HatgS.

<400> SEQUENCE: 44

```
atggactcca ggctcaattt agtt                                            24
```

<210> SEQ ID NO 45
<211> LENGTH: 24
<212> TYPE: DNA
<213> ORGANISM: Artificial
<220> FEATURE:
<223> OTHER INFORMATION: Synthesized primer: LpMab-9HatgS.

<400> SEQUENCE: 45

```
atggaatgtc tgtggaactt gcta                                            24
```

<210> SEQ ID NO 46
<211> LENGTH: 20

```
<212> TYPE: DNA
<213> ORGANISM: Artificial
<220> FEATURE:
<223> OTHER INFORMATION: Synthesized primer: mIgG1woterAS.

<400> SEQUENCE: 46
tttaccagga gagtgggaga                                              20

<210> SEQ ID NO 47
<211> LENGTH: 24
<212> TYPE: DNA
<213> ORGANISM: Artificial
<220> FEATURE:
<223> OTHER INFORMATION: Synthesized primer: LpMab-2LatgS.

<400> SEQUENCE: 47
atgaagttgc ctgttaggct gttg                                         24

<210> SEQ ID NO 48
<211> LENGTH: 24
<212> TYPE: DNA
<213> ORGANISM: Artificial
<220> FEATURE:
<223> OTHER INFORMATION: Synthesized primer: LpMab-3LatgS.

<400> SEQUENCE: 48
atggaatcac agacccaggt cctc                                         24

<210> SEQ ID NO 49
<211> LENGTH: 24
<212> TYPE: DNA
<213> ORGANISM: Artificial
<220> FEATURE:
<223> OTHER INFORMATION: Synthesized primer: LpMab-7LatgS.

<400> SEQUENCE: 49
atgaagttgc ctgttaggct gttg                                         24

<210> SEQ ID NO 50
<211> LENGTH: 24
<212> TYPE: DNA
<213> ORGANISM: Artificial
<220> FEATURE:
<223> OTHER INFORMATION: Synthesized primer: LpMab-9LatgS.

<400> SEQUENCE: 50
atggaatcac agacccaggt cctc                                         24

<210> SEQ ID NO 51
<211> LENGTH: 20
<212> TYPE: DNA
<213> ORGANISM: Artificial
<220> FEATURE:
<223> OTHER INFORMATION: Synthesized primer: moIgCKwoterAS.

<400> SEQUENCE: 51
acactcattc ctgttgaagc                                              20

<210> SEQ ID NO 52
<211> LENGTH: 27
<212> TYPE: DNA
<213> ORGANISM: Artificial
<220> FEATURE:
<223> OTHER INFORMATION: Synthesized primer: hIgG1CH1.BamHI.

<400> SEQUENCE: 52
```
cacggatcca ccaagggccc atcggtc                                27

<210> SEQ ID NO 53
<211> LENGTH: 33
<212> TYPE: DNA
<213> ORGANISM: Artificial
<220> FEATURE:
<223> OTHER INFORMATION: Synthesized primer: hIgG1CH3-R1.NotI.

<400> SEQUENCE: 53
aatgcggccg ctcatttacc cggagacagg gag                         33

<210> SEQ ID NO 54
<211> LENGTH: 30
<212> TYPE: DNA
<213> ORGANISM: Artificial
<220> FEATURE:
<223> OTHER INFORMATION: Synthesized primer: HindIII-LpMab-2HatgS.

<400> SEQUENCE: 54
ggcaagctta tggaaaggca ctggatcttt                             30

<210> SEQ ID NO 55
<211> LENGTH: 30
<212> TYPE: DNA
<213> ORGANISM: Artificial
<220> FEATURE:
<223> OTHER INFORMATION: Synthesized primer: LpMab-2HVHR-BamHI.

<400> SEQUENCE: 55
gccggatcct gaggagactg tgagagtggt                             30

<210> SEQ ID NO 56
<211> LENGTH: 30
<212> TYPE: DNA
<213> ORGANISM: Artificial
<220> FEATURE:
<223> OTHER INFORMATION: Synthesized primer: HindIII-LpMab-3HatgS.

<400> SEQUENCE: 56
ggcaagctta tgaactttgt gctcagcttg                             30

<210> SEQ ID NO 57
<211> LENGTH: 30
<212> TYPE: DNA
<213> ORGANISM: Artificial
<220> FEATURE:
<223> OTHER INFORMATION: Synthesized primer: LpMab-3HVHR-BamHI.

<400> SEQUENCE: 57
gccggatcct gcagagacag tgaccagagt                             30

<210> SEQ ID NO 58
<211> LENGTH: 30
<212> TYPE: DNA
<213> ORGANISM: Artificial
<220> FEATURE:
<223> OTHER INFORMATION: Synthesized primer: HindIII-LpMab-7HatgS.

<400> SEQUENCE: 58
ggcaagctta tggactccag gctcaattta                             30

<210> SEQ ID NO 59
<211> LENGTH: 30
<212> TYPE: DNA
<213> ORGANISM: Artificial

```
<220> FEATURE:
<223> OTHER INFORMATION: Synthesized primer: LpMab-7HVHR-BamHI.

<400> SEQUENCE: 59
gccggatcct gcagagacag tgaccagagt                                   30

<210> SEQ ID NO 60
<211> LENGTH: 30
<212> TYPE: DNA
<213> ORGANISM: Artificial
<220> FEATURE:
<223> OTHER INFORMATION: Synthesized primer: HindIII-LpMab-9HatgS.

<400> SEQUENCE: 60
ggcaagctta tggaatgtct gtggaacttg                                   30

<210> SEQ ID NO 61
<211> LENGTH: 30
<212> TYPE: DNA
<213> ORGANISM: Artificial
<220> FEATURE:
<223> OTHER INFORMATION: Synthesized primer: LpMab-9HVHR-BamHI.

<400> SEQUENCE: 61
gccggatcct gaggagacgg tgactgaggt                                   30

<210> SEQ ID NO 62
<211> LENGTH: 1392
<212> TYPE: DNA
<213> ORGANISM: Artificial
<220> FEATURE:
<223> OTHER INFORMATION: Chimeric heavy chain of LpMab-2.

<400> SEQUENCE: 62
atggaaaggc actggatctt tctactcctg ttgtcagtaa ctgcaggtgt ccactcccag   60
gtccaggtgc agcagtctgg ggctgaactg gcaagacctg gggcctcagt gaagatgtcc  120
tgcaaggctt ctggctacac ctttactagc tacacgatac actgggtaaa acagaggcct  180
agacagggtc tggaatggat tggatacatt aatcctggca gtggttatac taattacaat  240
gagaagttcc aggacaaggc cacattgact gcagacaaat cctccaccac agcctacatg  300
caactgagca gcctgacatc tgaggactcc gcagtctatt actgtgcaag atgggatagg  360
ggctactggg gccaaggcac cactctcaca gtctcctcag gatccaccaa gggcccatcg  420
gtcttccccc tggcgccctg ctccaggagc acctccgaga gcacagcggc cctgggctgc  480
ctggtcaagg actacttccc cgaaccggtg acggtgtcgt ggaactcagg cgctctgacc  540
agcggcgtgc acaccttccc agctgtccta cagtcctcag gactctactc cctcagcagc  600
gtggtgaccg tgccctccag caacttcggc acccagacct acacctgcaa cgtagatcac  660
aagcccagca acaccaaggt ggacaagaca gttgagccca atcttgtga caaaactcac  720 acatgcccac cgtgcccagc acctgaactc ctggggggac cgtcagtctt cctcttcccc  780
ccaaaaccca aggacaccct catgatctcc cggacccctg aggtcacgtg cgtggtggtg  840
gacgtgagcc acgaagaccc cgaggtccag ttcaactggt acgtggacgg cgtggaggtg  900
cataatgcca agacaaagcc gcgggaggag cagtacaaca gcacgtaccg tgtggtcagc  960
gtcctcaccg tcctgcacca ggactggctg aatggcaagg agtacaaatg caaggtctcc 1020
aacaaagccc tcccagcccc catcgagaaa accatctcca aagccaaagg gcagccccga 1080
gaaccacagg tgtacaccct gcccccatcc cgggatgagc tgaccaagaa ccaggtcagc 1140
```

```
ctgacctgcc tggtcaaagg cttctatccc agcgacatcg ccgtggagtg ggagagcaat    1200
gggcagccgg agaacaacta caagaccacg cctcccgtgc tggactccga cggctccttc    1260
ttcctttaca gcaagctcac cgtggacaag agcaggtggc agcaggggaa cgtcttctca    1320
tgctccgtga tgcatgaggc tctgcacaac cactacacgc agaagagcct ctccctgtct    1380
ccgggtaaat ga                                                         1392

<210> SEQ ID NO 63
<211> LENGTH: 463
<212> TYPE: PRT
<213> ORGANISM: Artificial
<220> FEATURE:
<223> OTHER INFORMATION: Chimeric heavy chain of LpMab-2.

<400> SEQUENCE: 63
```

Met Glu Arg His Trp Ile Phe Leu Leu Leu Ser Val Thr Ala Gly
1               5                   10                  15

Val His Ser Gln Val Gln Val Gln Ser Gly Ala Glu Leu Ala Arg
                20                  25                  30

Pro Gly Ala Ser Val Lys Met Ser Cys Lys Ala Ser Gly Tyr Thr Phe
            35                  40                  45

Thr Ser Tyr Thr Ile His Trp Val Lys Gln Arg Pro Arg Gln Gly Leu
        50                  55                  60

Glu Trp Ile Gly Tyr Ile Asn Pro Gly Ser Gly Tyr Thr Asn Tyr Asn
65                  70                  75                  80

Glu Lys Phe Gln Asp Lys Ala Thr Leu Thr Ala Asp Lys Ser Ser Thr
                85                  90                  95

Thr Ala Tyr Met Gln Leu Ser Ser Leu Thr Ser Glu Asp Ser Ala Val
            100                 105                 110

Tyr Tyr Cys Ala Arg Trp Asp Arg Gly Tyr Trp Gly Gln Gly Thr Thr
        115                 120                 125

Leu Thr Val Ser Ser Gly Ser Thr Lys Gly Pro Ser Val Phe Pro Leu
    130                 135                 140

Ala Pro Cys Ser Arg Ser Thr Ser Glu Ser Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Asn
        195                 200                 205

Phe Gly Thr Gln Thr Tyr Thr Cys Asn Val Asp His Lys Pro Ser Asn
    210                 215                 220

Thr Lys Val Asp Lys Thr Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

```
Val Leu Thr Val Leu His Gln Asp Trp Leu Asn Gly Lys Glu Tyr Lys
            325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
            355                 360                 365

Pro Ser Arg Asp Glu Leu Thr Lys Asn Gln Val Ser Leu Thr Cys Leu
        370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Val Leu Asp Ser
            405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
        450                 455                 460

<210> SEQ ID NO 64
<211> LENGTH: 1416
<212> TYPE: DNA
<213> ORGANISM: Artificial
<220> FEATURE:
<223> OTHER INFORMATION: Chimeric heavy chain of LpMab-3.

<400> SEQUENCE: 64
atgaactttg tgctcagctt gattttcctt gccctcattt taaaaggtgt ccagtgtgaa      60
gtgcagctgg tggagtctgg gggaggctta gtgaagcctg agggtccct gaaactctcc      120 tgtgcagcct ctggattcac tttcactaga tatgccatgt cttgggttcg tcagactccg      180
gagaagaggc tggagtgggt cgcaaccatt agtaatggtg gtagttatac ctactattta      240
gacagtgtga aggtcgatt caccttatcc agagacaatg ccaagaacac cctgtacctg      300
caaatgagca gtctgaggtc tgaggacacg gccatgtatt actgtgcaag acgggagggc      360
ggacaggccg ggcccgcctg gtttgtttac tggggccaag ggactctggt cactgtctct      420
gcaggatcca ccaagggccc atcggtcttc cccctggcgc cctgctccag gagcacctcc      480
gagagcacag cggccctggg ctgcctggtc aaggactact cccccgaacc ggtgacggtg      540
tcgtggaact caggcgctct gaccagcggc gtgcacacct tcccagctgt cctacagtcc      600
tcaggactct actccctcag cagcgtggtg accgtgccct ccagcaactt cggcacccag      660
acctacacct gcaacgtaga tcacaagccc agcaacacca aggtggacaa gacagttgag      720
cccaaatctt gtgacaaaac tcacacatgc ccaccgtgcc cagcacctga actcctgggg      780
ggaccgtcag tcttcctctt ccccccaaaa cccaaggaca ccctcatgat ctcccggacc      840
cctgaggtca cgtgcgtggt ggtggacgtg agccacgaag accccgaggt ccagttcaac      900
tggtacgtgg acggcgtgga ggtgcataat gccaagacaa agccgcggga ggagcagtac      960
aacagcacgt accgtgtggt cagcgtcctc accgtcctgc accaggactg gctgaatggc     1020
aaggagtaca aatgcaaggt ctccaacaaa gccctcccag cccccatcga gaaaaccatc     1080
tccaaagcca agggcagcc cgagaacca caggtgtaca ccctgccccc atcccgggat     1140
gagctgacca agaaccaggt cagcctgacc tgcctggtca aaggcttcta tcccagcgac     1200
atcgccgtgg agtgggagag caatgggcag ccggagaaca actacaagac cacgcctccc     1260
```

```
gtgctggact ccgacggctc cttcttcctt tacagcaagc tcaccgtgga caagagcagg      1320
tggcagcagg ggaacgtctt ctcatgctcc gtgatgcatg aggctctgca caaccactac      1380
acgcagaaga gcctctccct gtctccgggt aaatga                                1416
```

<210> SEQ ID NO 65
<211> LENGTH: 471
<212> TYPE: PRT
<213> ORGANISM: Artificial
<220> FEATURE:
<223> OTHER INFORMATION: Chimeric heavy chain of LpMab-3.

<400> SEQUENCE: 65

```
Met Asn Phe Val Leu Ser Leu Ile Phe Leu Ala Leu Ile Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Thr Arg Tyr Ala Met Ser Trp Val Arg Gln Thr Pro Glu Lys Arg Leu
    50                  55                  60

Glu Trp Val Ala Thr Ile Ser Asn Gly Gly Ser Tyr Thr Tyr Tyr Leu
65                  70                  75                  80

Asp Ser Val Lys Gly Arg Phe Thr Leu Ser Arg Asp Asn Ala Lys Asn
                85                  90                  95

Thr Leu Tyr Leu Gln Met Ser Ser Leu Arg Ser Glu Asp Thr Ala Met
            100                 105                 110

Tyr Tyr Cys Ala Arg Arg Glu Gly Gly Gln Ala Gly Pro Ala Trp Phe
        115                 120                 125

Val Tyr Trp Gly Gln Gly Thr Leu Val Thr Val Ser Ala Gly Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Gln Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335
```

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
            405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 66
<211> LENGTH: 1407
<212> TYPE: DNA
<213> ORGANISM: Artificial
<220> FEATURE:
<223> OTHER INFORMATION: Chimeric heavy chain of LpMab-7.

<400> SEQUENCE: 66
atggactcca ggctcaattt agttttcctt gtccttattt taaaaggtgt ccagtgtgat      60
gtgcagctgg tggagtctgg gggaggctta gtgcagcctg agggtcccg gaaactctcc     120 tgtgcagcct ctggattcac tttcagtggc tttggaatgc actgggttcg tcaggctcca     180
gagaaggggc tggagtgggt cgcatatatt agtagtgtca gtagtagaat ctactatgca     240
gacacagtga agggccgatt caccatctcc agagacaatc caagaacac cctgttcctg      300 caaatgacca gtctaaggtc tgaggacacg gccatgtatt attgtgcaag agagcaaact     360
gggcccgcct ggtttgctta ctggggccaa gggactctgg tcactgtctc tgcaggatcc     420
accaagggcc catcggtctt ccccctggcg cctgctcca ggagcacctc cgagagcaca     480
gcggccctgg gctgcctggt caaggactac ttccccgaac cggtgacggt gtcgtggaac     540
tcaggcgctc tgaccagcgg cgtgcacacc ttcccagctg tcctacagtc ctcaggactc     600
tactccctca gcagcgtggt gaccgtgccc tccagcaact cggcaccca gacctacacc      660 tgcaacgtag atcacaagcc cagcaacacc aaggtggaca agacagttga gcccaaatct     720
tgtgacaaaa ctcacacatg cccaccgtgc ccagcacctg aactcctggg gggaccgtca     780
gtcttcctct tccccccaa acccaaggac accctcatga tctcccggac ccctgaggtc     840
acgtgcgtgg tggtggacgt gagccacgaa gaccccgagg tccagttcaa ctggtacgtg     900
gacggcgtgg aggtgcataa tgccaagaca agccgcggg aggagcagta caacagcacg      960
taccgtgtgg tcagcgtcct caccgtcctg caccaggact ggctgaatgg caaggagtac    1020
aaatgcaagg tctccaacaa agccctccca gcccccatcg agaaaaccat ctccaaagcc    1080
aaagggcagc cccgagaacc acaggtgtac accctgcccc catcccggga tgagctgacc    1140
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260

```
tccgacggct ccttcttcct ttacagcaag ctcaccgtgg acaagagcag gtggcagcag      1320
gggaacgtct tctcatgctc cgtgatgcat gaggctctgc acaaccacta cacgcagaag      1380
agcctctccc tgtctccggg taaatga                                          1407
```

<210> SEQ ID NO 67
<211> LENGTH: 468
<212> TYPE: PRT
<213> ORGANISM: Artificial
<220> FEATURE:
<223> OTHER INFORMATION: Chimeric heavy chain of LpMab-7.

<400> SEQUENCE: 67

```
Met Asp Ser Arg Leu Asn Leu Val Phe Leu Val Leu Ile Leu Lys Gly
1               5                  10                  15

Val Gln Cys Asp Val Gln Leu Val Glu Ser Gly Gly Gly Leu Val Gln
            20                  25                  30

Pro Gly Gly Ser Arg Lys Leu Ser Cys Ala Ala Ser Gly Phe Thr Phe
        35                  40                  45

Ser Gly Phe Gly Met His Trp Val Arg Gln Ala Pro Glu Lys Gly Leu
    50                  55                  60

Glu Trp Val Ala Tyr Ile Ser Ser Val Ser Ser Arg Ile Tyr Tyr Ala
65                  70                  75                  80

Asp Thr Val Lys Gly Arg Phe Thr Ile Ser Arg Asp Asn Pro Lys Asn
                85                  90                  95

Thr Leu Phe Leu Gln Met Thr Ser Leu Arg Ser Glu Asp Thr Ala Met
            100                 105                 110

Tyr Tyr Cys Ala Arg Glu Gln Thr Gly Pro Ala Trp Phe Ala Tyr Trp
        115                 120                 125

Gly Gln Gly Thr Leu Val Thr Val Ser Ala Gly Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335
```

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 68
<211> LENGTH: 1404
<212> TYPE: DNA
<213> ORGANISM: Artificial
<220> FEATURE:
<223> OTHER INFORMATION: Chimeric heavy chain of LpMab-9.

<400> SEQUENCE: 68

```
atggaatgtc tgtggaactt gctatttctc atggcagcag ctcaaagtat ccaagcacag    60
atccagttgg tgcagtctgg acctgagctg aagaagcctg agagacagt caggatctcc    120
tgcaaggctt ctgggtatac cttcacaaaa tctggaatgc agtgggttca aagatgtca    180
ggaaagggtt tgaagtggat tggctggata acacccact ctggagtgcc aaaatatgca    240
gaagacttca agggacggtt tgccttctct ttggaaacct ctgccagcag tgcatattta    300
cagataagca acctcaaaaa tgaggacacg gctacgtatt tctgtgcgag atggggcggg    360
gacggggcta tggactactg gggtcaagga acctcagtca ccgtctcctc aggatccacc    420
aagggcccat cggtcttccc cctggcgccc tgctccagga gcacctccga gagcacagcg    480
gccctgggct gcctggtcaa ggactacttc cccgaaccgg tgacggtgtc gtggaactca    540
ggcgctctga ccagcggcgt gcacaccttc ccagctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttgagcc caaatcttgt    720
gacaaaactc acacatgccc accgtgccca gcacctgaac tcctgggggg accgtcagtc    780
ttcctcttcc ccccaaaacc caaggacacc ctcatgatct cccggacccc tgaggtcacg    840
tgcgtggtgg tggacgtgag ccacgaagac cccgaggtcc agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaaa   1020
tgcaaggtct ccaacaaagc cctcccagcc cccatcgaga aaaccatctc caaagccaaa   1080
ggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
```

-continued gacggctcct tcttccttta cagcaagctc accgtggaca agagcaggtg gcagcagggg    1320
aacgtcttct catgctccgt gatgcatgag gctctgcaca accactacac gcagaagagc    1380
ctctccctgt ctccgggtaa atga                                            1404

<210> SEQ ID NO 69
<211> LENGTH: 467
<212> TYPE: PRT
<213> ORGANISM: Artificial
<220> FEATURE:
<223> OTHER INFORMATION: Chimeric heavy chain of LpMab-9.

<400> SEQUENCE: 69

Met Glu Cys Leu Trp Asn Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Arg Ile Ser Cys Lys Ala Ser Gly Tyr Thr Phe
        35                  40                  45

Thr Lys Ser Gly Met Gln Trp Val Gln Lys Met Ser Gly Lys Gly Leu
    50                  55                  60

Lys Trp Ile Gly Trp Ile Asn Thr His Ser Gly Val Pro Lys Tyr Ala
65                  70                  75                  80

Glu Asp Phe Lys Gly Arg Phe Ala Phe Ser Leu Glu Thr Ser Ala Ser
                85                  90                  95

Ser Ala Tyr Leu Gln Ile Ser Asn Leu Lys Asn Glu Asp Thr Ala Thr
            100                 105                 110

Tyr Phe Cys Ala Arg Trp Gly Gly Asp Gly Ala Met Asp Tyr Trp Gly
        115                 120                 125

Gln Gly Thr Ser Val Thr Val Ser Ser Gly Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 70
<211> LENGTH: 162
<212> TYPE: PRT
<213> ORGANISM: Homo sapiens

<400> SEQUENCE: 70

Met Trp Lys Val Ser Ala Leu Leu Phe Val Leu Gly Ser Ala Ser Leu
1               5                   10                  15

Trp Val Leu Ala Glu Gly Ala Ser Thr Gly Gln Pro Glu Asp Asp Thr
            20                  25                  30

Glu Thr Thr Gly Leu Glu Gly Gly Val Ala Met Pro Gly Ala Glu Asp
        35                  40                  45

Asp Val Val Thr Pro Gly Thr Ser Glu Asp Arg Tyr Lys Ser Gly Leu
    50                  55                  60

Thr Thr Leu Val Ala Thr Ser Val Asn Ser Val Thr Gly Ile Arg Ile
65                  70                  75                  80

Glu Asp Leu Pro Thr Ser Glu Ser Thr Val His Ala Gln Glu Gln Ser
                85                  90                  95

Pro Ser Ala Thr Ala Ser Asn Val Ala Thr Ser His Ser Thr Glu Lys
            100                 105                 110

Val Asp Gly Asp Thr Gln Thr Thr Val Glu Lys Asp Gly Leu Ser Thr
            115                 120                 125

Val Thr Leu Val Gly Ile Ile Val Gly Val Leu Leu Ala Ile Gly Phe
            130                 135                 140

Ile Gly Gly Ile Ile Val Val Val Met Arg Lys Met Ser Gly Arg Tyr
145                 150                 155                 160

Ser Pro

<210> SEQ ID NO 71
<211> LENGTH: 10
<212> TYPE: PRT
<213> ORGANISM: Artificial
<220> FEATURE:
<223> OTHER INFORMATION: Heavy chain CDR1 of LpMab-23.

<400> SEQUENCE: 71

Gly Phe Ser Val Thr Ser Tyr Gly Ile His

<210> SEQ ID NO 72
<211> LENGTH: 16
<212> TYPE: PRT
<213> ORGANISM: Artificial
<220> FEATURE:
<223> OTHER INFORMATION: Heavy chain CDR2 of LpMab-23.

<400> SEQUENCE: 72

Val Ile Trp Thr Ser Gly Asn Thr Asn Tyr Asn Ser Ala Leu Met Ser
1               5                   10                  15

<210> SEQ ID NO 73
<211> LENGTH: 10
<212> TYPE: PRT
<213> ORGANISM: Artificial
<220> FEATURE:
<223> OTHER INFORMATION: Heavy chain CDR3 of LpMab-23.

<400> SEQUENCE: 73

Glu Asp Tyr Tyr Gly Tyr Ala Met Asp Tyr
1               5                   10

<210> SEQ ID NO 74
<211> LENGTH: 16
<212> TYPE: PRT
<213> ORGANISM: Artificial
<220> FEATURE:
<223> OTHER INFORMATION: Light chain CDR1 of LpMab-23.

<400> SEQUENCE: 74

Arg Ser Ser Gln Ser Leu Leu Tyr Ser Asn Gly Lys Thr Tyr Leu Asn
1               5                   10                  15

<210> SEQ ID NO 75
<211> LENGTH: 7
<212> TYPE: PRT
<213> ORGANISM: Artificial
<220> FEATURE:
<223> OTHER INFORMATION: Light chain CDR2 of LpMab-23.

<400> SEQUENCE: 75

Leu Val Ser Lys Leu Asp Ser
1               5

<210> SEQ ID NO 76
<211> LENGTH: 9
<212> TYPE: PRT
<213> ORGANISM: Artificial
<220> FEATURE:
<223> OTHER INFORMATION: Light chain CDR3 of LpMab-23.

<400> SEQUENCE: 76

Val Gln Gly Thr His Phe Pro Trp Thr
1               5

<210> SEQ ID NO 77
<211> LENGTH: 239
<212> TYPE: PRT
<213> ORGANISM: Artificial
<220> FEATURE:
<223> OTHER INFORMATION: Light chain of LpMab-23.

<400> SEQUENCE: 77

Met Met Ser Pro Ala Gln Phe Leu Phe Leu Leu Val Leu Trp Ile Gln
1               5                   10                  15

Glu Ala Thr Gly Asp Val Val Met Thr Gln Thr Pro Phe Thr Leu Ser
            20                  25                  30

Val Ser Ile Gly Gln Pro Ala Ser Ile Ser Cys Arg Ser Ser Gln Ser
        35                  40                  45

Leu Leu Tyr Ser Asn Gly Lys Thr Tyr Leu Asn Trp Leu Leu Gln Arg
 50                  55                  60

Pro Gly Gln Ser Pro Lys Arg Leu Ile Tyr Leu Val Ser Lys Leu Asp
 65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Ile Tyr Tyr
            100                 105                 110

Cys Val Gln Gly Thr His Phe Pro Trp Thr Phe Gly Gly Gly Thr Lys
        115                 120                 125

Leu Glu Ile Lys Arg Ala Asp Ala Ala Pro Thr Val Ser Ile Phe Pro
130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Asn Glu Cys
225                 230                 235

<210> SEQ ID NO 78
<211> LENGTH: 461
<212> TYPE: PRT
<213> ORGANISM: Artificial
<220> FEATURE:
<223> OTHER INFORMATION: Heavy chain of LpMab-23.

<400> SEQUENCE: 78

Met Ala Val Leu Val Leu Phe Leu Cys Leu Val Ala Phe Pro Ser Cys
 1               5                  10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Val
        35                  40                  45

Thr Ser Tyr Gly Ile His Trp Val Arg Gln Pro Pro Gly Lys Gly Leu
 50                  55                  60

Glu Trp Leu Gly Val Ile Trp Thr Ser Gly Asn Thr Asn Tyr Asn Ser
 65                  70                  75                  80

Ala Leu Met Ser Arg Leu Ser Ile Ser Arg Asp Asn Ser Lys Ser Gln
                85                  90                  95

Val Phe Leu Lys Met Asn Ser Leu Gln Thr Asp Asp Thr Ala Met Tyr
            100                 105                 110

Tyr Cys Ala Arg Glu Asp Tyr Tyr Gly Tyr Ala Met Asp Tyr Trp Gly
        115                 120                 125

Gln Gly Thr Ser Val Thr Val Ser Ser Ala Lys Thr Thr Pro Pro Ser
130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
            165                 170                 175

Thr Trp Asn Ser Gly Ser Leu Ser Ser Gly Val His Thr Phe Pro Ala
        180                 185                 190

Val Leu Gln Ser Asp Leu Tyr Thr Leu Ser Ser Ser Val Thr Val Pro
            195                 200                 205

Ser Ser Thr Trp Pro Ser Glu Thr Val Thr Cys Asn Val Ala His Pro
210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
            245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
            275                 280                 285

Phe Ser Trp Phe Val Asp Asp Val Glu Val His Thr Ala Gln Thr Gln
290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
            325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
            355                 360                 365

Lys Glu Gln Met Ala Lys Asp Lys Val Ser Leu Thr Cys Met Ile Thr
370                 375                 380

Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
            405                 410                 415

Ser Tyr Phe Val Tyr Ser Lys Leu Asn Val Gln Lys Ser Asn Trp Glu
            420                 425                 430

Ala Gly Asn Thr Phe Thr Cys Ser Val Leu His Glu Gly Leu His Asn
            435                 440                 445

His His Thr Glu Lys Ser Leu Ser His Ser Pro Gly Lys
450                 455                 460

<210> SEQ ID NO 79
<211> LENGTH: 720
<212> TYPE: DNA
<213> ORGANISM: Artificial
<220> FEATURE:
<223> OTHER INFORMATION: Light chain of LpMab-23.

<400> SEQUENCE: 79
atgatgagtc ctgcccagtt cctgtttctg ttagtgctct ggattcagga agccaccggt      60
gatgttgtga tgacccagac tccattcact tgtcggtttt ccattggaca accagcctct     120
atctcttgca ggtcaagtca gagcctctta tatagtaatg gaaaaaccta tttgaattgg     180
ttattacaga ggccaggcca gtctccaaag cgcctaatct atctggtgtc taaactggac     240

```
tctggagtcc ctgacaggtt cactggcagt ggatcaggaa cagattttac actgaaaatc    300
agcagagtgg aggctgagga tttgggaatt tattactgcg tgcaaggtac acattttccg    360
tggacgttcg gtggaggcac caagctggaa atcaaacggg ctgatgctgc accaactgta    420
tccatcttcc caccatccag tgagcagtta acatctggag gtgcctcagt cgtgtgcttc    480
ttgaacaact ctaccccaa agacatcaat gtcaagtgga agattgatgg cagtgaacga    540
caaaatggcg tcctgaacag ttggactgat caggacagca agacagcac ctacagcatg    600 agcagcaccc tcacgttgac caaggacgag tatgaacgac ataacagcta tacctgtgag    660
gccactcaca agacatcaac ttcacccatt gtcaagagct caacaggaa tgagtgttag    720
```

<210> SEQ ID NO 80
<211> LENGTH: 1386
<212> TYPE: DNA
<213> ORGANISM: Artificial
<220> FEATURE:
<223> OTHER INFORMATION: Heavy chain of LpMab-23.

<400> SEQUENCE: 80

```
atggctgtcc tggtgctgtt cctctgcctg gttgcatttc caagctgtgt cctgtcccag     60
gtgcagctga aggagtcagg acctggcctg gtggcgccct cacagagcct gtccatcact    120
tgcactgtct ctggattttc agtaaccagt tatggtatac attgggttcg ccagcctcca    180
ggaaagggtc tggagtggct gggagtgatt tggactagtg aaatacaaa ttataattcg    240 gctctcatgt ccagactgag catcagcaga acaactcca agagccaagt tttcttaaaa    300
atgaacagtc tgcaaactga tgacacagcc atgtactact gtgccagaga ggattactac    360
gggtatgcta tggactactg ggtcaagga acctcagtca ccgtctcctc agccaaaacg    420
acacccccat ctgtctatcc actggcccct ggatctgctg cccaaactaa ctccatggtg    480
accctgggat gcctggtcaa gggctatttc cctgagccag tgacagtgac ctggaactct    540
ggatccctgt ccagcggtgt gcacaccttc ccagctgtcc tgcagtctga cctctacact    600
ctgagcagct cagtgactgt cccctccagc acctggccca gcgagaccgt cacctgcaac    660
gttgcccacc cggccagcag caccaaggtg gacaagaaaa ttgtgcccag ggattgtggt    720
tgtaagcctt gcatatgtac agtcccagaa gtatcatctg tcttcatctt cccccccaaag   780 cccaaggatg tgctcaccat tactctgact cctaaggtca cgtgtgttgt ggtagacatc    840
agcaaggatg atcccgaggt ccagttcagc tggtttgtag atgatgtgga ggtgcacaca    900
gctcagacgc aacccgggga ggagcagttc aacagcactt tccgctcagt cagtgaactt    960
cccatcatgc accaggactg gctcaatggc aaggagttca atgcagggt caacagtgca   1020 gctttcctg ccccatcga gaaaaccatc tccaaaacca aaggcagacc gaaggctcca   1080
caggtgtaca ccattccacc tcccaaggag cagatggcca aggataaagt cagtctgacc   1140
tgcatgataa cagacttctt ccctgaagac attactgtgg agtggcagtg gaatgggcag   1200
ccagcggaga actacaagaa cactcagccc atcatggaca cagatggctc ttacttcgtc   1260
tacagcaagc tcaatgtgca gaagagcaac tgggaggcag aaatactttt cacctgctct   1320
gtgttacatg agggcctgca caaccaccat actgagaaga gcctctccca ctctcctggt   1380
aaatga                                                               1386
```

<210> SEQ ID NO 81
<211> LENGTH: 29
<212> TYPE: DNA
<213> ORGANISM: Artificial

```
<220> FEATURE:
<223> OTHER INFORMATION: LpMab-23HatgS.

<400> SEQUENCE: 81
aataagctta gcatggctgt cctggtgct                                29

<210> SEQ ID NO 82
<211> LENGTH: 32
<212> TYPE: DNA
<213> ORGANISM: Artificial
<220> FEATURE:
<223> OTHER INFORMATION: mIgG1terAS.

<400> SEQUENCE: 82
ggcggccgct catttaccag gagagtggga ga                            32

<210> SEQ ID NO 83
<211> LENGTH: 30
<212> TYPE: DNA
<213> ORGANISM: Artificial
<220> FEATURE:
<223> OTHER INFORMATION: LpMab-23LatgS.

<400> SEQUENCE: 83
aataagctta aaatgatgag tcctgcccag                               30

<210> SEQ ID NO 84
<211> LENGTH: 30
<212> TYPE: DNA
<213> ORGANISM: Artificial
<220> FEATURE:
<223> OTHER INFORMATION: moIgCKterAS.

<400> SEQUENCE: 84
ggcggccgcc taacactcat tcctgttgaa                               30

<210> SEQ ID NO 85
<211> LENGTH: 469
<212> TYPE: PRT
<213> ORGANISM: Artificial
<220> FEATURE:
<223> OTHER INFORMATION: Heavy chain of chLpMab-23.

<400> SEQUENCE: 85
```

Met Ala Val Leu Val Leu Phe Leu Cys Leu Val Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Val
        35                  40                  45

Thr Ser Tyr Gly Ile His Trp Val Arg Gln Pro Pro Gly Lys Gly Leu
    50                  55                  60

Glu Trp Leu Gly Val Ile Trp Thr Ser Gly Asn Thr Asn Tyr Asn Ser
65                  70                  75                  80

Ala Leu Met Ser Arg Leu Ser Ile Ser Arg Asp Asn Ser Lys Ser Gln
                85                  90                  95

Val Phe Leu Lys Met Asn Ser Leu Gln Thr Asp Asp Thr Ala Met Tyr
            100                 105                 110

Tyr Cys Ala Arg Glu Asp Tyr Tyr Gly Tyr Ala Met Asp Tyr Trp Gly
        115                 120                 125

Gln Gly Thr Ser Val Thr Val Ser Ser Ala Lys Gly Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
                195                 200                 205

Thr Val Pro Ser Ser Asn Phe Gly Thr Gln Thr Tyr Thr Cys Asn Val
            210                 215                 220

Asp His Lys Pro Ser Asn Thr Lys Val Asp Lys Thr Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Gln Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
    450                 455                 460

Leu Ser Pro Gly Lys
465

<210> SEQ ID NO 86
<211> LENGTH: 241
<212> TYPE: PRT
<213> ORGANISM: Artificial
<220> FEATURE:
<223> OTHER INFORMATION: Light chain of chLpMab-23.

<400> SEQUENCE: 86

Met Met Ser Pro Ala Gln Phe Leu Phe Leu Leu Val Leu Trp Ile Gln
1               5                   10                  15

Glu Ala Thr Gly Asp Val Val Met Thr Gln Thr Pro Phe Thr Leu Ser
            20                  25                  30

Val Ser Ile Gly Gln Pro Ala Ser Ile Ser Cys Arg Ser Gln Ser
         35                  40                  45

Leu Leu Tyr Ser Asn Gly Lys Thr Tyr Leu Asn Trp Leu Leu Gln Arg
 50                  55                  60

Pro Gly Gln Ser Pro Lys Arg Leu Ile Tyr Leu Val Ser Lys Leu Asp
 65                  70                  75                  80

Ser Gly Val Pro Asp Arg Phe Thr Gly Ser Gly Ser Gly Thr Asp Phe
                 85                  90                  95

Thr Leu Lys Ile Ser Arg Val Glu Ala Glu Asp Leu Gly Ile Tyr Tyr
             100                 105                 110

Cys Val Gln Gly Thr His Phe Pro Trp Thr Phe Gly Gly Gly Thr Lys
         115                 120                 125

Leu Lys Ile Lys Arg Gly Ser Thr Val Ala Ala Pro Ser Val Phe Ile
     130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                 165                 170                 175

Val Asp Asn Ala Leu Gln Ser Gly Asn Ser Gln Glu Ser Val Thr Glu
             180                 185                 190

Gln Asp Ser Lys Asp Ser Thr Tyr Ser Leu Ser Ser Thr Leu Thr Leu
         195                 200                 205

Ser Lys Ala Asp Tyr Glu Lys His Lys Val Tyr Ala Cys Glu Val Thr
     210                 215                 220

His Gln Gly Leu Ser Ser Pro Val Thr Lys Ser Phe Asn Arg Gly Glu
225                 230                 235                 240

Cys

<210> SEQ ID NO 87
<211> LENGTH: 1410
<212> TYPE: DNA
<213> ORGANISM: Artificial
<220> FEATURE:
<223> OTHER INFORMATION: Heavy chain of chLpMab-23.

<400> SEQUENCE: 87
atggctgtcc tggtgctgtt cctctgcctg gttgcatttc caagctgtgt cctgtcccag    60
gtgcagctga aggagtcagg acctggcctg gtggcgccct cacagagcct gtccatcact   120
tgcactgtct ctggattttc agtaaccagt tatggtatac attgggttcg ccagcctcca   180
ggaaagggtc tggagtggct gggagtgatt tggactagtg gaaatacaaa ttataattcg   240
gctctcatgt ccagactgag catcagcaga gacaactcca agagccaagt tttcttaaaa   300
atgaacagtc tgcaaactga tgacacagcc atgtactact gtgccagaga ggattactac   360
gggtatgcta tggactactg gggtcaagga acctcagtca ccgtctcctc agccaaagga   420
tccaccaagg gcccatcggt cttccccctg gcgccctgct ccaggagcac ctccgagagc   480
acagcggccc tgggctgcct ggtcaaggac tacttccccg aaccggtgac ggtgtcgtgg   540
aactcaggcg ctctgaccag cggcgtgcac accttcccag ctgtcctaca gtcctcagga   600
ctctactccc tcagcagcgt ggtgaccgtg ccctccagca acttcggcac ccagacctac   660
acctgcaacg tagatcacaa gcccagcaac accaaggtgg acaagacagt tgagcccaaa   720
tcttgtgaca aaactcacac atgcccaccg tgcccagcac ctgaactcct ggggggaccg   780
tcagtcttcc tcttcccccc aaaacccaag gacaccctca tgatctcccg gacccctgag   840

```
gtcacgtgcg tggtggtgga cgtgagccac gaagacccg aggtccagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaaatgca aggtctccaa caaagccctc ccagccccca tcgagaaaac catctccaaa   1080
gccaaagggc agccccgaga accacaggtg tacaccctgc ccccatcccg ggatgagctg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctttacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga                                     1410

<210> SEQ ID NO 88
<211> LENGTH: 726
<212> TYPE: DNA
<213> ORGANISM: Artificial
<220> FEATURE:
<223> OTHER INFORMATION: Light chain of chLpMab-23.

<400> SEQUENCE: 88
atgatgagtc ctgcccagtt cctgtttctg ttagtgctct ggattcagga agccaccggt     60
gatgttgtga tgacccagac tccattcact ttgtcggttt ccattggaca accagcctct    120
atctcttgca ggtcaagtca gagcctctta tatagtaatg gaaaaaccta tttgaattgg    180
ttattacaga ggccaggcca gtctccaaag cgcctaatct atctggtgtc taaactggac    240
tctggagtcc ctgacaggtt cactggcagt ggatcaggaa cagattttac actgaaaatc    300
agcagagtgg aggctgagga tttgggaatt tattactgcg tgcaaggtac acattttccg    360
tggacgttcg gtggaggcac caagctgaaa atcaaacggg atccactgt ggctgcacca    420 tctgtcttca tcttcccgcc atctgatgag cagttgaaat ctggaactgc ctctgttgtg    480
tgcctgctga ataacttcta tcccagagag gccaaagtac agtggaaggt ggataacgcc    540
ctccaatcgg gtaactccca ggagagtgtc acagagcagg acagcaagga cagcacctac    600
agcctcagca gcaccctgac gctgagcaaa gcagactacg agaaacacaa agtctacgcc    660
tgcgaagtca cccatcaggg cctgagctcg cccgtcacaa agagcttcaa caggggagag    720
tgttag                                                                726
```